(12) United States Patent
King et al.

(10) Patent No.: US 8,722,670 B2
(45) Date of Patent: May 13, 2014

(54) SELECTIVE NR2B ANTAGONISTS

(71) Applicant: Bristol-Myers Squibb Company, Princeton, NJ (US)

(72) Inventors: Dalton King, Hamden, CT (US); Richard E. Olson, Orange, CT (US); John E. Macor, Guilford, CT (US); Imadul Islam, Bangalore (IN); Srinivasan Thangathirupathy, Bangalore (IN); Jayakumar Sankara Warrier, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/627,130

(22) Filed: Sep. 26, 2012

(65) Prior Publication Data

US 2013/0085138 A1  Apr. 4, 2013

Related U.S. Application Data

(60) Provisional application No. 61/541,373, filed on Sep. 30, 2011.

(51) Int. Cl.
  *C07D 413/14* (2006.01)
  *C07D 487/04* (2006.01)
  *A61K 31/4709* (2006.01)
  *A61K 31/4245* (2006.01)

(52) U.S. Cl.
  USPC ... 514/230.5; 514/312; 514/364; 514/252.05; 514/249; 514/262.1; 514/275; 544/238; 544/354; 544/105; 544/262; 544/331; 546/158; 546/157; 548/143

(58) Field of Classification Search
  USPC ............. 514/230.5, 312, 364, 252.05, 249, 514/262.1, 275; 544/238, 354, 105, 262, 544/331; 546/158, 157; 548/143
  See application file for complete search history.

(56) References Cited

U.S. PATENT DOCUMENTS

| | | |
|---|---|---|
| 6,316,474 B1 | 11/2001 | McCauley et al. |
| 2005/0245530 A1 | 11/2005 | Borzilleri et al. |
| 2006/0128734 A1 | 6/2006 | Floersheimer et al. |
| 2008/0090856 A1 | 4/2008 | Flynn et al. |
| 2009/0136472 A1* | 5/2009 | Westman et al. ............ 424/94.1 |
| 2009/0149467 A1 | 6/2009 | Dinsmore et al. |
| 2009/0253710 A1 | 10/2009 | Liotta et al. |
| 2010/0029610 A1 | 2/2010 | Singh et al. |
| 2011/0159019 A1 | 6/2011 | Tanaka et al. |
| 2012/0009151 A1 | 1/2012 | Han et al. |
| 2013/0079338 A1 | 3/2013 | King et al. |

\* cited by examiner

*Primary Examiner* — Kahsay Habte
(74) *Attorney, Agent, or Firm* — James Epperson

(57) ABSTRACT

The disclosure generally relates to compounds of formula I, including their salts, as well as compositions and methods of using the compounds. The compounds are ligands, antagonists of the NR2B receptor and may be useful for the treatment of various disorders of the central nervous system.

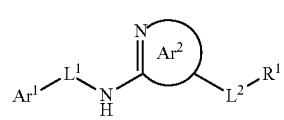

13 Claims, No Drawings

SELECTIVE NR2B ANTAGONISTS

CROSS-REFERENCE TO RELATED APPLICATIONS

This application claims the benefit of U.S. provisional application Ser. No. 61/541,373 filed Sep. 30, 2011.

BACKGROUND OF THE INVENTION

The disclosure generally relates to compounds of formula I, including their salts, as well as compositions and methods of using the compounds. The compounds are ligands for the NR2B NMDA receptor and may be useful for the treatment of various disorders of the central nervous system.

N-Methyl-D-aspartate (NMDA) receptors are ion channels which are gated by the binding of glutamate, an excitatory neurotransmitter in the central nervous system. They are thought to play a key role in the development of a number of neurological diseases, including depression, neuropathic pain, Alzheimer's disease, and Parkinson's disease. Functional NMDA receptors are tetrameric structures primarily composed of two NR1 and two NR2 subunits. The NR2 subunit is further subdivided into four individual subtypes: NR2A, NR2B, NR2C, and NR2D, which are differentially distributed throughout the brain. Antagonists of NMDA receptors, in particular NR2B, have been investigated as therapeutic agents for the treatment of major depressive disorder (G. Sanacora, 2008, Nature Rev. Drug Disc. 7: 426-437).

The NR2B receptor may be characterized by agonist binding sites in addition to that for glutamate. Non-selective NMDA antagonists such as Ketamine are pore blockers, interfering with the transport of $Ca^{++}$ through the channel. Ketamine has demonstrated rapid and enduring antidepressant properties in human clinical trials as an i.v. drug. Additionally, efficacy was maintained with repeated, intermittent infusions of Ketamine (Zarate et al., 2006, Arch. Gen. Psychiatry 63: 856-864). This class, though, has limited therapeutic value because of its CNS side effect profile, which includes dissociative effects.

An allosteric, non-competitive binding site has also been identified in the N-terminal domain of NR2B. Agents which bind selectively at this site, such as Traxoprodil, exhibited a sustained antidepressant response and improved side effect profile in human clinical trials as an i.v. drug (Preskorn et al., 2008, J. Clin. Psychopharmacol., 28: 631-637, and F. S. Menniti, et al., 1998, CNS Drug Reviews, 4, 4, 307-322). However, development of drugs from this class has been typically hindered by low bioavailability and poor pharmacokinetics. Thus, in the treatment of major depressive disorder, there remains an unmet clinical need for the development of effective NR2B-selective antagonists which have a favorable tolerability profile.

NR2B receptor antagonists have been disclosed in PCT publication WO 2009/006437.

The invention provides technical advantages, for example, the compounds are novel and are ligands for the NR2B receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders related to levels of tachykinins or serotonin or both.

One aspect of the invention is a compound of formula I

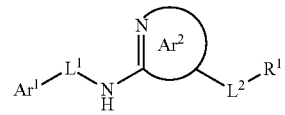

where:

$R^1$ is selected from the group consisting of

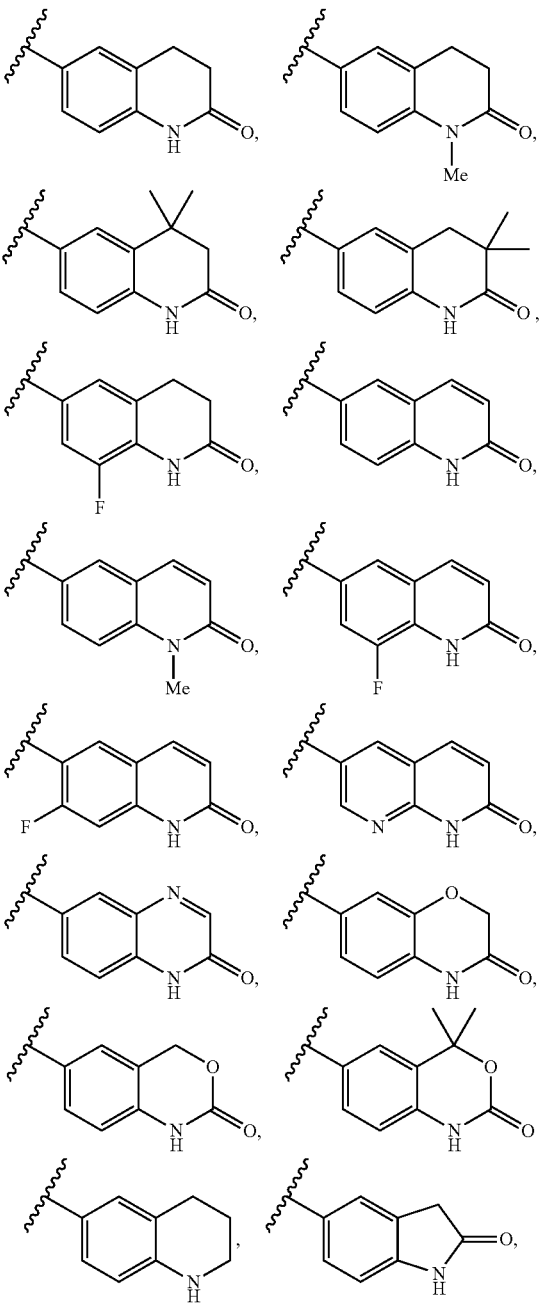

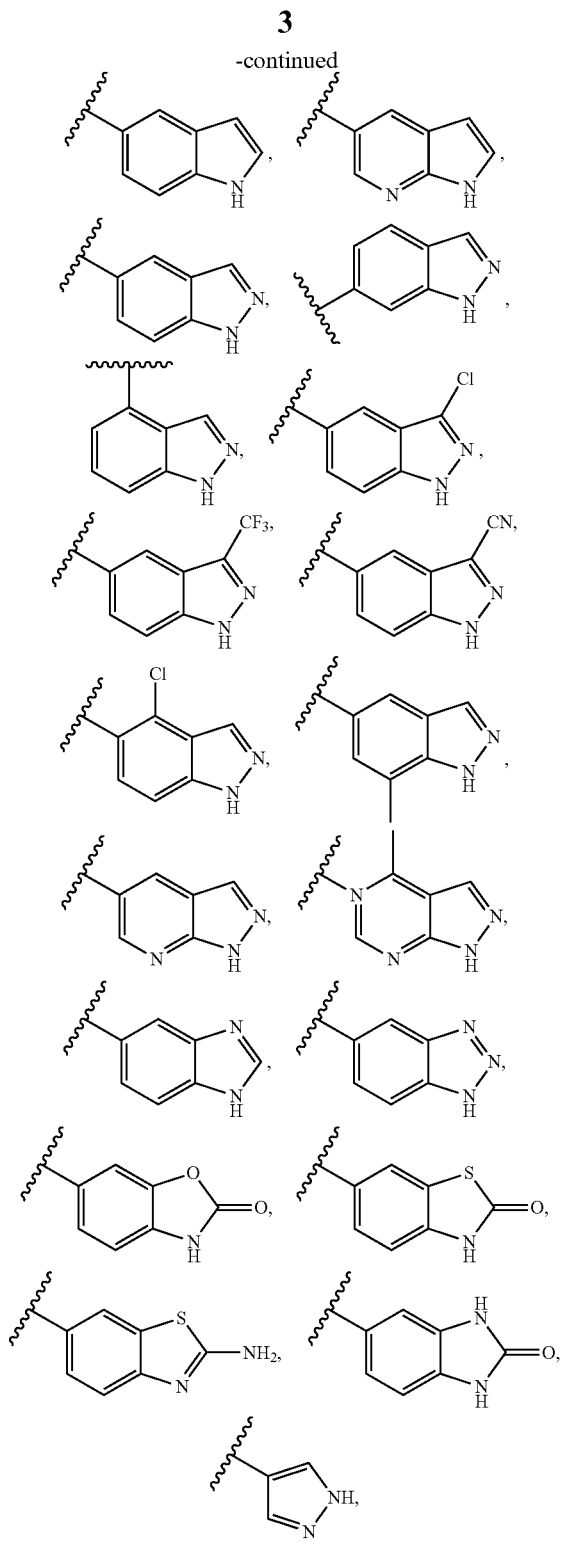
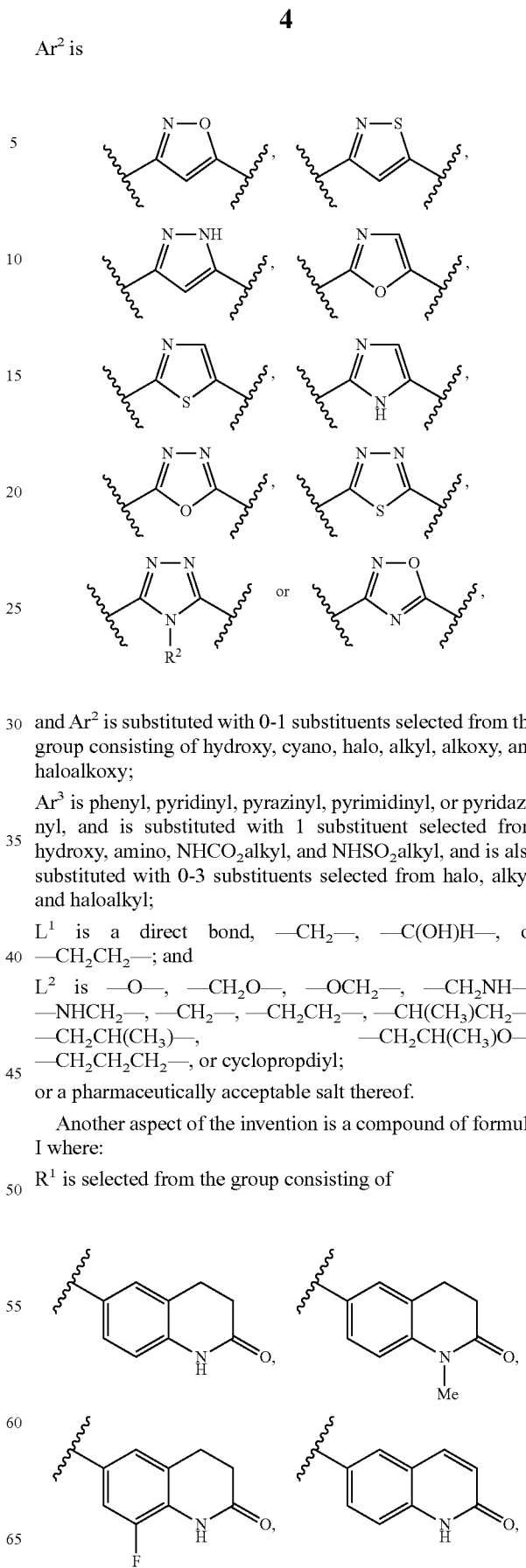

Ar³, ((thiazolyl)amino)phenyl, (pyrimidinyl)amino, and (pyrazolopyrimidinyl)amino;

R² is hydrogen, alkyl, haloalkyl, alkoxy, haloalkoxy, or alkylSO₂;

Ar¹ is phenyl or pyridinyl and is substituted with 0-3 substituents selected from cyano, halo, alkyl, haloalkyl, (alkoxycarbonyl)alkyl, alkoxy, haloalkoxy, dialkylamino, (alkoxycarbonyl)amino, alkylSO₂NH, alkylSO₂, and phenoxy, or Ar¹ is benzodioxolyl or dihydrobenzodioxinyl;

and Ar² is substituted with 0-1 substituents selected from the group consisting of hydroxy, cyano, halo, alkyl, alkoxy, and haloalkoxy;

Ar³ is phenyl, pyridinyl, pyrazinyl, pyrimidinyl, or pyridazinyl, and is substituted with 1 substituent selected from hydroxy, amino, NHCO₂alkyl, and NHSO₂alkyl, and is also substituted with 0-3 substituents selected from halo, alkyl, and haloalkyl;

L¹ is a direct bond, —CH₂—, —C(OH)H—, or —CH₂CH₂—; and

L² is —O—, —CH₂O—, —OCH₂—, —CH₂NH—, —NHCH₂—, —CH₂—, —CH₂CH₂—, —CH(CH₃)CH₂—, —CH₂CH(CH₃)—, —CH₂CH(CH₃)O—, —CH₂CH₂CH₂—, or cyclopropdiyl;

or a pharmaceutically acceptable salt thereof.

Another aspect of the invention is a compound of formula I where:

R¹ is selected from the group consisting of

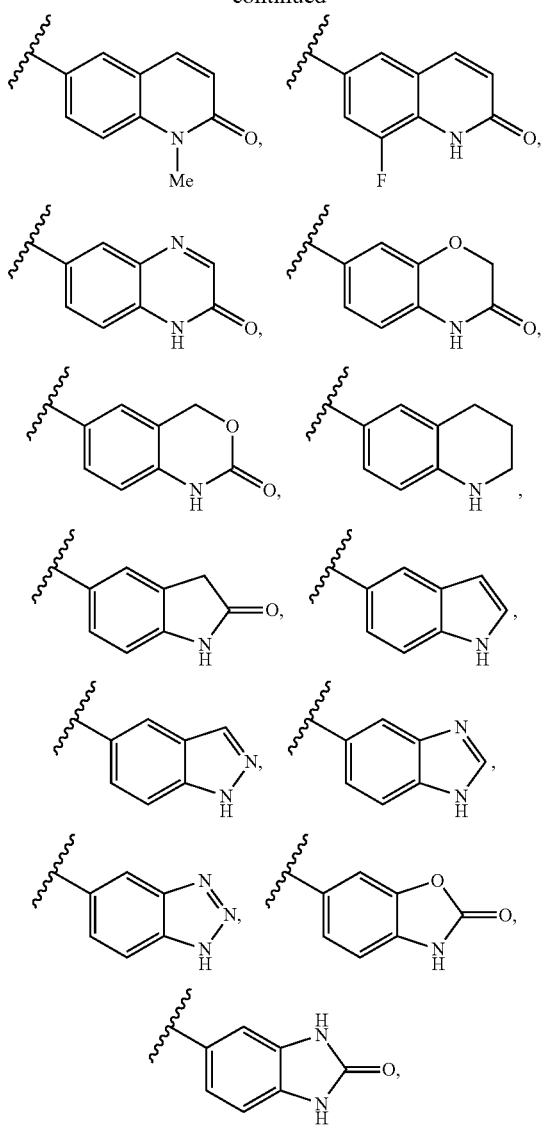

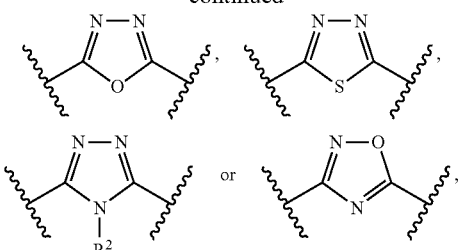

and Ar² is substituted with 0-1 substituents selected from the group consisting of hydroxy, cyano, halo, alkyl, alkoxy, and haloalkoxy;

Ar³ is phenyl, pyridinyl, or pyridazinyl, and is substituted with 1 substituent selected from hydroxy, NHCO₂alkyl, and NHSO₂alkyl, and is also substituted with 0-3 substituents selected from halo, alkyl, and haloalkyl;

L¹ is a direct bond, —CH₂—, or —CH₂CH₂—; and

L² is —CH₂O—, —OCH₂—, —CH₂NH—, —NHCH₂—, —CH₂—, or —CH₂CH₂—;

or a pharmaceutically acceptable salt thereof.

Another aspect of the invention is a compound of formula I where

R¹ is selected from the group consisting of

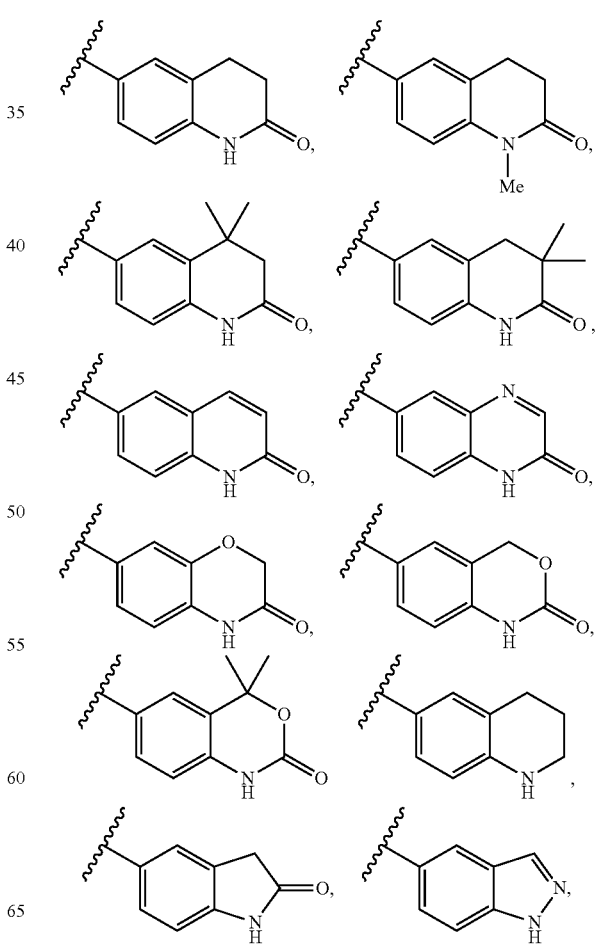

Ar³, and (pyrimidinyl)amino;

R² is hydrogen or alkyl;

Ar¹ is phenyl or pyridinyl and is substituted with 0-3 substituents selected from halo, alkyl, haloalkyl, alkoxy, and haloalkoxy; Ar² is

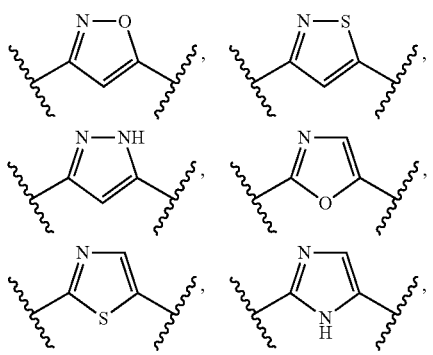

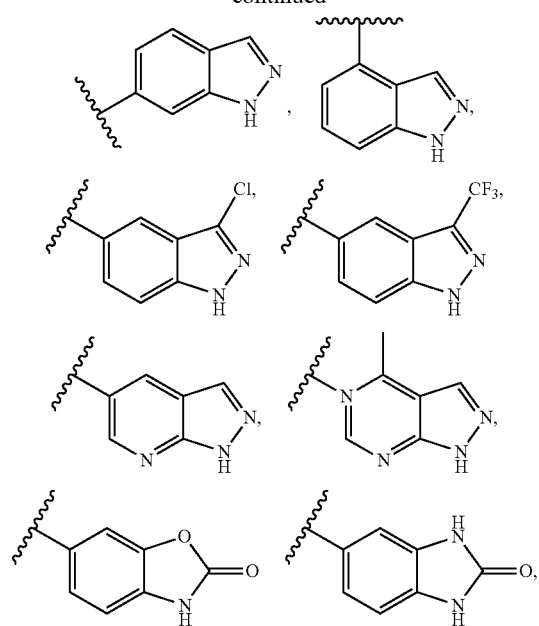

Ar³, (pyrimidinyl)amino, and (pyrazolopyrimidinyl)amino;
R² is hydrogen or alkyl;
Ar¹ is phenyl or pyridinyl and is substituted with 0-3 substituents selected from cyano, halo, alkyl, haloalkyl, (alkoxycarbonyl)alkyl, alkoxy, haloalkoxy, alkoxycarbonyl)amino, alkylSO₂NH, and phenoxy, or Ar¹ is benzodioxolyl or dihydrobenzodioxinyl;
Ar² is

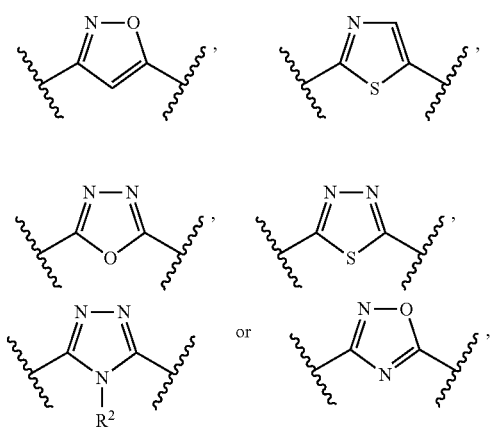

and Ar² is substituted with 0-1 substituents selected from the group consisting of hydroxy, cyano, halo, alkyl, alkoxy, and haloalkoxy;
Ar³ is phenyl, pyridinyl, or pyridazinyl, and is substituted with 1 substituent selected from hydroxyl and amino, and is also substituted with 0-3 halo substituents;
L¹ is a direct bond, —CH₂—, or —C(OH)H—; and
L² is —CH₂O—, —CH₂CH₂—, —CH(CH₃)CH₂—, —CH₂CH(CH₃)O—, or cyclopropdiyl;
or a pharmaceutically acceptable salt thereof.

Another aspect of the invention is a compound of formula I where
R¹ is selected from the group consisting of

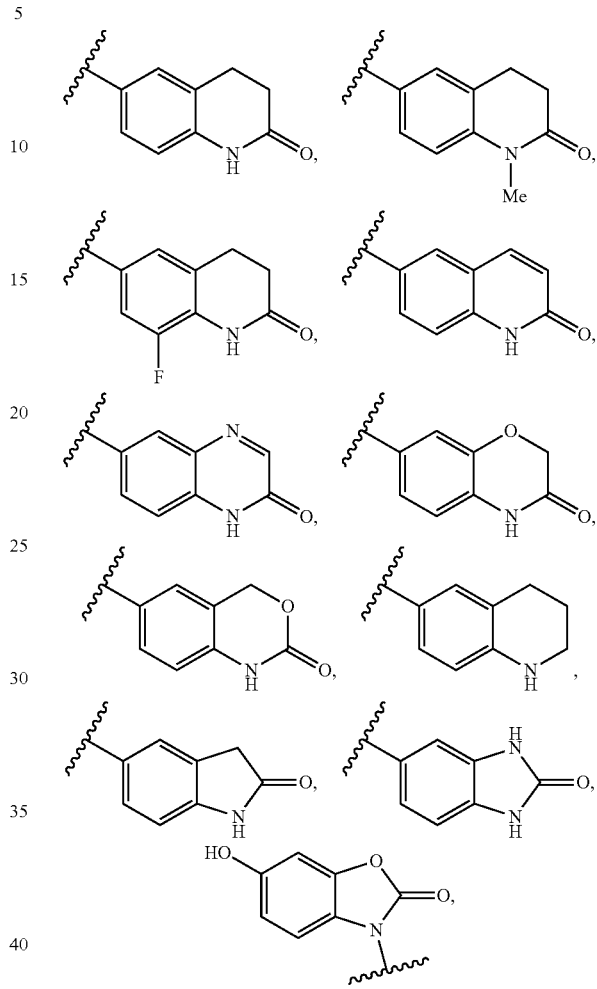

Ar³, and (pyrimidinyl)amino;
Ar¹ phenyl or pyridinyl and is substituted with 0-3 substituents selected from halo, alkyl, haloalkyl, alkoxy, and haloalkoxy;
Ar² is Ar³ is phenyl or pyridazinyl, and is substituted with 1 substituent selected from hydroxy, NHCO₂alkyl, and NHSO₂alkyl, and is also substituted with 0-3 substituents selected from halo, alkyl, and haloalkyl;
L¹ is a direct bond, or —CH₂—; and
L² is —CH₂O—, —CH₂—, or —CH₂CH₂—;
or a pharmaceutically acceptable salt thereof.

Another aspect of the invention is a compound of formula I where
R¹ is selected from the group consisting of

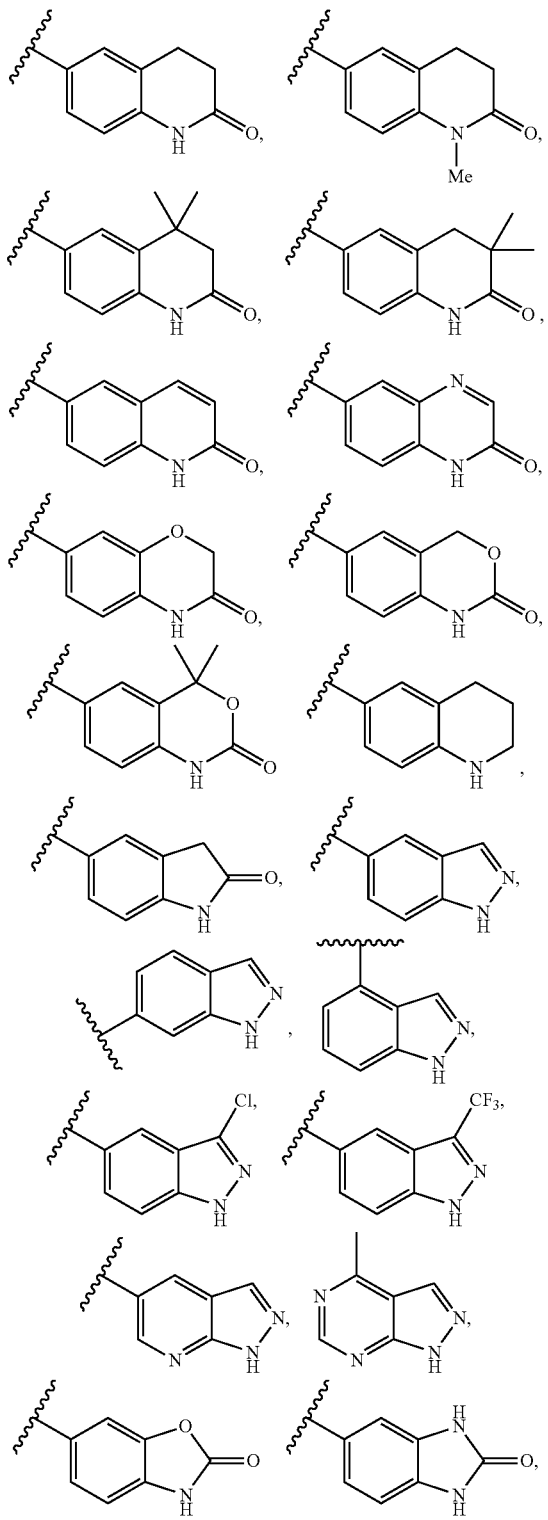

Ar³, (pyrimidinyl)amino, and (pyrazolopyrimidinyl)amino.

Another aspect of the invention is a compound of formula I where Ar¹ is phenyl or pyridinyl and is substituted with 0-3 substituents selected from cyano, halo, alkyl, haloalkyl, (alkoxycarbonyl)alkyl, alkoxy, haloalkoxy, alkoxycarbonyl)amino, alkylSO₂NH, and phenoxy, or Ar¹ is benzodioxolyl or dihydrobenzodioxinyl.

Another aspect of the invention is a compound of formula I where Ar³ is phenyl, pyridinyl, or pyridazinyl, and is substituted with 1 substituent selected from hydroxyl and amino, and is also substituted with 0-3 halo substituents.

Another aspect of the invention is a compound of formula I where L¹ is a direct bond, —CH₂—, or —C(OH)H—.

Another aspect of the invention is a compound of formula I where L² is —CH₂O—, —CH₂CH₂—, —CH(CH₃)CH₂—, —CH₂CH(CH₃)O—, or cyclopropdiyl.

where:

Another aspect of the invention is a compound of formula I where R¹ is selected from the group consisting of

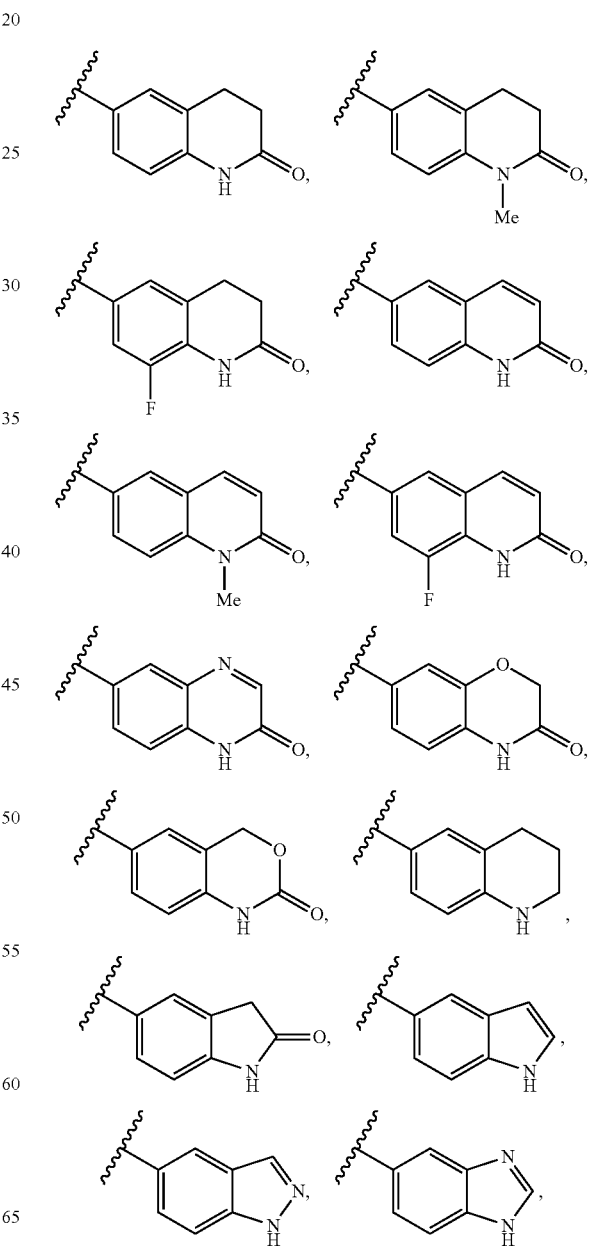

-continued

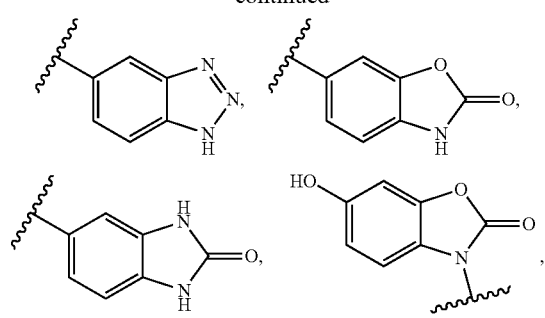

Ar³, or (pyrimidinyl)amino;
R² is hydrogen or alkyl;
Ar¹ phenyl or pyridinyl and is substituted with 0-3 substituents selected from halo, alkyl, haloalkyl, alkoxy, and haloalkoxy;

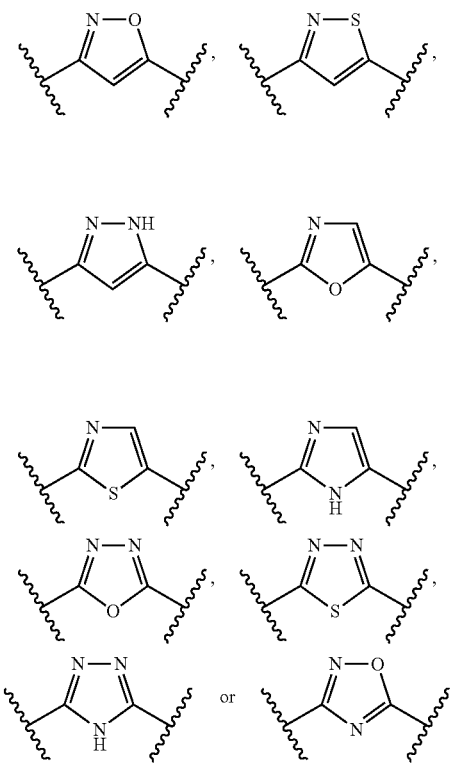

Ar² is and where Ar² is substituted with 0-1 substituents selected from the group consisting of hydroxy, cyano, halo, alkyl, alkoxy, and haloalkoxy;
Ar³ is phenyl, pyridinyl, or pyridazinyl, and is substituted with 1 substituent selected from hydroxy, NHCO₂alkyl, or NHSO₂alkyl, and is also substituted with 0-3 substituents selected from halo, alkyl, and haloalkyl;
L¹ is a direct bond, —CH₂—, or —CH₂CH₂—; and
L² is —CH₂O—, —OCH₂—, —NHCH₂—, —CH₂NH—, —CH₂—, or —CH₂CH₂—;
or a pharmaceutically acceptable salt thereof.

Another aspect of the invention is a compound of formula I
where
R¹ is selected from the group consisting of

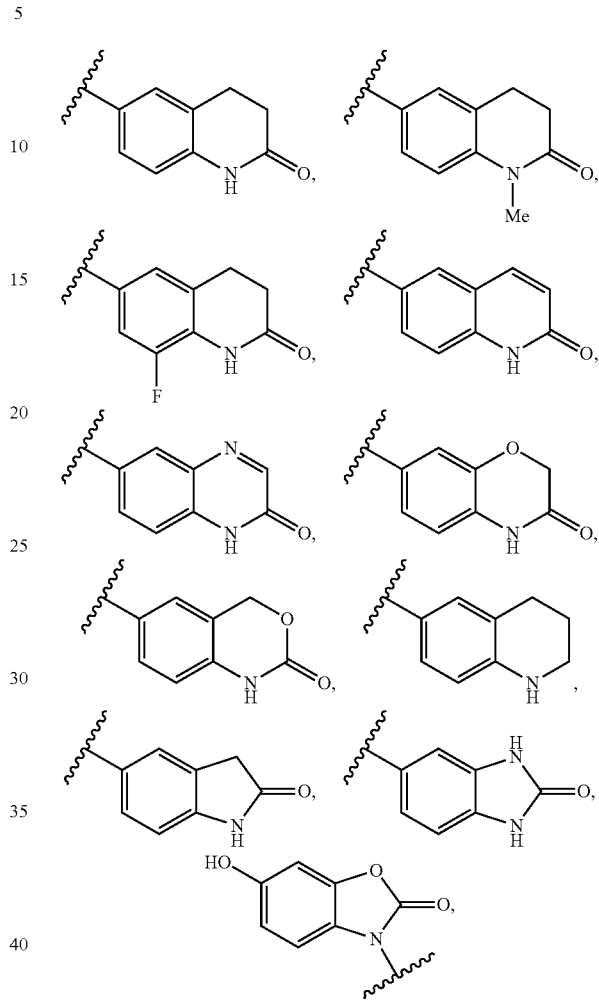

Ar³, or (pyrimidinyl)amino;
Ar¹ phenyl or pyridinyl and is substituted with 0-3 substituents selected from halo, alkyl, haloalkyl, alkoxy, and haloalkoxy;
Ar² is

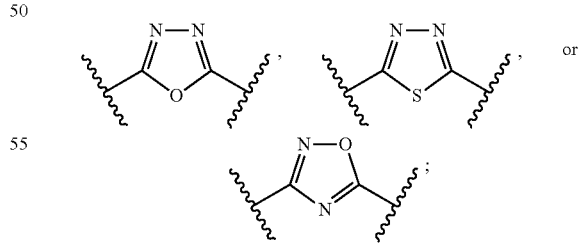

Ar³ is phenyl or pyridazinyl, and is substituted with 1 substituent selected from hydroxy, NHCO₂alkyl, or NHSO₂alkyl, and is also substituted with 0-3 substituents selected from halo, alkyl, and haloalkyl;
L¹ is a direct bond, or —CH₂—; and
L² is —CH₂O—, —CH₂—, or —CH₂CH₂—;
or a pharmaceutically acceptable salt thereof.

Another aspect of the invention is a compound of formula I where
Ar² is

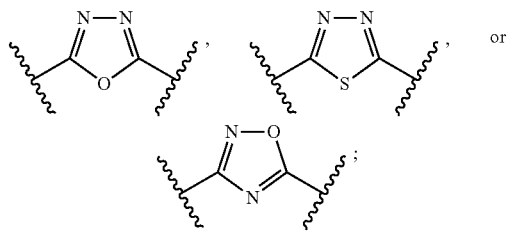

L¹ is a direct bond, or —CH₂—; and L² is —CH₂O—, —CH₂—, or —CH₂CH₂—; or a pharmaceutically acceptable salt thereof.

Another aspect of the invention is a compound of formula I where
Ar² is

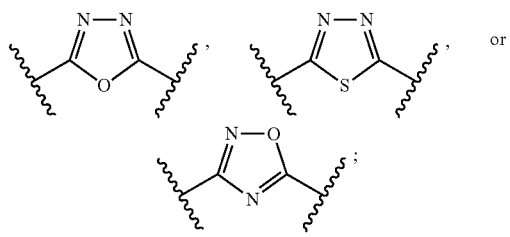

or a pharmaceutically acceptable salt thereof.

Another aspect of the invention is a compound of formula I where L¹ is a direct bond, or —CH₂—; and L² is —CH₂O—, —CH₂—, or —CH₂CH₂—; or a pharmaceutically acceptable salt thereof.

For a compound of formula I, the scope of any instance of a variable substituent, including R¹, R², Ar¹, Ar², Ar³ L¹, and L² can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The compounds include all tautomeric forms. For example, Ar² substituted with 1 hydroxy adjacent to a nitrogen atom would include the keto tautomer.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include ¹³C and ¹⁴C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

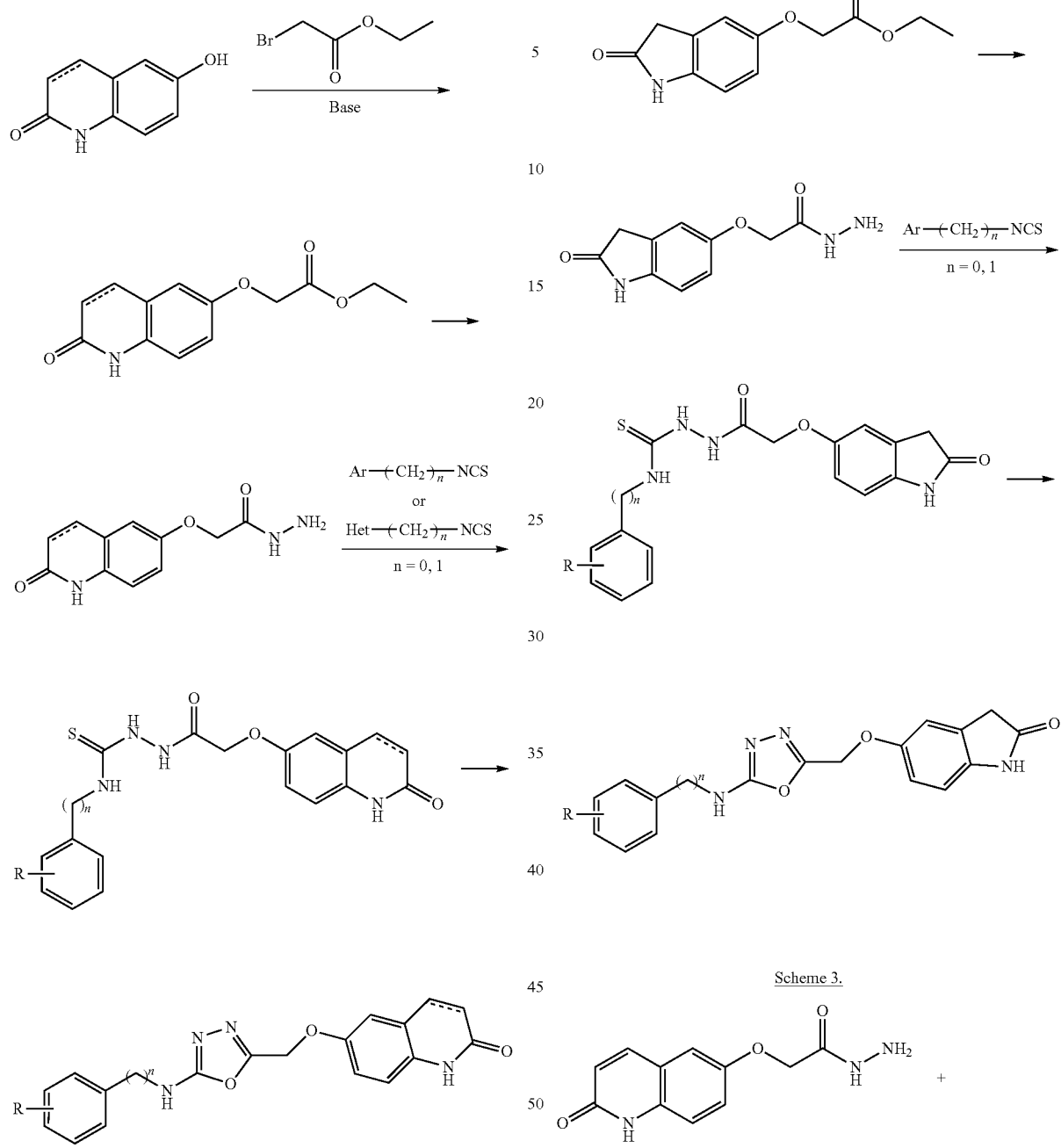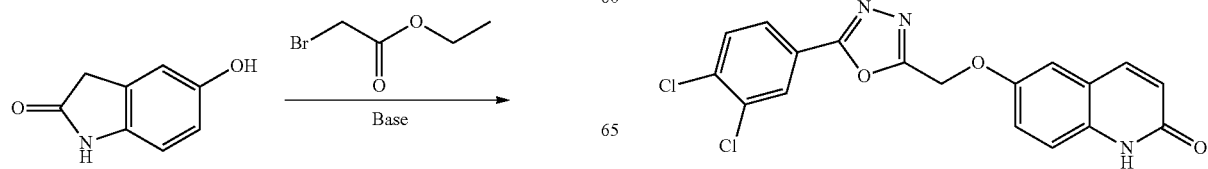

Scheme 4.
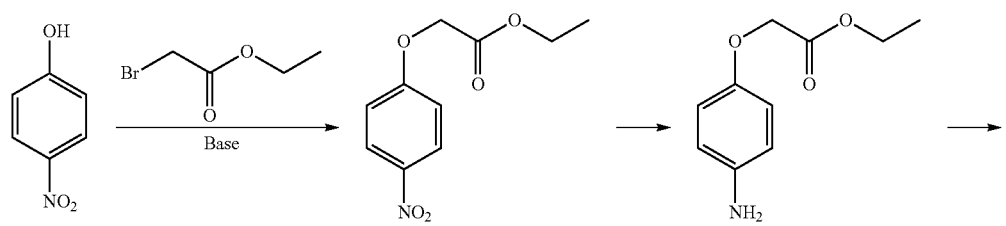
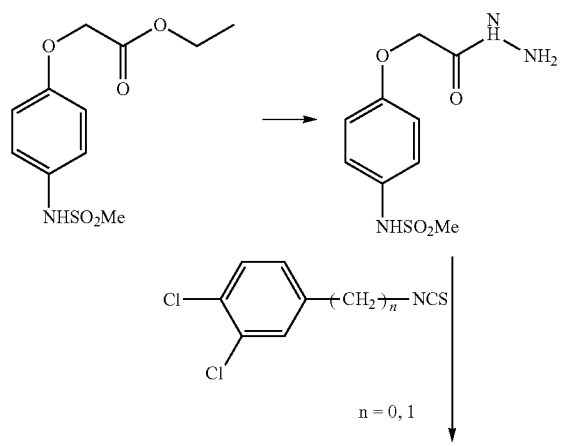
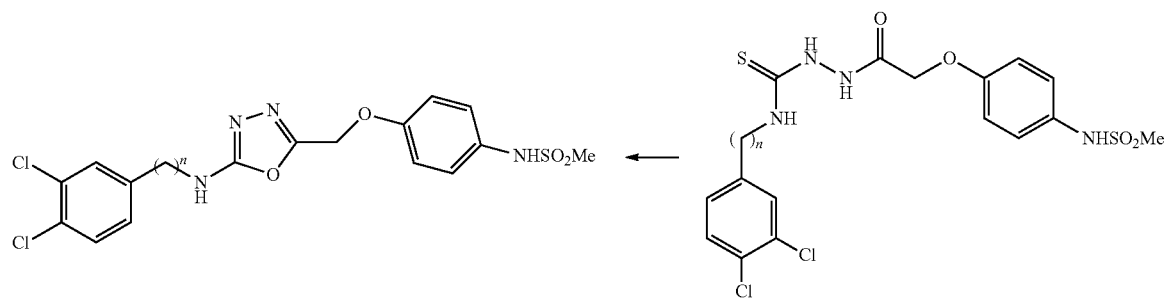
Scheme 5.
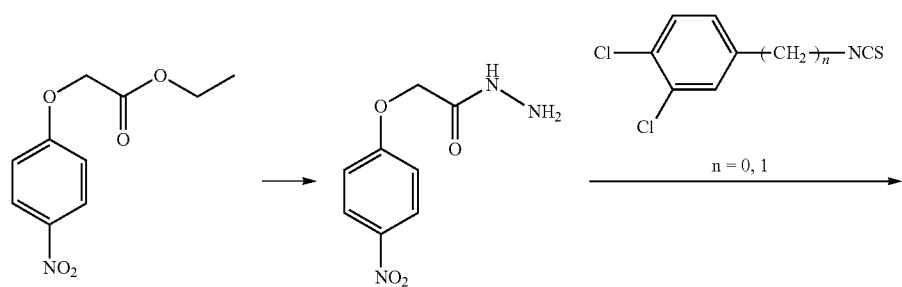

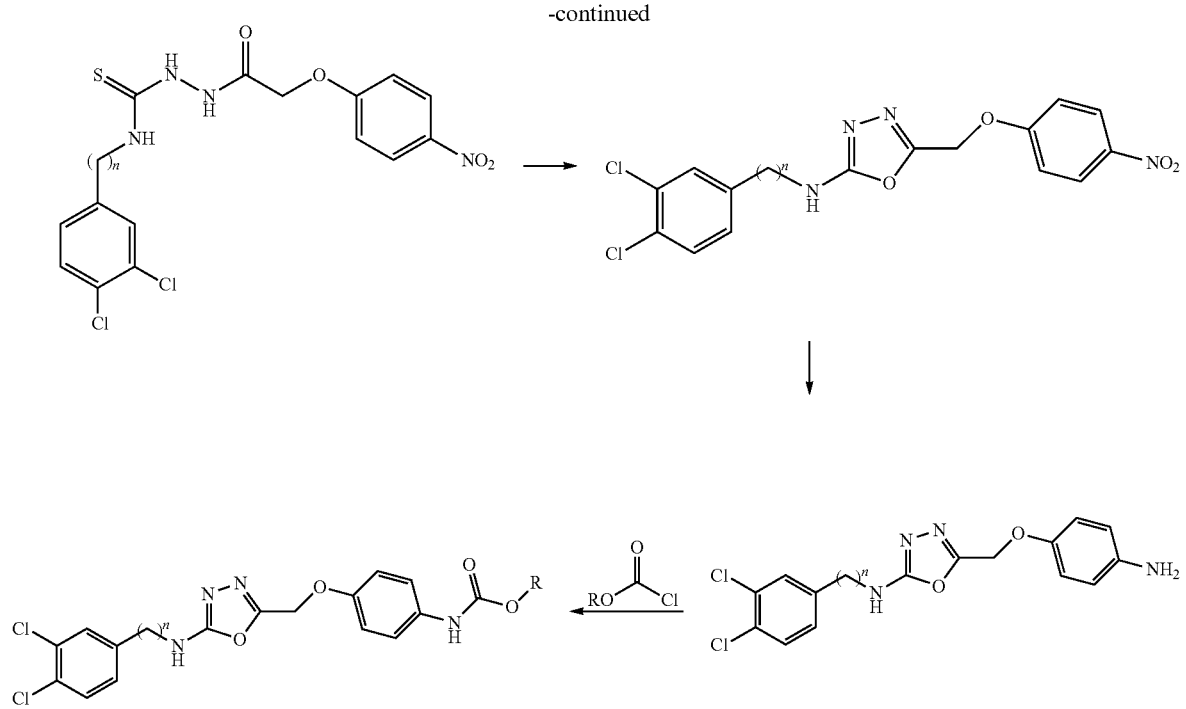
Scheme 6.
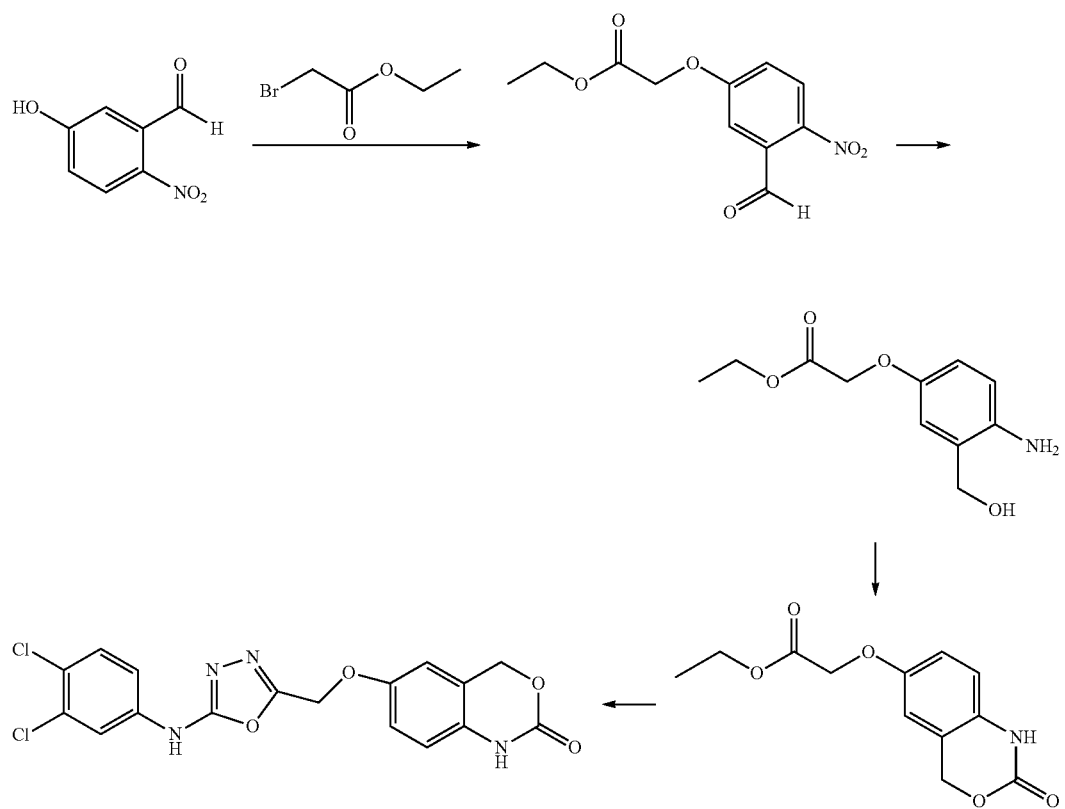

Scheme 7.
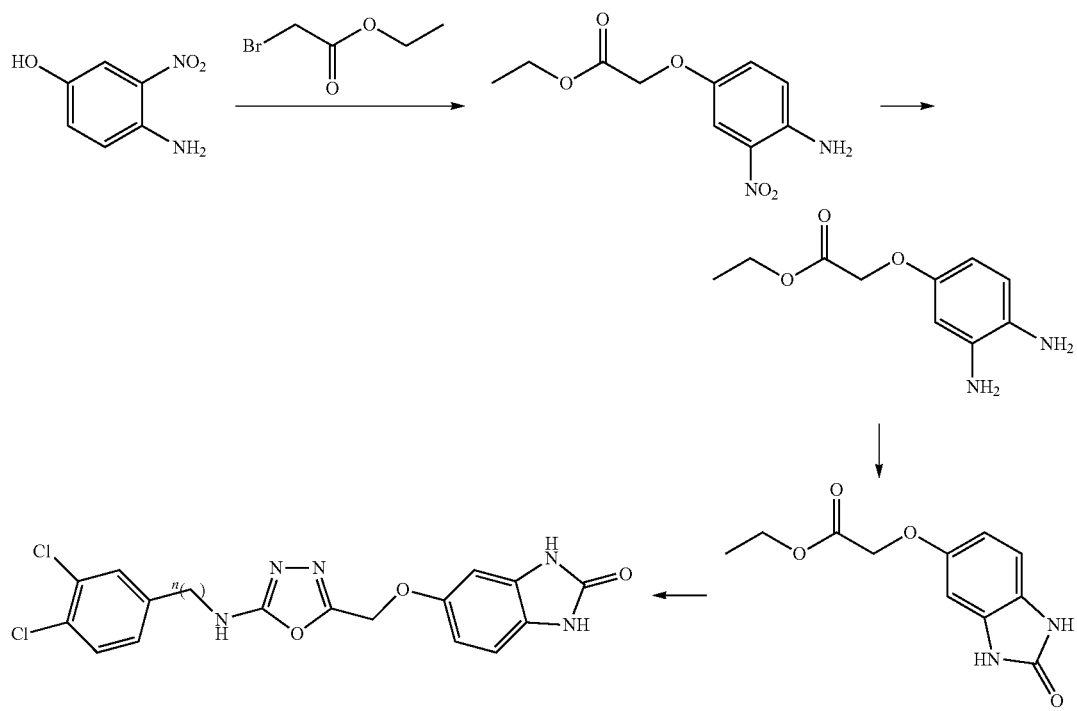
Scheme 8.
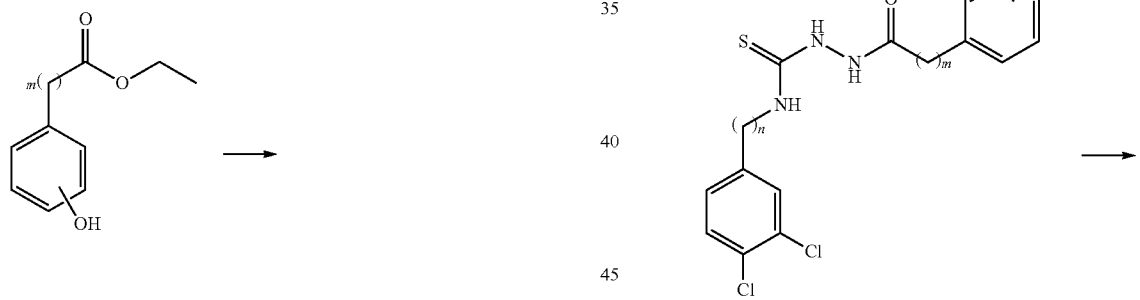
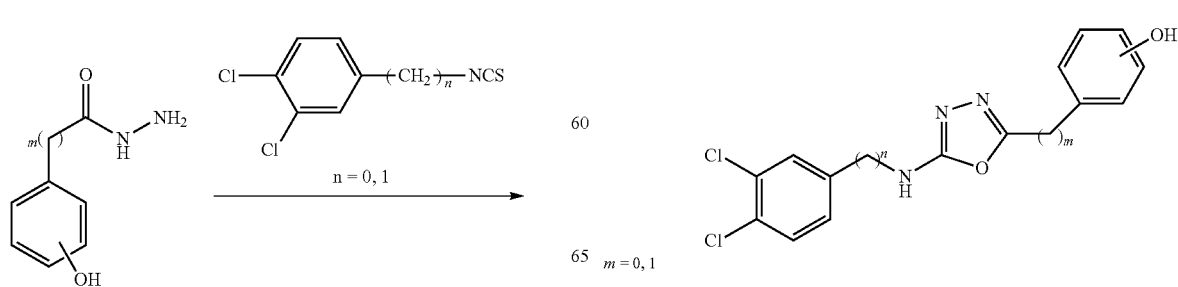
m = 0, 1

Scheme 9.

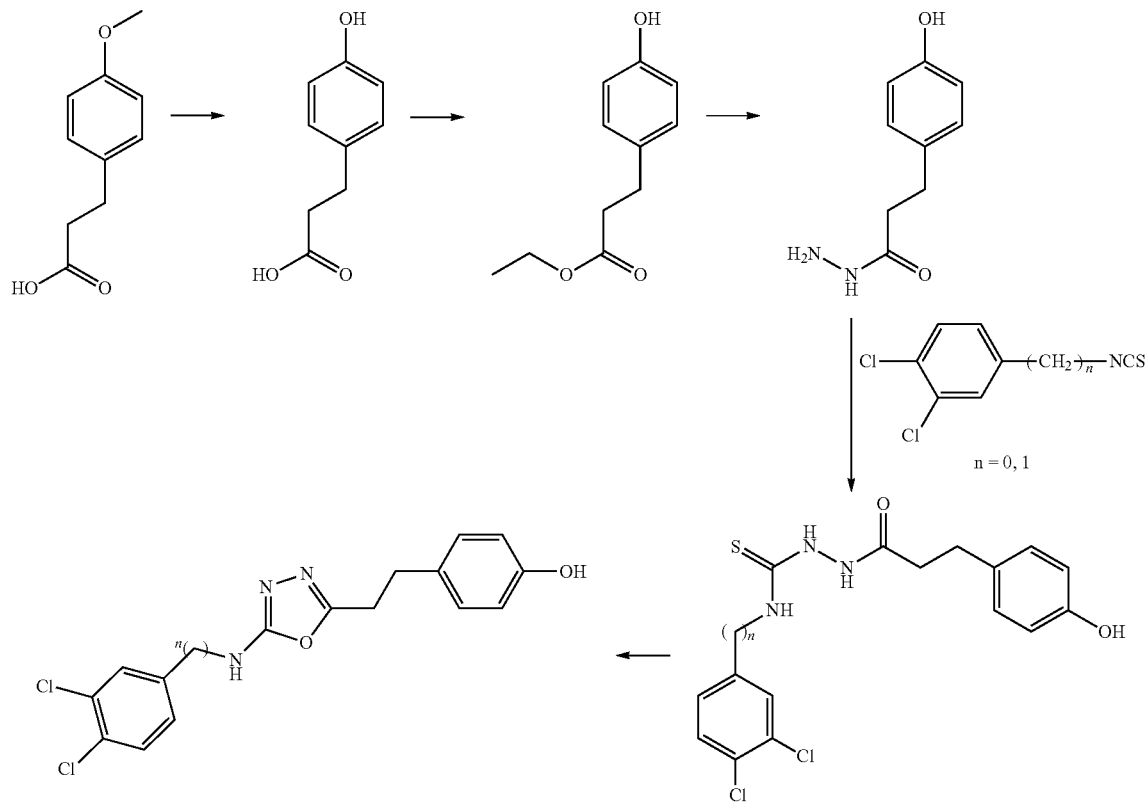

Biological Methods

Electrophysiology NMDA Receptor Experiments.

Stage V and VI oocytes were surgically removed from the ovaries of large, well-fed and healthy *Xenopus laevis* anesthetized with 3-amino-benzoic acid ethyl ester (3 gm/l). Clusters of isolated oocytes were incubated with 292 U/ml Worthington (Freehold, N.J.) type IV collagenase or 1.3 mg/ml collagenase (Life Technologies, Gaithersburg, Md.; 17018-029) for 2 hr in $Ca^{2+}$-free solution comprised of (in mM) 115 NaCl, 2.5 KCl, and 10 HEPES, pH 7.5, with slow agitation to remove the follicular cell layer. Oocytes were then washed in the same solution supplemented with 1.8 mM $CaCl_2$ and maintained in Barth's solution comprised of (in mM): 88 NaCl, 1 KCl, 2.4 $NaHCO_3$, 10 HEPES, 0.82 $MgSO_4$, 0.33 $Ca(NO_3)_2$, and 0.91 $CaCl_2$ and supplemented with 100 μg/ml gentamycin, 10 μg/ml streptomycin, and 10 μg/ml penicillin. Oocytes were manually defolliculated and injected within 24 hrs of isolation with 3-5 ng of human GluN1 subunit cRNA and 7-10 ng of human GluN2 cRNA subunit in a 50 nl volume, and incubated in Barth's solution at 18° C. for 2-7 d. Glass injection pipettes had tip sizes ranging from 10-20 microns, and were backfilled with mineral oil. cRNA was synthesized from linearized template cDNA for rat glutamate receptor subunits according to manufacturer specifications (Ambion).

Two electrode voltage-clamp recordings were made 2-7 days post-injection. Oocytes were placed in a dual-track plexiglass recording chamber with a single perfusion line that splits in a Y-configuration to perfuse two oocytes. Dual recordings were made at room temperature (23° C.) using two Warner OC725B two-electrode voltage clamp amplifiers, arranged as recommended by the manufacturer. Glass microelectrodes (1-10 Megaohms) were filled with 300 mM KCl (voltage electrode) or 3 M KCl (current electrode). The bath clamps communicated across silver chloride wires placed into each side of the recording chamber, both of which were assumed to be at a reference potential of 0 mV. Oocytes were perfused with a solution comprised of (in mM) 90 NaCl, 1 KCl, 10 HEPES, 10 EDTA and 0.5 $BaCl_2$; pH 7.4, adjusted by addition of NaOH. Oocytes were recorded under voltage clamp at −40 mV. Final concentrations for glutamate and glycine were 50 μM and 30 μM, respectively. Concentration-response curves for experimental compounds were obtained by applying in successive fashion maximal glutamate/glycine, followed by glutamate/glycine plus variable concentrations of experimental compounds. Dose response curves consisting of four to eight concentrations were obtained in this manner. The baseline leak current at −40 mV was measured before and after recording, and the full recording linearly corrected for any change in leak current. The level of inhibition by applied experimental compounds was expressed as a percent of the initial glutamate response, and averaged together across oocytes from multiple experiments. Results were pooled, and the average percent responses at antagonist concentrations were fit by the equation, Percent Response= $(100-\text{minimum})/(1+([\text{conc}]/\text{IC}50)^{nH})+\text{minimum}$ where minimum is the residual percent response in saturating concentration of the experimental compounds, IC50 is the concentration of antagonist that causes half of the achievable inhibition, and nH is a slope factor describing steepness of the inhibition curve. Minimum was constrained to be greater than For NMDA receptor subtype selectivity experiments human GluN1/GluN2A, GluN1/GluN2C, and GluN1/

GluN2D cRNAs were expressed in *Xenopus laevis* as described above. Here, 10 μM concentrations of the antagonist was perfused with 50 μM glutamate and 30 μM glycine onto the oocyte for two min and the remaining current in the presence of the antagonist was compared to the maximal current obtained with 50 μM glutamate and 30 μM glycine alone (defined as 100%). When $IC_{50}$ determinations were made against other NMDA receptor subtypes the protocol as described above was followed. Activity is illustrated in the following tables. according to the following: +0-200 nM; ++201-1000 nM; +++1000-10000 nM; ++++>10000 nM.

| Example Number | hNR2B $IC_{50}$ (nM) | Activity |
|---|---|---|
| 1 | 715 | |
| 2 | >10000 | |
| 3 | 7300 | |
| 4 | 265 | ++ |
| 5 | 57 | + |
| 6 | 112 | + |
| 7 | | ++ |
| 8 | | + |
| 9 | | + |
| 10 | | + |
| 11 | 55 | + |
| 12 | | + |
| 13 | | + |
| 14 | | ++ |
| 15 | | ++++ |
| 16 | | ++ |
| 17 | 80 | + |
| 18 | | ++++ |
| 19 | | + |
| 20 | 476 | ++ |
| 21 | | + |
| 22 | | + |
| 23 | | + |
| 24 | 7240 | +++ |
| 25 | | ++++ |
| 26 | | + |
| 27 | | + |
| 28 | | + |
| 29 | | + |
| 30 | 19 | + |
| 31 | | ++++ |
| 32 | 2120 | +++ |
| 33 | | ++++ |
| 34 | | +++ |
| 35 | 884 | ++ |
| 36 | 1740 | +++ |
| 37 | 1010 | +++ |
| 38 | 3450 | +++ |
| 39 | | +++ |
| 40 | | +++ |
| 41 | | ++++ |
| 42 | | ++ |
| 43 | | +++ |
| 44 | | +++ |
| 45 | | ++ |
| 46 | | +++ |
| 47 | | ++ |
| 48 | | ++ |
| 49 | 18 | + |
| 50 | | + |
| 51 | | + |
| 52 | | + |
| 53 | 4040 | +++ |
| 54 | | ++++ |
| 55 | 542 | ++ |
| 56 | | ++++ |
| 57 | | ++++ |
| 58 | 830 | ++ |
| 59 | | + |
| 60 | | ++++ |
| 61 | | ++++ |
| 62 | | +++ |
| 63 | | +++ |
| 64 | 328 | ++ |
| 65 | | + |
| 66 | | ++++ |
| 67 | | ++ |
| 68 | | ++ |
| 69 | | +++ |
| 70 | | +++ |
| 71 | | +++ |
| 72 | | +++ |
| 73 | | + |
| 74 | | + |
| 75 | | +++ |
| 76 | | + |
| 77 | | ++ |
| 78 | | +++ |
| 79 | | ++ |
| 80 | | +++ |
| 81 | | +++ |
| 82 | | ++ |
| 83 | | +++ |
| 84 | | ++++ |
| 85 | | +++ |
| 86 | | ++ |
| 87 | | + |
| 88 | | + |
| 89 | | ++ |
| 90 | | ++ |
| 91 | | +++ |
| 92 | | + |
| 93 | | ++ |
| 94 | | ++ |
| 95 | | +++ |
| 96 | | ++ |
| 97 | | +++ |
| 98 | | + |
| 99 | | ++ |
| 100 | | +++ |
| 101 | | + |
| 102 | | + |
| 103 | | ++ |
| 104 | | + |
| 105 | | + |
| 106 | | + |
| 107 | | + |
| 108 | | + |
| 109 | | + |
| 110 | | + |
| 111 | | + |
| 112 | | + |
| 113 | | + |
| 114 | | + |
| 115 | | + |
| 116 | | +++ |
| 117 | | ++++ |
| 118 | | +++ |
| 119 | | ++ |
| 120 | | ++++ |
| 121 | | ++++ |
| 122 | | ++++ |
| 123 | | +++ |
| 124 | | +++ |
| 125 | | ++ |
| 126 | | ++ |
| 127 | | ++ |
| 128 | 61 | |
| 129 | | + |
| 130 | | + |
| 131 | | + |
| 132 | | + |
| 133 | | + |
| 134 | | + |
| 135 | | + |
| 136 | | + |
| 137 | | + |
| 138 | | + |
| 139 | | + |

| Example Number | hNR2B IC$_{50}$ (nM) | Activity |
|---|---|---|
| 140 | | ++++ |
| 141 | | +++ |
| 142 | 4680 | +++ |
| 143 | | ++++ |
| 144 | | + |
| 145 | | +++ |
| 146 | 230 | ++ |
| 147 | | +++ |
| 148 | | ++++ |
| 149 | | +++ |
| 150 | | +++ |
| 151 | | + |
| 152 | 48 | + |
| 153 | | + |
| 154 | 9.5 | |
| 155 | | + |
| 156 | 390 | |
| 157 | | ++++ |
| 158 | | ++++ |
| 159 | | ++++ |
| 160 (Rac) | | ++ |
| 161 | | ++++ |
| 162 Rac | | ++ |
| 163 Rac | | ++ |
| 164 | | +++ |
| 165 | | +++ |
| 166 | | + |
| 167 | 300 | ++ |
| 168 Rac | | +++ |
| 169 Rac | | ++++ |
| 170 Rac | | +++ |
| 171 Rac | | +++ |
| 172 rac | | +++ |
| 173 rac | 345 | ++ |
| 174 isomer A | | ++ |
| 175 isomer B | | +++ |
| 176 Isomer A | | + |
| 177 Isomer B | | +++ |
| 178 | | ++ |
| 179 | | ++ |
| 180 | | +++ |
| 181 | 145 | + |
| 182 | | +++ |
| 183 | | +++ |
| 184 | | +++ |
| 185 | | +++ |
| 186 | | ++ |
| 187 | | ++++ |
| 188 | | ++++ |
| 189 | | +++ |
| 190 | 168 | + |
| 191 | | + |
| 192 | | +++ |
| 193 | | +++ |
| 194 | >10000 | |
| 195 | | ++++ |
| 196 | | ++++ |
| 197 | | ++++ |
| 198 | | +++ |
| 199 | | ++++ |
| 200 | 320 | ++ |
| 201 | 470 | ++ |
| 202 | | ++++ |
| 203 | | ++++ |
| 204 | | ++ |
| 205 | | ++++ |
| 206 | | +++ |
| 207 | | + |
| 208 | 11 | + |
| 209 | 19 | + |
| 210 | | + |
| 211 | | + |
| 212 | | ++ |
| 213 | | +++ |
| 214 | | ++ |
| 215 | | + |
| 216 | | ++ |
| 217 | | ++++ |
| 218 | | |
| 219 | | + |
| 220 | | |
| 221 | | +++ |
| 222 | | +++ |
| 223 | | ++ |
| 224 | | ++ |
| 225 | | ++ |
| 226 | | ++ |
| 227 | | ++++ |
| 228 | | +++ |
| 229 | | ++++ |
| 230 | | + |
| 231 | | +++ |
| 232 | | +++ |
| 233 | | + |
| 234 | | +++ |
| 235 | 44 | |
| 236 | | ++ |
| 237 | | + |
| 238 | | + |
| 239 | 3600 | |
| 240 | 266 | |
| 241 | 30 | + |
| 242 | | + |
| 243 | | + |
| 244 | | + |
| 245 | | + |
| 246 | 635 | ++ |
| 247 | | + |
| 248 | | ++ |
| 249 | | ++ |
| 250 | | ++ |
| 251 | 9400 | +++ |
| 252 | 24000 | |
| 253 | 321 | |
| 254 | 193 | + |
| 255 | | + |
| 256 | | + |
| 257 | 10 | + |
| 258 | | + |
| 260 | | + |
| 261 | | + |
| 262 | | +++ |
| 263 | | +++ |
| 264 | | + |
| 265 | | + |
| 266 | | ++++ |
| 267 | | + |
| 268 | | + |
| 269 | | + |
| 270 | | +++ |
| 271 | | + |
| 272 | | + |
| 273 | | +++ |
| 274 | | + |
| 275 | | + |
| 276 | 24 | |
| 277 | 104 | |

-continued

| Example Number | hNR2B IC$_{50}$ (nM) | Activity |
|---|---|---|
| 278 | 90 | + |
| 279 |  | + |
| 280 |  | + |
| 281 |  | + |
| 282 | 290 | ++ |
| 283 |  | ++ |
| 284 | 20000 |  |
| 285 | 5000 |  |
| 286 | 3000 |  |
| 287 | 3800 |  |
| 288 | >10000 |  |
| 289 | 2400 |  |
| 290 | 4800 |  |
| 291 | 1200 |  |

Pharmaceutical Compositions and Methods of Treatment

Compounds of formula I can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment of depression, Alzheimer's disease, Parkinson's disease, or neuropathic pain, which comprises administering to a patient a therapeutically affective amount of a compound of formula I.

Another aspect of the invention is a method for the treatment of depression which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is a method for the treatment of neuropathic pain which comprises administering to a patient a therapeutically affective amount of a compound of formula I.

Another aspect of the invention is a method for the treatment of Parkinson's disease which comprises administering to a patient a therapeutically affective amount of a compound of formula I.

Another aspect of the invention is the use of a compound of formula I in the manufacture of a medicament for the treatment of neurological or psychiatric disorders.

Another aspect of the invention is the use of a compound of formula I in the manufacture of a medicament for the treatment of depression, Alzheimer's disease, Parkinson's disease, neuropathic pain, or Parkinson's disease.

Another aspect of the invention is the use of a compound of formula I in the manufacture of a medicament for the treatment of depression.

Another aspect of the invention is the use of a compound of formula I in the manufacture of a medicament for the treatment of Alzheimer's disease.

Another aspect of the invention is the use of a compound of formula I in the manufacture of a medicament for the treatment of Parkinson's disease.

Another aspect of the invention is the use of a compound of formula I in the manufacture of a medicament for the treatment of neuropathic pain.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The variables (e.g. numbered "R" substituents) used to describe some of the exemplified compounds are intended only to illustrate the compounds and are not to be confused with variables used in the claims or in other sections of the specification.

Intermediates

Ethyl 2-(2-oxo-1,2,3,4-tetrahydroquinolin-6-yloxy)acetate

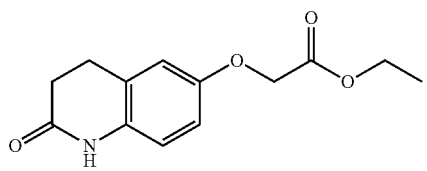 [SMILES: CCOC(=O)COc1ccc2c(c1)CCC(=O)N2]

To a stirred solution of 6-hydroxy-3,4-dihydroquinolin-2 (1H)-one (2.5 g, 15.3 mmol) in dry DMF (10 ml) was added potassium carbonate (4.2 g, 30.3 mmol) and ethyl bromoacetate (2.4 g, 14.3 mmol). The reaction was stirred at room temperature for 2 h. Completion of the reaction was monitored by TLC. Solvent was removed under vacuum. The residue was dissolved in ethyl acetate (150 mL), washed with water (20 mL), brine (20 mL), and dried over sodium sulfate. The organic layer was concentrated under vacuum to afford 2.7 g of crude material which was purified by silica gel flash chromatography (24 g, 2% methanol in chloroform) to afford 2.8 g (73%) of ethyl 2-(2-oxo-1,2,3,4-tetrahydroquinolin-6-yloxy)acetate as a white solid. 1H NMR: 400 MHz, DMSO-d6: δ 1.21 (t, J=7.20 Hz, 3H), 2.40 (t, J=7.20 Hz, 2H), 2.83 (t, J=8.00 Hz, 2H), 4.17 (q, J=7.20 Hz, 2H), 4.69 (s, 2H), 6.71-6.80 (m, 3H), 9.92 (s, 1H). LCMS: RT 1.31 min. LCMS (ES-API), m/z 250.0 (M+H).

2-(2-oxo-1,2,3,4-tetrahydroquinolin-6-yloxy)acetohydrazide

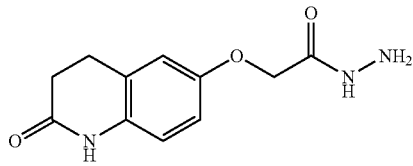 [SMILES: NNC(=O)COc1ccc2c(c1)CCC(=O)N2]

To a stirred solution of ethyl 2-(2-oxo-1,2,3,4-tetrahydroquinolin-6-yloxy)acetate (0.4 g, 1.7 mmol) in ethanol (10 mL), hydrazine hydrate (0.9 g, 17 mmol) was added and the reaction was heated at 80° C. for two hours. The solid which formed was filtered and dried. 2-(2-oxo-1,2,3,4-tetrahydroquinolin-6-yloxy)acetohydrazide was obtained as a white solid (0.25 g, 66%) and was used in the next step without further purification. 1H NMR: 400 MHZ, DMSO-d6: δ 2.40 (t, J=7.20 Hz, 2H), 2.83 (t, J=8.40 Hz, 2H), 4.31 (d, J=4.00 Hz, 2H), 4.41 (s, 1H), 6.76 (d, J=2.00 Hz, 2H), 6.82 (s, 1H), 9.26 (s, 1H), 9.91 (s, 1H). LCMS: RT 0.607 min. LCMS (ES-API), m/z 236.2 (M+H).

Ethyl 2-((2-oxoindolin-5-yl)oxy)acetate

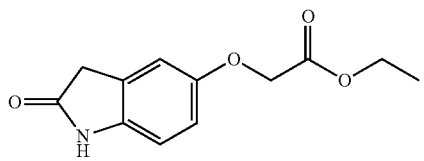 [SMILES: CCOC(=O)COc1ccc2c(c1)CC(=O)N2]

To a stirred solution of 5-hydroxyindolin-2-one (1 g, 6.70 mmol) in 2-Propanol (10 mL) was added DBU (1.52 mL, 10.06 mmol) and ethyl bromoacetate (1.12 mL, 10.06 mmol) at room temperature. The reaction mixture was refluxed at 80° C. for 12 h. After completion of the reaction as monitored by TLC, the reaction mixture was concentrated and water (100 mL) was added. The solid which precipitated was filtered and dried to yield ethyl 2-((2-oxoindolin-5-yl)oxy)acetate as an off white solid (0.75 g, 47.6%) LCMS: RT 0.67 min. LCMS (ES-API), m/z 236.0 (M+H).

2-((2-oxoindolin-5-yl)oxy)acetohydrazide

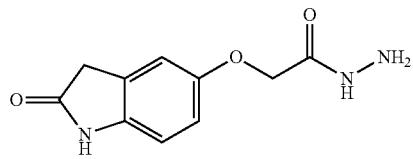 [SMILES: NNC(=O)COc1ccc2c(c1)CC(=O)N2]

By a procedure analogous to that used for the synthesis of 2-(2-oxo-1,2,3,4-tetrahydroquinolin-6-yloxy)acetohydrazide, 2-((2-oxoindolin-5-yl)oxy)acetohydrazide (0.4 g, 85%) was synthesized. 1H NMR: 400 MHZ, DMSO-d6: δ 3.45 (s, 2H), 4.31 (s, 2H), 4.41 (s, 2H), 6.70-6.79 (m, 2H), 9.28 (s, 1H), 10.20 (s, 1H).

2-((2-oxo-1,2-dihydroquinolin-6-yl)oxy)acetohydrazide

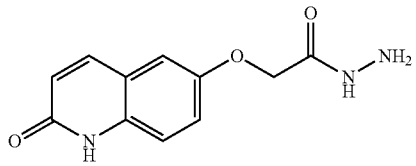 [SMILES: NNC(=O)COc1ccc2[nH]c(=O)ccc2c1]

By a procedure analogous to that used for the synthesis of 2-(2-oxo-1,2,3,4-tetrahydroquinolin-6-yloxy)acetohydrazide, 2-((2-oxo-1,2-dihydroquinolin-6-yl)oxy)acetohydrazide (0.25 g, 66%) was synthesized. 1H NMR: 400 MHZ, DMSO-d6: δ 4.33 (s, 2H), 4.51 (s, 2H), 6.50 (d, J=9.60 Hz, 1H), 7.21-7.27 (m, 3H), 7.82 (d, J=9.20 Hz, 1H), 9.35 (s, 1H), 11.63 (s, 1H).

Ethyl 2-((2-oxo-2,4-dihydro-1H-benzo[d][1,3]oxazin-6-yl)oxy)acetate

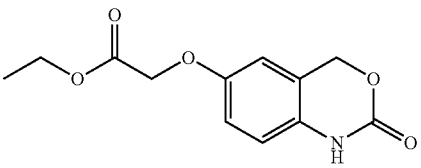 [SMILES: CCOC(=O)COc1ccc2c(c1)COC(=O)N2]

To a solution of ethyl 2-(4-amino-3-(hydroxymethyl)phenoxy)acetate (0.2 g, 0.888 mmol) in THF (5 mL) was added CDI (0.216 g, 1.332 mmol) at 0° C. and stirred at RT for 2 h. The reaction mixture was diluted with water and extracted with ethyl acetate. The organic layer washed with brine, dried over sodium sulfate and concentrated. The crude product was purified by flash chromatography on silica gel using hexane/ethyl acetate as eluent to yield ethyl 2-((2-oxo-2,4-dihydro-1H-benzo[d][1,3]oxazin-6-yl)oxy)acetate (0.03 g, 13%). 1H NMR: 400 MHZ, DMSO-d6: δ 1.22 (t, J=7.20 Hz, 3H), 4.17 (q, J=6.80 Hz, 2H), 4.72 (s, 2H), 5.23 (s, 2H), 6.79-6.86 (m, 3H), 10.01 (s, 1H).

2-((2-oxo-2,4-dihydro-1H-benzo[d][1,3]oxazin-6-yl)oxy)acetohydrazide

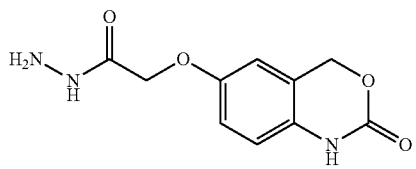 [SMILES: NNC(=O)COc1ccc2c(c1)COC(=O)N2]

By a procedure analogous to the preparation of 2-(2-oxo-1,2,3,4-tetrahydroquinolin-6-yloxy)acetohydrazide, 2-((2-oxo-2,4-dihydro-1H-benzo[d][1,3]oxazin-6-yl)oxy)acetohydrazide (0.56 g, 99%) was synthesized. 1H NMR: 400 MHZ, DMSO-d6: δ 3.90 (s, 2H), 4.43 (s, 2H), 5.23 (s, 2H), 6.80-6.89 (m, 3H), 9.30 (s, 1H).

Ethyl 2-((2-oxo-2,3-dihydro-1H-benzo[d]imidazol-5-yl)oxy)acetate

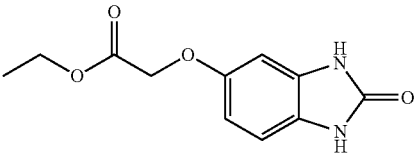 [SMILES: CCOC(=O)COc1ccc2[nH]c(=O)[nH]c2c1]

To a stirred solution of ethyl 2-(3,4-diaminophenoxy)acetate (144 mg, 0.685 mmol) in dry CHCl3 (5 mL) at 0° C., pyridine (0.083 mL, 1.027 mmol) and triphosgene (203 mg, 0.685 mmol) were added and allowed to stir at room temperature for two hours. Completion of the reaction was monitored by LCMS. Solvent was removed under vacuum. Water was added to the residue. The solid which formed was filtered and dried to afford crude ethyl 2-((2-oxo-2,3-dihydro-1H-benzo[d]imidazol-5-yl)oxy)acetate (85 mg, 75% by LCMS) which was used in the next step without further purification. 1H NMR: 400 MHZ, DMSO-d6: δ 1.22 (t, J=7.20 Hz, 3H), 4.18 (q, J=7.20 Hz, 2H), 4.70 (s, 2H), 6.52 (t, J=2.40 Hz, 2H), 6.81 (d, J=9.20 Hz, 1H), 10.40 (s, 1H), 10.51 (s, 1H). LCMS: RT 1.16 min. LCMS (ES-API), m/z 237.0 (M+H).

2-((2-oxo-2,3-dihydro-1H-benzo[d]imidazol-5-yl)oxy)acetohydrazide

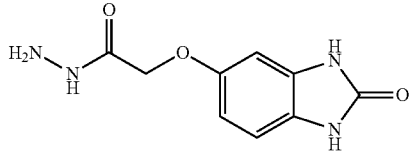 [SMILES: NNC(=O)COc1ccc2[nH]c(=O)[nH]c2c1]

By a procedure analogous to the preparation of 2-(2-oxo-1,2,3,4-tetrahydroquinolin-6-yloxy)acetohydrazide, 2-((2-oxo-2,3-dihydro-1H-benzo[d]imidazol-5-yl)oxy)acetohydrazide (0.5 g, 95%) was synthesized. 1H NMR: 400 MHz, DMSO-d6: δ 1.20-1.22 (m, 3H), 4.17 (q, J=7.20 Hz, 2H), 4.70 (s, 2H), 6.51-6.51 (m, 2H), 6.79-6.80 (m, 1H), 10.41 (s, 1H), 10.51 (s, 1H).

Ethyl 2-((2-oxo-1,2-dihydroquinoxalin-6-yl)oxy)acetate

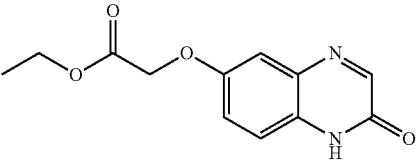 [SMILES: CCOC(=O)COc1ccc2[nH]c(=O)cnc2c1]

To a solution of ethyl 2-(3,4-diaminophenoxy)acetate (1.3 g, 6.18 mmol) in toluene (10 mL) was added ethyl glyoxalate solution (2.52 mL, 12.37 mmol) and the reaction mixture was heated at 90° C. for 4 h. The reaction was cooled to room temperature. The solid was filtered, washed with diethyl ether (10 mL) and dried to yield ethyl 2-((2-oxo-1,2-dihydroquinoxalin-6-yl)oxy)acetate (1.1 g, 68%). LCMS: RT 1.18 min. LCMS (ES-API), m/z 247(−ve mode).

2-((2-oxo-1,2-dihydroquinoxalin-6-yl)oxy)acetohydrazide

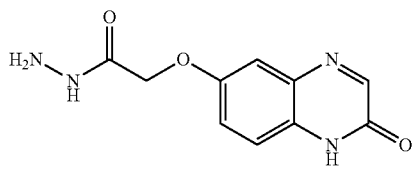 [SMILES: NNC(=O)COc1ccc2[nH]c(=O)cnc2c1]

By a procedure analogous to the preparation of 2-(2-oxo-1,2,3,4-tetrahydroquinolin-6-yloxy)acetohydrazide, 2-((2-oxo-1,2-dihydroquinoxalin-6-yl)oxy)acetohydrazide (0.8 g, 77%) was synthesized. LCMS: RT 1.14 min. LCMS (ES-API), m/z 233 (−ve mode).

Ethyl 2-((3-oxo-3,4-dihydro-2H-benzo[b][1,4]oxazin-7-yl)oxy)acetate

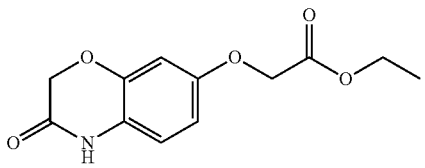 [SMILES: CCOC(=O)COc1ccc2c(c1)OCC(=O)N2]

By a procedure analogous to that used for the synthesis of Ethyl 2-((2-oxoindolin-5-yl)oxy)acetate, ethyl 2-((3-oxo-3,4-dihydro-2H-benzo[b][1,4]oxazin-7-yl)oxy)acetate (0.09 g, 30%) was synthesized. LCMS: RT 1.318 min. LCMS (ES-API), m/z 252.2 (M+H).

2-((3-oxo-3,4-dihydro-2H-benzo[b][1,4]oxazin-7-yl)oxy)acetohydrazide

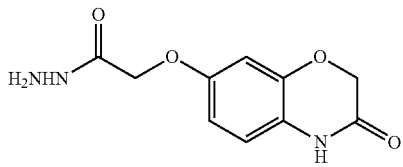

By a procedure analogous to the preparation of 2-(2-oxo-1,2,3,4-tetrahydroquinolin-6-yloxy)acetohydrazide, 2-((3-oxo-3,4-dihydro-2H-benzo[b][1,4]oxazin-7-yl)oxy)acetohydrazide (0.06 g, 60%) was synthesized. LCMS: RT 0.577 min. LCMS (ES-API), m/z 238.4 (M+H).

Ethyl 2-((1,2,3,4-tetrahydroquinolin-6-yl)oxy)acetate

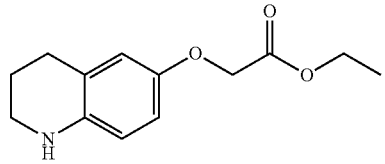 [SMILES: CCOC(=O)COc1ccc2c(c1)CCCN2]

To a solution of ethyl 2-(quinolin-6-yloxy)acetate (0.3 g, 1.297 mmol) in MeOH (70 mL) was added Platinum(IV) oxide (0.08 g, 0.352 mmol) under N2 atmosphere. The reaction was stirred under 3 kg H2 pressure at RT for 18 hrs. The reaction was filtered through Celite, washed with methanol, and the filtrate was concentrated to afford ethyl 2-((1,2,3,4-tetrahydroquinolin-6-yl)oxy)acetate as a yellow gum (0.25 g 85%). 1H NMR: 400 MHz, DMSO-d6: δ 1.20 (t, J=7.20 Hz, 3H), 1.76 (t, J=6.40 Hz, 2H), 2.62 (t, J=6.00 Hz, 2H), 3.11 (dd, J=2.00, 7.20 Hz, 2H), 4.13 (q, J=7.20 Hz, 2H), 4.56 (s, 2H), 5.26 (s, 1H), 6.35 (d, J=8.40 Hz, 1H), 6.47-6.51 (m, 2H), 6.58-6.61 (m, 1H).

2-((1,2,3,4-tetrahydroquinolin-6-yl)oxy)acetohydrazide

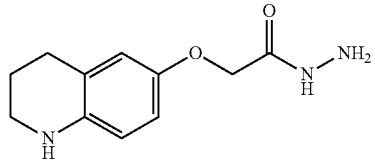 [SMILES: NNC(=O)COc1ccc2c(c1)CCCN2]

By a procedure analogous to the preparation of 2-(2-oxo-1,2,3,4-tetrahydroquinolin-6-yloxy)acetohydrazide, 2-((1,2,3,4-tetrahydroquinolin-6-yl)oxy)acetohydrazide (0.4 g, 69%) was synthesized. 1H NMR: 400 MHZ, DMSO-d6: δ 1.73-1.75 (m, 2H), 0.00 (t, J=6.40 Hz, 2H), 0.00 (t, J=4.40 Hz, 2H), 0.00 (s, 2H), 5.24 (s, 2H), 6.36 (d, J=8.40 Hz, 1H), 6.52-6.55 (m, 2H), 9.19 (s, 1H).

2-(4-chlorophenyl)-N'-hydroxyacetimidamide

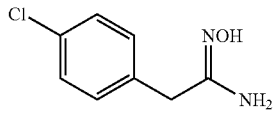

To a stirred solution of 2-(4-chlorophenyl)acetonitrile (1 g, 6.5 mmol) in ethanol (20 mL) at room temperature, hydroxylamine hydrochloride (4.5 g, 65.6 mmol) and potassium carbonate (12.5 g, 91 mmol) were added and heated at 80° C. overnight. Solvent was removed under vacuum. The residue was dissolved in ethyl acetate (50 mL) and the solution was washed with water and brine, and dried over sodium sulfate. Solvent was removed under vacuum to afford 2-(4-chlorophenyl)-N'-hydroxyacetimidamide (1 g, 83%) as an off-white solid. 1H NMR: 400 MHZ, DMSO-d6: δ 3.26 (s, 2H), 5.43 (s, 2H), 7.29-7.30 (m, 2H), 7.34-7.34 (m, 2H), 8.91 (s, 1H). LCMS: RT 0.89 min. LCMS (ES-API), m/z 186.0 (M+H).

Example 1

6-((5-(4-chlorophenylamino)-1,3,4-oxadiazol-2-yl) methoxy)-3,4-dihydroquinolin-2(1H)-one N-(4-chlorophenyl)-2-(2-(2-oxo-1,2,3,4-tetrahydro-quinolin-6-yloxy)acetyl)hydrazinecarbothioamide

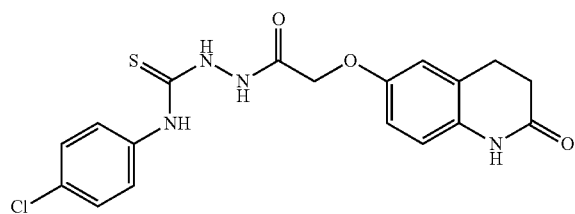 [SMILES: O=C(COc1ccc2c(c1)CCC(=O)N2)NNC(=S)Nc1ccc(Cl)cc1]

To a stirred solution of 2-(2-oxo-1,2,3,4-tetrahydroquinolin-6-yloxy)acetohydrazide (0.2 g, 0.85 mmol) in dry DMF (5 mL) at room temperature, 1-chloro-4-isothiocyanatobenzene (0.158 mg, 0.93 mmol) was added and the reaction was heated at 60° C. overnight. The reaction was monitored by LCMS. Solvent was removed under vacuum, then water (10 mL) was added to the residue. The solid was filtered and dried to yield crude N-(4-chlorophenyl)-2-(2-(2-oxo-1,2,3,4-tetrahydro-quinolin-6-yloxy)acetyl)hydrazinecarbothioamide (0.250 mg, 73%). LCMS: RT 1.39 min. LCMS (ES-API), m/z 405.0 (M+H).

6-((5-(4-chlorophenylamino)-1,3,4-oxadiazol-2-yl) methoxy)-3,4-dihydroquinolin-2(1H)-one

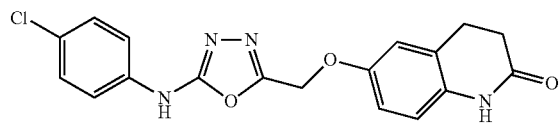 [SMILES: O=C1CCc2cc(OCc3nnc(Nc4ccc(Cl)cc4)o3)ccc2N1]

To a stirred solution of N-(4-chlorophenyl)-2-(2-(2-oxo-1,2,3,4-tetrahydroquinolin-6-yloxy)acetyl)hydrazinecarbothioamide (0.2 g, 0.49 mmol) in dry DMF (10 mL) at room temperature, EDC HCl (0.189 g, 0.98 mmol) and TEA (0.148 g 1.4 6 mmol) were added. The reaction was stirred at room temperature overnight and monitored by LCMS. The solvent was removed under vacuum and then water (20 mL) was added to the residue. The solid which formed was filtered, dried, and the crude product (0.15 g) was recrystallized in a mixture of ethanol/ACN to afford 6-((5-(4-chlorophenylamino)-1,3,4-oxadiazol-2-yl)methoxy)-3,4-dihydroquinolin-2(1H)-one (70 mg, 38%) as an off white solid. 1H NMR: 400 MHZ, DMSO-d6: δ 2.41 (t, J=7.20 Hz, 2H), 2.85 (t, J=8.00 Hz, 2H), 5.23 (s, 2H), 6.80 (d, J=8.40 Hz, 1H), 6.87 (dd, J=2.80, 8.40 Hz, 1H), 6.94 (d, J=2.40 Hz, 1H), 7.42 (dd, J=2.00, 6.80 Hz, 2H), 7.58 (dd, J=2.40, 6.80 Hz, 2H), 9.96 (s, 1H), 10.77 (s, 1H). LCMS: RT 1.50 min. LCMS (ES-API), m/z 371.0 (M+H).

Example 2

6-((5-(3,4-dichlorophenyl)-1,3,4-oxadiazol-2-yl) methoxy)quinolin-2(1H)-one

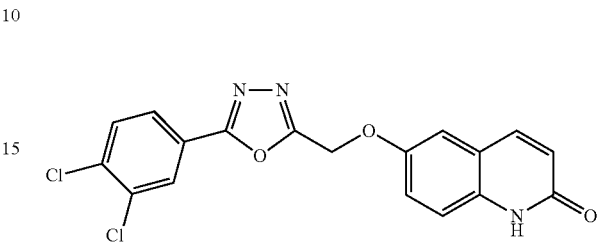

To a stirred solution of 2-((2-oxo-1,2-dihydroquinolin-6-yl)oxy)acetohydrazide (0.2 g, 0.858 mmol) and 3,4-dichlorobenzoic acid (0.163 g, 0.858 mmol)) in DMF (8 mL) was added triethylamine (0.598 mL, 4.29 mmol) and propylphosphonic anhydride (T3P) (0.819 g, 2.57 mmol). The reaction mixture was heated at 100° C. overnight under N2 atm. The reaction mixture was concentrated to remove solvent and ice-cold water was added. The precipitate was filtered and washed with water to afford a brown solid. The crude product was purified by preparative HPLC on a C18 reverse phase column (ACN-NH4OAc method) to give 6-((5-(3,4-dichlorophenyl)-1,3,4-oxadiazol-2-yl)methoxy)quinolin-2(1H)-one as a white solid (0.016 g, 4.81%). 1H NMR: 400 MHZ, DMSO-d6: δ 5.51 (s, 1H), 6.52 (d, J=9.60 Hz, 1H), 7.27-7.31 (m, 2H), 7.43 (d, J=2.40 Hz, 1H), 7.83-7.92 (m, 2H), 8.00 (dd, J=1.60, 8.40 Hz, 1H), 8.21 (d, J=1.60 Hz, 1H), 11.68 (s, 1H). LCMS: RT 1.92 min. LCMS (ES-API), m/z 390.0 (M+H).

Example 3

Isopropyl 4-((5-(3,4-dichlorophenylamino)-1,3,4-oxadiazol-2-yl)methoxy)phenyl carbamate 5-((4-aminophenoxy)methyl)-N-(3,4-dichlorophenyl)-1,3,4-oxadiazol-2-amine

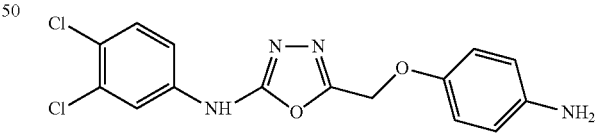

To a stirred solution of N-(3,4-dichlorophenyl)-5-((4-nitrophenoxy)methyl)-1,3,4-oxadiazol-2-amine (150 mg, 0.394 mmol) in water (20 mL)/methanol (20 mL), ammonium chloride (211 mg, 3.94 mmol) and iron powder (176 mg, 3.15 mmol) were added and heated to reflux for 4 hours. The reaction mixture was passed though Celite. Solvent was removed under vacuum to obtain 5-((4-aminophenoxy)methyl)-N-(3,4-dichlorophenyl)-1,3,4-oxadiazol-2-amine (0.12 g, 87%). 1H NMR: 400 MHZ, DMSO-d6: δ 5.16 (s, 2H), 5.60 (bs, 2H), 6.62 (d, J=8.40 Hz, 2H), 6.82 (dd, J=2.00, 6.80 Hz, 2H), 7.48 (dd, J=2.40, 8.80 Hz, 1H), 7.61 (d, J=8.80 Hz, 1H), 7.89 (d, J=2.80 Hz, 1H), 11.00 (s, 1H). LCMS: RT 1.66 min. LCMS (ES-API), m/z 351.0 (M+H).

Isopropyl(4-((5-((3,4-dichlorophenyl)amino)-1,3,4-oxadiazol-2-yl)methoxy)phenyl)carbamate

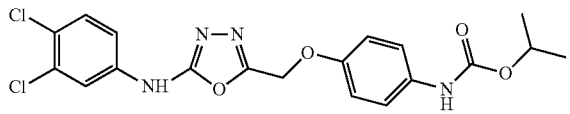 [SMILES: CC(C)OC(=O)Nc1ccc(OCc2nnc(Nc3ccc(Cl)c(Cl)c3)o2)cc1]

To a stirred solution of 5-((4-aminophenoxy)methyl)-N-(3,4-dichlorophenyl)-1,3,4-oxadiazol-2-amine (130 mg, 0.370 mmol) in pyridine (1 mL) at 0° C., isopropyl chloroformate (1 M solution in toluene, 0.370 mL, 0.370 mmol) was added and the reaction was stirred at room temperature overnight. Solvent was removed under vacuum. The residue was filtered and purified by preparative HPLC to obtain isopropyl (4-((5-((3,4-dichlorophenyl)amino)-1,3,4-oxadiazol-2-yl)methoxy)phenyl)carbamate (0.03 g, 14%). 1H NMR: 400 MHZ, DMSO-d6: δ 1.24 (d, J=6.00 Hz, 6H), 4.87 (t, J=6.40 Hz, 1H), 5.26 (s, 2H), 6.99 (dd, J=2.40, 6.80 Hz, 2H), 7.39 (d, J=8.80 Hz, 1H), 7.47 (dd, J=2.80, 9.00 Hz, 1H), 7.61 (d, J=8.80 Hz, 1H), 7.88 (d, J=2.80 Hz, 1H), 9.40 (s, 1H), 11.00 (s, 1H). LCMS: RT 2.11 min. LCMS (ES-API), m/z 439.0 (M+H).

The following compounds were synthesized by methods similar to that described for Examples 1-3.

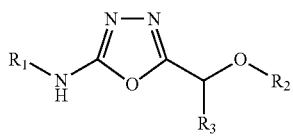

| Ex | R1 | R2 | R3 | LCMS RT (min) | LCMS Ion [M + H]+ | 1H NMR |
|---|---|---|---|---|---|---|
| 4 | 4-Br-phenyl | 3,4-dihydroquinolin-2(1H)-one-6-yl | H | 1.52 | 415.0 | 1H NMR: 400 MHZ, DMSO-d6: δ 2.42 (t, J = 7.20 Hz, 2H), 2.85 (t, J = 8.00 Hz, 2H), 5.23 (s, 2H), 6.80 (d, J = 8.40 Hz, 1H), 6.87 (dd, J = 2.80, 8.40 Hz, 1H), 6.94 (d, J = 2.40 Hz, 1H), 7.51-7.56 (m, 4H), 9.96 (s, 1H), 10.77 (s, 1H) |
| 5 | 3,4-diCl-phenyl | 3,4-dihydroquinolin-2(1H)-one-6-yl | H | 1.57 | 407.0 | 1H NMR: 400 MHZ, DMSO-d6: δ 2.42 (t, J = 7.20 Hz, 2H), 2.85 (t, J = 7.60 Hz, 2H), 5.25 (s, 2H), 6.80 (d, J = 8.40 Hz, 1H), 6.87 (dd, J = 2.80, 8.40 Hz, 1H), 6.94 (d, J = 2.40 Hz, 1H), 7.48 (dd, J = 2.40, 8.80 Hz, 1H), 7.62 (d, J = 8.80 Hz, 1H), 7.89 (d, J = 2.40 Hz, 1H), 9.96 (s, 1H), 11.06 (s, 1H). |
| 6 | 4-CF3-phenyl | 3,4-dihydroquinolin-2(1H)-one-6-yl | H | 1.57 | 407.0 | 1H NMR: 400 MHz, CDCl3: δ 2.41 (t, J = 7.20 Hz, 2H), 2.84 (t, J = 7.60 Hz, 2H), 5.25 (s, 1H), 6.79 (d, J = 8.80 Hz, 1H), 6.87 (dd, J = 2.80, 8.60 Hz, 1H), 6.94 (d, J = 2.40 Hz, 1H), 7.70-7.76 (m, 4H), 9.95 (s, 1H), 11.08 (s, 1H). |
| 7 | 4-CF3-phenyl | indolin-2-one-5-yl | H | 1.53 | [M − H]− 390.0 | 1H NMR: 400 MHZ, DMSO-d6: δ 3.32 (s, 2H), 5.25 (s, 2H), 6.75 (d, J = 8.40 Hz, 1H), 6.90 (q, J = 2.40 Hz, 1H), 7.01 (s, 1H), 7.72-7.77 (m, 4H), 10.24 (s, 1H), 11.08 (s, 1H). |

-continued

| Ex | R1 | R2 | R3 | LCMS RT (min) | LCMS Ion [M + H]+ | 1H NMR |
|---|---|---|---|---|---|---|
| 8 | 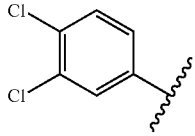 [SMILES: *c1ccc(Cl)c(Cl)c1] | 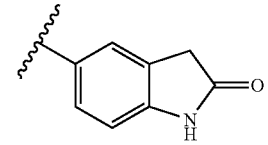 [SMILES: *c1ccc2c(c1)CC(=O)N2] | H | 1.65 | [M − H]− 391 | 1H NMR: 400 MHZ, DMSO-d6: δ 3.46 (s, 2H), 5.24 (s, 2H), 6.74 (d, J = 8.40 Hz, 1H), 6.87 (d, J = 2.40 Hz, 1H), 7.00 (s, 1H), 7.47 (dd, J = 2.80, 9.00 Hz, 1H), 7.61 (d, J = 8.80 Hz, 1H), 7.88 (d, J = 2.80 Hz, 1H), 10.23 (s, 1H), 11.00 (s, 1H). |
| 9 | 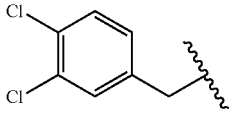 [SMILES: *Cc1ccc(Cl)c(Cl)c1] | 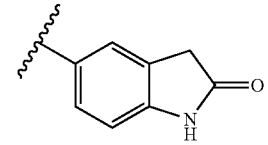 [SMILES: *c1ccc2c(c1)CC(=O)N2] | H | 1.38 | 407.0 | 1H NMR: 400 MHZ, DMSO-d6: δ 3.44 (s, 2H), 4.39 (d, J = 6.00 Hz, 2H), 5.08 (s, 2H), 6.72 (d, J = 8.40 Hz, 1H), 6.83 (dd, J = 2.40, 8.40 Hz, 1H), 6.96 (d, J = 2.40 Hz, 1H), 7.34 (dd, J = 2.00, 8.00 Hz, 1H), 7.60-7.62 (m, 2H), 8.31 (t, J = 6.00 Hz, 1H), 10.22 (s, 1H). |
| 10 | 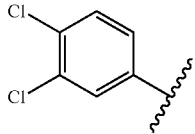 [SMILES: *c1ccc(Cl)c(Cl)c1] | 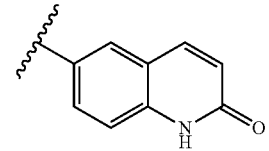 [SMILES: *c1ccc2[nH]c(=O)ccc2c1] | H | 1.54 | [M − H]− 402.0 | 1H NMR: 400 MHZ, DMSO-d6: δ 5.34 (s, 2H), 6.51 (dd, J = 2.00, 9.40 Hz, 1H), 7.27 (s, 2H), 7.39 (s, 1H), 7.47 (dd, J = 2.80, 8.60 Hz, 1H), 7.60 (d, J = 8.80 Hz, 1H), 7.83 (d, J = 9.60 Hz, 1H), 7.88 (d, J = 2.80 Hz, 1H), 8.31 (s, 1H), 10.99 (s, 1H), 11.67 (s, 1H). |
| 11 | 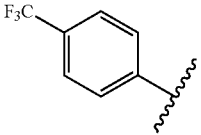 [SMILES: *c1ccc(C(F)(F)F)cc1] | 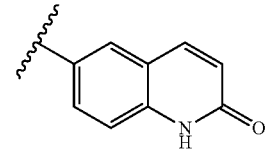 [SMILES: *c1ccc2[nH]c(=O)ccc2c1] | H | 1.50 | [M − H]− 401.0 | 1H NMR: 400 MHZ, DMSO-d6: δ 5.35 (s, 2H), 6.51 (dd, J = 1.60, 9.60 Hz, 1H), 7.27 (d, J = 1.20 Hz, 2H), 7.40 (s, 1H), 7.70-7.76 (m, 4H), 7.84 (d, J = 9.60 Hz, 1H), 11.08 (s, 1H), 11.67 (s, 1H) |
| 12 | 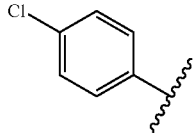 [SMILES: *c1ccc(Cl)cc1] | 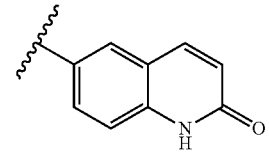 [SMILES: *c1ccc2[nH]c(=O)ccc2c1] | H | 1.46 | [M − H]− 367.0 | 1H NMR: 400 MHZ, DMSO-d6: δ 5.33 (s, 2H), 6.51 (dd, J = 1.60, 9.60 Hz, 1H), 7.27 (s, 2H), 7.40 (d, J = 8.80 Hz, 3H), 7.57 (d, J = 8.80 Hz, 2H), 7.83 (d, J = 9.60 Hz, 2H), 10.76 (s, 1H), 11.67 (s, 1H) |
| 13 | 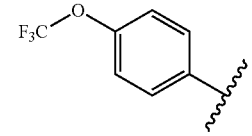 | 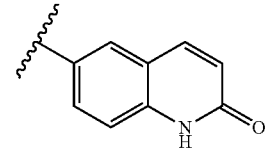 [SMILES: *c1ccc2[nH]c(=O)ccc2c1] | H | 1.84 | 419.0 | 1H NMR: 400 MHZ, DMSO-d6: δ 5.34 (s, 2H), 6.52 (dd, J = 1.60, 9.60 Hz, 1H), 7.28 (d, J = 1.60 Hz, 2H), 7.37-7.40 (m, 3H), 7.66 (dd, J = 2.00, 6.80 Hz, 2H), 7.85 (d, J = 9.60 Hz, 1H), 8.33 (s, 1H), 10.84 (s, 1H), 11.69 (s, 1H) |
| 14 | 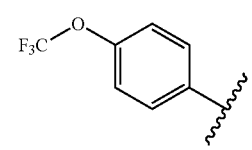 | 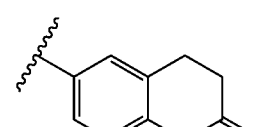 | H | 1.78 | 421.0 | 1H NMR: 400 MHZ, DMSO-d6: δ 2.41 (t, J = 7.20 Hz, 2H), 2.85 (t, J = 8.00 Hz, 2H), 5.23 (s, 2H), 6.80 (d, J = 8.80 Hz, 1H), 6.86 (d, J = 2.80 Hz, 1H), 6.94 (d, J = 2.80 Hz, 1H), 7.37 (d, J = 8.40 Hz, 2H), 7.65 (dd, J = 2.40, 7.00 Hz, 2H), 9.95 (s, 1H), 10.80 (s, 1H) |

-continued

| Ex | R1 | R2 | R3 | LCMS RT (min) | LCMS Ion [M + H]+ | 1H NMR |
|---|---|---|---|---|---|---|
| 15 | 5-chloropyridin-2-yl-methyl | 3,4-dihydroquinolin-2(1H)-one-6-yl | H | 1.64 | [M − H]− 370 | 1H NMR: 400 MHZ, DMSO-d6: δ 2.41 (t, J = 7.20 Hz, 2H), 2.85 (t, J = 7.60 Hz, 2H), 5.24 (s, 2H), 6.80 (d, J = 8.80 Hz, 1H), 6.87 (dd, J = 2.80, 8.40 Hz, 1H), 6.95 (d, J = 2.40 Hz, 1H), 7.92-7.97 (m, 2H), 8.37 (d, J = 1.60 Hz, 1H), 9.96 (s, 1H), 11.45 (s, 1H) |
| 16 | 4-(difluoromethoxy)benzyl | 3,4-dihydroquinolin-2(1H)-one-6-yl | H | 1.54 | [M − H]− 401 | 1H NMR: 400 MHZ, DMSO-d6: δ 109.81 (t, J = 7.20 Hz, 2H), 2.85 (t, J = 7.60 Hz, 2H) 5.22 (s, 2H), 6.80 (d, J = 8.00 Hz, 1H), 6.85-7.32 (m, 5H), 7.58 (dd, J = 2.40, 7.00 Hz, 2H), 9.95 (s, 1H), 10.66 (s, 1H) |
| 17 | 4-(difluoromethoxy)benzyl | quinolin-2(1H)-one-6-yl | H | 1.45 | [M − H]− 399 | 1H NMR: 400 MHZ, DMSO-d6: δ 5.32 (s, 2H), 6.52 (d, J = 9.60 Hz, 1H), 7.12-7.39 (m, 5H), 7.58 (dd, J = 2.40, 6.80 Hz, 2H), 7.84 (d, J = 9.60 Hz, 1H), 10.67 (s, 1H), 11.67 (s, 1H) |
| 18 | 4-(2-ethoxy-2-oxoethyl)benzyl | 3,4-dihydroquinolin-2(1H)-one-6-yl | H | 1.69 | 423 | 1H NMR: 400 MHZ, DMSO-d6: δ 1.18 (t, J = 7.20 Hz, 3H), 2.41 (t, J = 7.20 Hz, 2H), 2.85 (t, J = 8.00 Hz, 2H), 3.60 (s, 2H), 4.08 (q, J = 7.20 Hz, 2H), 5.22 (s, 2H), 6.80 (d, J = 8.80 Hz, 1H), 6.87 (dd, J = 2.80, 8.80 Hz, 1H), 6.94 (d, J = 2.40 Hz, 1H), 7.23 (dd, J = 8.40 Hz, 2H), 7.49 (dd, J = 2.00, 6.60 Hz, 2H), 9.95 (s, 1H) |
| 19 | 4-chlorobenzyl | quinolin-2(1H)-one-6-yl | H | 1.66 | 483 | 1H NMR: 400 MHZ, DMSO-d6: δ 4.37 (d, J = 6.40 Hz, 2H), 5.19 (s, 2H), 6.51 (d, J = 9.60 Hz, 1H), 7.21-7.27 (m, 2H), 7.34-7.41 (m, 5H), 7.82 (d, J = 9.60 Hz, 1H), 8.29 (t, J = 6.40 Hz, 1H), 11.66 (s, 1H) |
| 20 | 4-chlorobenzyl | 3,4-dihydroquinolin-2(1H)-one-6-yl | H | 1.96 | 385.0 | 1H NMR: 400 MHZ, DMSO-d6: δ 2.40 (t, J = 7.20 Hz, 2H), 2.83 (t, J = 8.00 Hz, 2H), 4.37 (d, J = 6.40 Hz, 2H), 5.09 (s, 2H), 6.76-6.84 (m, 2H), 6.89 (d, J = 2.80 Hz, 1H), 7.35-7.41 (m, 4H), 8.28 (t, J = 6.40 Hz, 1H), 9.94 (s, 1H) |

-continued

| Ex | R1 | R2 | R3 | LCMS RT (min) | LCMS Ion [M + H]+ | 1H NMR |
|---|---|---|---|---|---|---|
| 21 | 3,4-dichlorophenyl-CH2- | 3,4-dihydroquinolin-2(1H)-one-6-yl-CH2- | H | 2.06 | 421 | 1H NMR: 400 MHZ, DMSO-d6: δ 2.40 (t, J = 7.20 Hz, 2H), 2.83 (t, J = 8.00 Hz, 2H), 4.39 (d, J = 6.40 Hz, 2H), 5.09 (s, 2H), 6.76-6.84 (m, 2H), 6.89 (d, J = 2.40 Hz, 1H), 7.34 (dd, J = 1.60, 8.40 Hz, 1H), 7.60-7.62 (m, 2H), 8.31 (t, J = 6.40 Hz, 1H), 9.94 (s, 1H) |
| 22 | 3,4-dichlorophenyl-CH2- | quinolin-2(1H)-one-6-yl-CH2- | H | 1.73 | 417.0 | 1H NMR: 400 MHZ, DMSO-d6: δ 4.39 (d, J = 6.40 Hz, 2H), 5.20 (s, 2H), 6.51 (d, J = 9.60 Hz, 1H), 7.23-7.27 (m, 2H), 7.33-7.35 (m, 2H), 7.59-7.62 (m, 2H), 7.81 (d, J = 9.20 Hz, 1H), 8.33 (t, J = Hz, H), 11.66 (s, H) |
| 23 | 4-(trifluoromethoxy)phenyl-CH2- | 3,4-dihydroquinolin-2(1H)-one-6-yl-CH2- | H | 1.76 | 435.0 | 1H NMR: 400 MHZ, DMSO-d6: δ 2.41 (t, J = 7.60 Hz, 2H), 2.84 (t, J = 7.60 Hz, 2H), 4.42 (d, J = 6.40 Hz, 2H), 5.10 (s, 2H), 6.77-6.85 (m, 2H), 6.90 (d, J = 2.40 Hz, 1H), 7.35 (d, J = 8.00 Hz, 2H), 7.48 (d, J = 8.40 Hz, 2H), 8.31 (t, J = 6.00 Hz, 1H), 9.95 (s, 1H) |
| 24 | 6-chloropyridin-3-yl-CH2- | quinolin-2(1H)-one-6-yl-CH2- | H | 1.35 | 384 | 1H NMR: 400 MHZ, DMSO-d6: δ 4.42 (d, J = 6.00 Hz, 2H), 5.19 (s, 2H), 6.51 (d, J = 9.60 Hz, 2H), 7.22 (dd, J = 2.40, 8.80 Hz, 2H), 7.34 (d, J = 2.80 Hz, 1H), 7.50 (d, J = 8.40 Hz, 1H), 7.82 (dd, J = 5.60, 8.80 Hz, 2H), 8.32 (t, J = 6.00 Hz, 1H), 8.40 (d, J = 2.00 Hz, 1H), 11.69 (s, 1H) |
| 25 | 6-chloropyridin-3-yl-CH2- | 3,4-dihydroquinolin-2(1H)-one-6-yl-CH2- | H | 1.38 | 386 | 1H NMR: 400 MHZ, DMSO-d6: δ 2.40 (t, J = 7.20 Hz, 2H), 2.83 (t, J = 7.60 Hz, 2H), 4.41 (d, J = 6.00 Hz, 2H), 5.09 (s, 2H), 6.76-6.83 (m, 2H), 6.89 (d, J = 2.40 Hz, 1H), 7.50 (d, J = 8.40 Hz, 1H), 7.83 (dd, J = 2.80, 8.20 Hz, 1H) 8.32 (s, 1H), 8.40 (d, J = 2.40 Hz, 1H), 9.94 (s, 1H). LCMS: RT 1.38 min |
| 26 | 4-(trifluoromethoxy)phenyl-CH2- | quinolin-2(1H)-one-6-yl-CH2- | H | 1.64 | 433.0 | 1H NMR: 400 MHZ, DMSO-d6: δ 4.42 (d, J = 6.40 Hz, 2H), 5.19 (s, 2H), 6.51 (dd, J = 2.00, 9.40 Hz, 1H), 7.21-7.27 (m, 2H), 7.33 (d, J = 8.00, Hz, 3H), 7.47 (d, J = 8.80 Hz, 2H), 7.82 (d, J = 9.60 Hz, 1H), 8.31 (t, J = 6.00 Hz, 1H), 11.66 (s, 1H) |

| Ex | R1 | R2 | R3 | LCMS RT (min) | LCMS Ion [M + H]+ | 1H NMR |
|---|---|---|---|---|---|---|
| 27 | 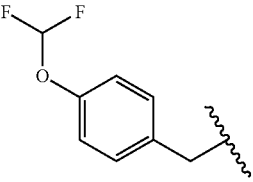 [SMILES: *Cc1ccc(OC(F)F)cc1] | 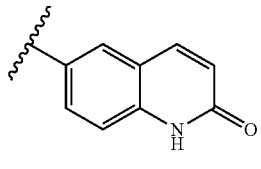 [SMILES: *c1ccc2[nH]c(=O)ccc2c1] | H | 1.57 | 415.0 | 1H NMR: 400 MHZ, DMSO-d6: δ 4.37 (d, J = 6.00 Hz, 2H), 5.19 (s, 2H), 6.51 (d, J = 9.60 Hz, 1H), 7.14 (d, J = 8.40 Hz, 2H), 7.20-7.28 (m, 3H), 7.34-7.40 (m, 3H), 7.82 (d, J = 9.60 Hz, 1H), 8.27 (t, J = 6.00 Hz, 1H), 11.958 (s, 1H) |
| 28 | 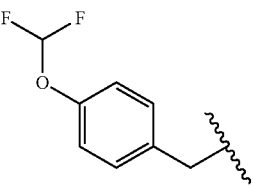 [SMILES: *Cc1ccc(OC(F)F)cc1] | 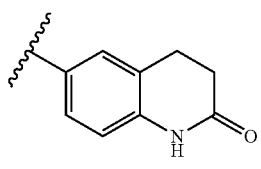 [SMILES: *c1ccc2c(c1)CCC(=O)N2] | H | 1.53 | 417.0 | 1H NMR: 400 MHZ, DMSO-d6: δ 2.40 (t, J = 7.60 Hz, 2H), 2.83 (t, J = 7.60 Hz, 2H), 4.37 (d, J = 6.00 Hz, 2H), 5.09 (s, 2H), 6.77-6.90 (m, 2H), 7.14-7.20 (m, 4H), 7.39 (t, J = 2.80 Hz, 2H), 8.26 (t, J = 6.00 Hz, 1H), 9.94 (s, 1H) |
| 29 | 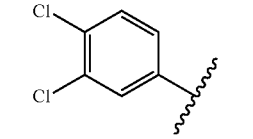 [SMILES: *c1ccc(Cl)c(Cl)c1] | 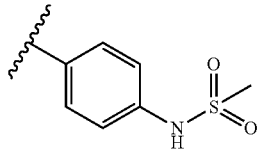 [SMILES: *c1ccc(NS(C)(=O)=O)cc1] | H | 1.84 | 429.0 | 1H NMR: 400 MHZ, DMSO-d6: δ 2.91 (s, 3H), 5.30 (s, 2H), 7.07 (d, J = 8.80 Hz, 2H), 7.19 (d, J = 8.80 Hz, 2H), 7.48 (dd, J = 2.80, 9.00 Hz, 1H), 7.62 (d, J = 8.80 Hz, 1H), 7.89 (d, J = 2.40 Hz, 1H), 9.46 (s, 1H) |
| 30 | 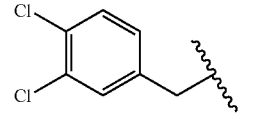 [SMILES: *Cc1ccc(Cl)c(Cl)c1] | 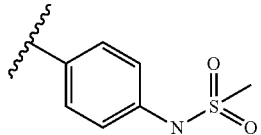 | H | 1.73 | 445.0 | 1H NMR: 400 MHZ, DMSO-d6: δ 2.91 (s, 3H), 4.40 (d, J = 6.00 Hz, 2H), 5.15 (s, 2H), 7.03 (dd, J = 2.00, 7.00 Hz, 2H), 7.17 (dd, J = 2.00, 6.60 Hz, 2H), 7.35 (dd, J = 2.00, 8.40 Hz, 1H), 7.62 (t, J = 3.20 Hz, 2H), 8.34 (t, J = 6.00 Hz, 1H), 9.44 (s, 1H) |
| 31 | 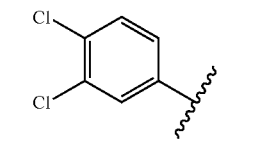 [SMILES: *c1ccc(Cl)c(Cl)c1] | 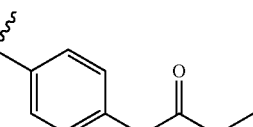 | H | 2.03 | 425.0 | 400 MHZ, DMSO-d6: δ 1.24 (t, J = 7.20 Hz, 3H), 4.11 (q, J = 6.80 Hz, 2H), 5.27 (s, 2H), 7.01 (dd, J = 2.00, 7.00 Hz, 2H), 7.39 (d, J = 8.80 Hz, 2H), 7.48 (dd, J = 2.80, 9.00 Hz, 1H), 7.62 (d, J = 8.80 Hz, 1H), 7.89 (d, J = 2.80 Hz, 1H), 9.47 (s, 1H), 11.00 (s, 1H). |
| 32 | 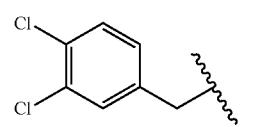 [SMILES: *Cc1ccc(Cl)c(Cl)c1] | 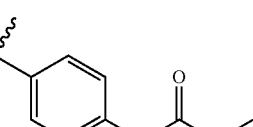 | H | 1.91 | 438.0 | 400 MHZ, DMSO-d6: δ 1.24 (t, J = 6.80 Hz, 3H), 4.11 (t, J = 7.20 Hz, 2H), 4.40 (d, J = 6.40 Hz, 2H), 5.11 (s, 2H), 6.96 (dd, J = 2.40, 6.80 Hz, 2H), 7.33-7.38 (m, 2H), 7.60-7.63 (m, 2H), 8.32 (t, J = 6.40 Hz, 1H), 9.45 (s, 1H). |
| 33 | 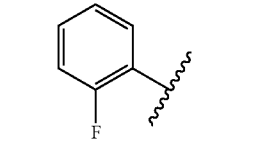 [SMILES: *c1ccccc1F] | 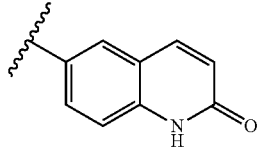 [SMILES: *c1ccc2[nH]c(=O)ccc2c1] | H | 1.502 | 353.0 | 400 MHz, DMSO-d6: δ 5.32 (s, 1H), 6.51-6.54 (m, 1H), 7.08-7.14 (m, 1H), 7.20- 7.31 (m, 4H), 7.40 (s, 1H), 7.84 (d, J = 9.60 Hz, 1H), 7.96-8.04 (m, 1H), 10.41 (s, 1H), 11.68 (s, 1H). |

-continued

| Ex | R1 | R2 | R3 | LCMS RT (min) | LCMS Ion [M + H]+ | 1H NMR |
|---|---|---|---|---|---|---|
| 34 | phenyl | 6-(2-oxo-1H-quinolin-6-yl) | H | 1.505 | 335.0 | 400 MHz, DMSO-d6: δ 5.33 (s, 2H), 6.52 (dd, J = 11.20, Hz, 1H), 7.02 (t, J = 14.80 Hz, 1H), 7.28 (d, J = 1.60 Hz, 2H), 7.33-7.40 (m, 3H), 7.54-7.56 (m, 2H), 7.85 (d, J = 9.60 Hz, 1H), 10.59 (s, 1H), 11.68 (s, 1H). |
| 35 | 4-chloro-2-fluorophenyl | 6-(2-oxo-1H-quinolin-6-yl) | H | 1.708 | 387.0 | 400 MHz, DMSO-d6: δ 5.33 (s, 2H), 6.52 (d, J = 9.20 Hz, 1H), 7.28-7.34 (m, 4H), 7.39 (s, 1H), 7.52 (dd, J = 13.60, Hz, 1H), 7.84 (d, J = 9.60 Hz, 1H), 8.09 (t, J = 18.00 Hz, 1H), 10.59 (s, 1H), 11.68 (s, 1H) |
| 36 | benzo[1,3]dioxol-5-yl | 6-(2-oxo-1H-quinolin-6-yl) | H | 1.480 | 378.3 | 400 MHz, DMSO-d6: δ 5.31 (s, 2H), 6.00 (s, 2H), 6.52 (d, J = 9.60 Hz, 1H), 6.89 (d, J = 8.40 Hz, 1H), 6.97 (dd, J = 2.40, 8.40 Hz, 1H), 7.20 (d, J = 2.00 Hz, 1H), 7.28 (s, 2H), 7.39 (s, 1H), 7.84 (d, J = 9.20 Hz, 1H), 10.44 (s, 1H), 11.68 (s, 1H), |
| 37 | 2,3-dihydrobenzo[1,4]dioxin-6-yl | 6-(2-oxo-1H-quinolin-6-yl) | H | 1.488 | 392.36 | 400 MHz, DMSO-d6: δ 4.22 (dd, J = 5.20, 13.20 Hz, 4H), 5.30 (s, 2H), 6.52 (d, J = 9.60 Hz, 1H), 6.82 (d, J = 8.40 Hz, 1H), 6.94 (dd, J = 2.40, 8.80 Hz, 1H), 7.15 (d, J = 2.40 Hz, 1H), 7.27 (d, J = 2.00 Hz, 2H), 7.39 (s, 1H), 7.84 (d, J = 9.60 Hz, 1H), 10.35 (s, 1H), 11.68 (s, 1H) |
| 38 | 3,4-dichlorophenyl | 6-(2-oxo-1H-quinolin-6-yl) | H | 1.951 | 441.0 | 400 MHz, DMSO-d6: δ 2.47 (q, J = 7.20 Hz, 2H), 2.90 (t, J = 7.60 Hz, 2H), 5.31 (s, 2H), 6.97 (d, J = 2.40 Hz, 1H), 7.10 (d, J = 2.80 Hz, 1H), 7.48 (dd, J = 2.80, 8.80 Hz, 1H), 7.61 (d, J = 8.80 Hz, 1H), 7.89 (d, J = 2.40 Hz, 1H), 9.42 (s, 1H), 11.02 (s, 1H) |
| 39 | 3-fluorophenyl | 6-(2-oxo-1H-quinolin-6-yl) | H | 1.568 | 353.0 | 400 MHz, DMSO-d6: δ 5.35 (s, 2H), 6.52 (d, J = 9.20 Hz, 1H), 6.84 (t, J = 8.40 Hz, 1H), 7.30 (d, J = 11.60 Hz, 3H), 7.38 (t, J = 8.00 Hz, 2H), 7.49 (d, J = 12.00 Hz, 1H), 7.84 (d, J = 9.20 Hz, 1H), 10.89 (s, 1H), 11.69 (s, 1H) |
| 40 | 4-fluorophenyl | 6-(2-oxo-1H-quinolin-6-yl) | H | 1.545 | 353.0 | 400 MHz, DMSO-d6: δ 5.33 (s, 2H), 6.52 (dd, J = 1.60, 9.60 Hz, 1H), 7.20 (t, J = 8.80 Hz, 2H), 7.28 (s, 2H), 7.40 (s, 1H), 7.55-7.58 (m, 2H), 7.84 (d, J = 9.60 Hz, 1H), 10.62 (s, 1H), 11.68 (s, 1H), . |

-continued

| Ex | R1 | R2 | R3 | LCMS RT (min) | LCMS Ion [M + H]+ | 1H NMR |
|---|---|---|---|---|---|---|
| 41 | 2-chlorophenyl-CH2- | quinolin-2(1H)-on-6-yl | H | 1.589 | 369.0 | 400 MHz, DMSO-d6: δ 5.31 (s, 2H), 6.52 (d, J = 9.60 Hz, 1H), 7.15 (t, J = 7.20 Hz, 1H), 7.27 (s, 2H), 7.36-7.39 (m, 2H), 7.51 (d, J = 8.00 Hz, 1H), 7.83 (d, J = 9.60 Hz, 1H), 7.95 (d, J = 8.00 Hz, 1H), 10.02 (s, 1H), 11.68 (s, 1H) |
| 42 | 3-(trifluoromethyl)phenyl-CH2- | quinolin-2(1H)-on-6-yl | H | 1.719 | 403.0 | 400 MHz, DMSO-d6: δ 5.36 (s, 2H), 6.52 (dd, J = 2.00, 9.40 Hz, 1H), 7.28 (d, J = 1.20 Hz, 2H), 7.38 (t, J = 7.60 Hz, 2H), 7.60 (t, J = 8.00 Hz, 1H), 7.78 (d, J = 9.60 Hz, 1H), 7.84 (d, J = 9.60 Hz, 1H), 8.01 (s, 1H), 11.03 (s, 1H), 11.68 (s, 1H) |
| 43 | phenyl-CH(CH3)- | quinolin-2(1H)-on-6-yl | H | 1.453 | 349.2 | 400 MHz, DMSO-d6: δ 4.38 (d, J = 6.00 Hz, 2H), 5.19 (s, 2H), 6.51 (d, J = 9.60 Hz, 1H), 7.21-7.34 (m, 8H), 7.82 (d, J = 9.60 Hz, 1H), 8.27 (t, J = 12.00 Hz, 1H), 11.67 (s, 1H) |
| 44 | 3-chloro-4-(trifluoromethyl)phenyl-CH2- | quinolin-2(1H)-on-6-yl | H | 1.718 | 451.0 | 400 MHz, DMSO-d6: δ 4.48 (d, J = 6.00 Hz, 2H), 5.20 (s, 2H), 6.51 (d, J = 9.20 Hz, 1H), 7.21-7.28 (m, 2H), 7.35 (d, J = 2.40 Hz, 1H), 7.66-7.72 (m, 2H), 7.83 (t, J = 15.20 Hz, 2H), 8.38 (t, J = 12.40 Hz, 1H), 11.67 (s, 1H) |
| 45 | 4-methylphenyl-CH2- | quinolin-2(1H)-on-6-yl | H | 1.609 | 349.0 | 400 MHz, DMSO-d6: δ 2.26 (s, 3H), 5.32 (s, 2H), 6.52 (d, J = 9.60 Hz, 1H), 7.15 (d, J = 8.40 Hz, 2H), 7.28 (s, 2H), 7.42 (t, J = 19.20 Hz, 3H), 7.84 (d, J = 9.20 Hz, 1H), 10.46 (s, 1H), 11.68 (s, 1H) |
| 46 | 3-methylphenyl-CH2- | quinolin-2(1H)-on-6-yl | H | 1.615 | 349.0 | 400 MHz, DMSO-d6: δ 2.30 (s, 3H), 5.33 (s, 2H), 6.52 (d, J = 9.60 Hz, 1H), 6.84 (d, J = 7.60 Hz, 1H), 7.22 (t, J = 15.60 Hz, 1H), 7.28 (s, 1H), 7.34-7.40 (m, 3H), 7.84 (d, J = 9.60 Hz, 1H), 10.51 (s, 1H), 11.68 (s, 1H) |
| 47 | 3,4-difluorophenyl-CH2- | quinolin-2(1H)-on-6-yl | H | 1.603 | 370.31 | 400 MHz, DMSO-d6: δ 5.34 (s, 1H), 6.52 (d, J = 11.20 Hz, 1H), 7.29 (d, J = 9.20 Hz, 3H), 7.40-7.43 (m, 2H), 7.64-7.64 (m, 1H), 7.84 (d, J = 9.60 Hz, 1H), 10.88 (s, 1H), 11.68 (s, 1H) |
| 48 | 3,4-dimethylphenyl-CH2- | quinolin-2(1H)-on-6-yl | H | 1.693 | 362.38 | 400 MHz, DMSO-d6: δ 2.19 (d, J = 14.00 Hz, 6H), 5.31 (s, 2H), 6.52 (d, J = 11.60 Hz, 1H), 7.09 (d, J = 8.00 Hz, 1H), 7.27 (s, 3H), 7.32 (s, 1H), 7.39 (s, 1H), 7.84 (d, J = 9.60 Hz, 1H) |

-continued

| Ex | R1 | R2 | R3 | LCMS RT (min) | LCMS Ion [M + H]+ | 1H NMR |
|---|---|---|---|---|---|---|
| 49 | 4-Cl, 3-F phenyl | quinolin-2(1H)-one-6-yl | H | 1.523 | 386.76 | 400 MHz, DMSO-d6: δ 5.35 (s, 2H), 6.52 (d, J = 11.20 Hz, 1H), 7.28 (s, 2H), 7.34 (d, J = 10.40 Hz, 1H), 7.40 (s, 1H), 7.56 (t, J = 17.60 Hz, 1H), 7.67 (dd, J = 2.40, 11.80 Hz, 1H), 7.84 (d, J = 9.60 Hz, 1H) |
| 50 | 3,4-diCl phenyl | 1H-indazol-5-yl | H | 1.701 | 374 [M − H]− | 400 MHz, DMSO-d6: δ 5.33 (s, 2H), 7.08-7.11 (m, 1H), 7.39 (d, J = 2.00 Hz, 1H), 7.46-7.50 (m, 2H), 7.60 (d, J = 8.80 Hz, 1H), 7.88 (d, J = 2.80 Hz, 1H), 0.99 (s, 1H), 11.00 (bs, 1H), 12.98 (s, 1H) |
| 51 | 4-Cl, 3-CF3 phenyl | quinolin-2(1H)-one-6-yl | H | 1.855 | 437.0 | 400 MHz, DMSO-d6: δ 5.41 (s, 2H), 6.52 (d, J = 9.60 Hz, 1H), 7.27 (s, 2H), 7.40 (s, 1H), 7.71 (d, J = 8.80 Hz, 1H), 7.79-7.85 (m, 3H), 8.11 (d, J = 2.40 Hz, 1H), 11.17 (s, 1H), 11.69 (s, 1H) |
| 52 | 4-isopropyl phenyl | quinolin-2(1H)-one-6-yl | H | 1.82 | 377.2 | 400 MHz, DMSO-d6: δ 1.18 (d, J = 6.80 Hz, 6H), 2.81-2.90 (m, 1H), 5.31 (s, 2H), 6.52 (d, J = 9.60 Hz, 1H), 7.21 (d, J = 8.80 Hz, 2H), 7.27 (s, 2H), 7.39 (s, 1H), 7.44 (d, J = 8.80 Hz, 2H), 7.84 (d, J = 9.60 Hz, 1H), 10.45 (s, 1H), 11.68 (s, 1H) |
| 53 | 3,5-diCl phenyl | quinolin-2(1H)-one-6-yl | H | 1.88 | 403.0 | 400 MHz, MeOD: δ 1.91-1.95 (m, 1H), 2.26-2.30 (m, 1H), 2.91-3.08 (m, 3H), 3.18 (t, J = 17.60 Hz, 1H), 3.32-3.62 (m, 3H), 3.82 (s, 3H), 4.10-4.15 (m, 2H), 6.78 (t, J = 14.40 Hz, 2H) |
| 54 | 2-CF3 phenyl | quinolin-2(1H)-one-6-yl | H | 1.829 | 403.0 | 400 MHz, DMSO-d6: δ 5.27 (s, 2H), 6.52 (d, J = 9.20 Hz, 1H), 7.26-7.29 (m, 2H), 7.37 (s, 1H), 7.45 (s, 1H), 7.71-7.84 (m, 4H), 9.90 (s, 1H), 11.67 (s, 1H) |
| 55 | 4-Cl, 3-OCF3 phenyl | quinolin-2(1H)-one-6-yl | H | 2.268 | 453.0 | 400 MHz, DMSO-d6: δ 5.36 (s, 2H), 6.52 (d, J = 9.60 Hz, 1H), 7.28 (s, 2H), 7.40 (s, 1H), 7.52 (dd, J = 2.40, 8.80 Hz, 1H), 7.67 (d, J = 8.80 Hz, 1H), 7.84 (d, J = 9.60 Hz, 1H), 7.89 (s, 1H), 11.13 (s, 1H), 11.69 (s, 1H) |
| 56 | 2,4-diCl phenyl | quinolin-2(1H)-one-6-yl | H | 1.782 | 403.0 | 400 MHz, DMSO-d6: δ 5.32 (s, 2H), 6.52 (dd, J = 1.60, 9.60 Hz, 1H), 7.27 (d, J = 1.60 Hz, 2H), 7.39 (s, 1H), 7.47 (dd, J = 2.40, 8.80 Hz, 1H), 7.67 (d, J = 2.40 Hz, 1H), 7.83 (d, J = 9.60 Hz, 1H), 8.03 (d, J = 8.80 Hz, 1H), 10.17 (s, 1H), 11.67 (s, 1H) |

-continued

| Ex | R1 | R2 | R3 | LCMS RT (min) | LCMS Ion [M + H]+ | 1H NMR |
|---|---|---|---|---|---|---|
| 57 | 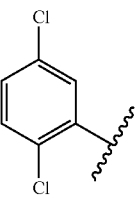 [SMILES: *c1cc(Cl)ccc1Cl] | 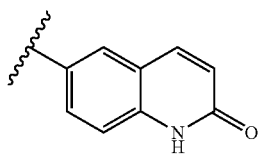 [SMILES: *c1ccc2[nH]c(=O)ccc2c1] | H | 1.755 | 403.0 | 400 MHz, DMSO-d6: δ 5.35 (s, 2H), 6.52 (dd, J = 1.60, 9.60 Hz, 1H), 7.21 (dd, J = 2.80, 8.60 Hz, 1H), 7.28 (s, 2H), 7.40 (s, 1H), 7.55 (d, J = 8.40 Hz, 1H), 7.84 (d, J = 9.60 Hz, 1H), 8.19 (d, J = 2.40 Hz, 1H), 10.29 (s, 1H), 11.69 (s, 1H) |
| 58 | 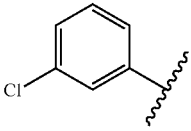 [SMILES: *c1cccc(Cl)c1] | 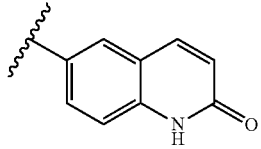 [SMILES: *c1ccc2[nH]c(=O)ccc2c1] | H | 1.677 | 368.77 | 400 MHz, DMSO-d6: δ 5.35 (s, 1H), 6.52 (d, J = 11.60 Hz, 1H), 7.08 (d, J = 10.80 Hz, 1H), 7.28 (s, 2H), 7.36-7.46 (m, 3H), 7.72 (s, 1H), 7.84 (d, J = 9.60 Hz, 1H) |
| 59 | 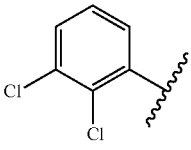 [SMILES: *c1cccc(Cl)c1Cl] | 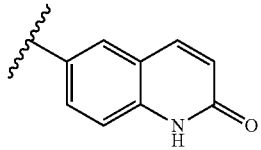 [SMILES: *c1ccc2[nH]c(=O)ccc2c1] | H | 1.739 | 403.22 | 400 MHz, DMSO-d6: δ 5.33 (s, 2H), 6.52 (d, J = 9.60 Hz, 1H), 7.29 (d, J = 8.00 Hz, 2H), 7.41 (d, J = 6.00 Hz, 3H), 7.84 (d, J = 9.60 Hz, 1H), 7.97-8.00 (m, 1H) |
| 60 | 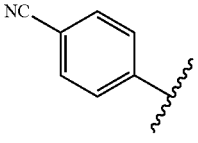 | 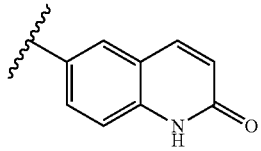 [SMILES: *c1ccc2[nH]c(=O)ccc2c1] | H | 1.324 | 359.34 | 400 MHz, DMSO-d6: δ 5.36 (s, 2H), 6.53 (d, J = 9.60 Hz, 1H), 7.28 (d, J = 1.20 Hz, 2H), 7.40 (s, 1H), 7.72 (t, J = 8.80 Hz, 2H), 7.82-7.86 (m, 3H) |
| 61 | 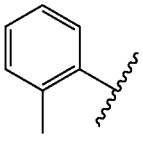 [SMILES: *c1ccccc1C] | 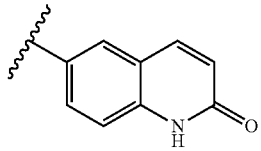 [SMILES: *c1ccc2[nH]c(=O)ccc2c1] | H | 1.526 | 348.36 | 400 MHz, DMSO-d6: δ 2.27 (s, 3H), 5.30 (s, 2H), 6.52 (d, J = 9.60 Hz, 1H), 7.05 (d, J = 7.20 Hz, 1H), 7.19-7.28 (m, 4H), 7.39 (s, 1H), 7.70 (d, J = 7.60 Hz, 1H), 7.84 (d, J = 9.60 Hz, 1H), 9.61 (s, 1H), 11.68 (s, 1H) |
| 62 | 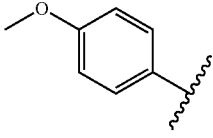 [SMILES: *c1ccc(OC)cc1] | 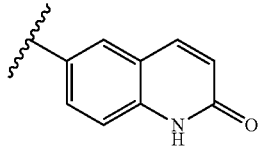 [SMILES: *c1ccc2[nH]c(=O)ccc2c1] | H | 1.475 | 364.35 | 400 MHz, DMSO-d6: δ 3.73 (s, 3H), 5.31 (s, 2H), 6.52 (d, J = 9.20 Hz, 1H), 6.93 (d, J = 9.20 Hz, 2H), 7.28 (s, 2H), 7.40 (s, 1H), 7.45 (d, J = 9.20 Hz, 2H), 7.84 (d, J = 9.60 Hz, 1H), 10.34 (s, 1H), 11.68 (s, 1H) |
| 63 | 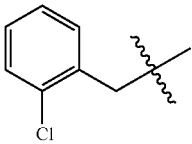 [SMILES: *Cc1ccccc1Cl] | 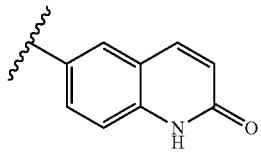 [SMILES: *c1ccc2[nH]c(=O)ccc2c1] | H | 1.640 | 383.0 | 400 MHz, DMSO-d6: δ 4.48 (d, J = 6.00 Hz, 2H), 5.21 (s, 2H), 6.52 (d, J = 9.60 Hz, 1H), 7.22-7.25 (m, 2H), 7.26-7.36 (m, 3H), 7.43-7.49 (m, 2H), 7.83 (d, J = 9.60 Hz, 1H), 8.36 (t, J = 12.00 Hz, 1H), 11.69 (s, 1H) |
| 64 | 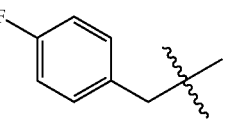 | 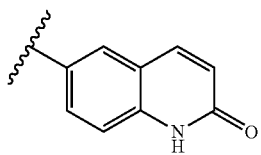 [SMILES: *c1ccc2[nH]c(=O)ccc2c1] | H | 1.480 | 366.35 | 400 MHz, MeOD: δ 4.46 (s, 2H), 5.22 (s, 2H), 6.66 (d, J = 9.60 Hz, 1H), 7.05-7.10 (m, 2H), 7.29-7.41 (m, 5H), 7.96 (d, J = 9.60 Hz, 1H) |

-continued

| Ex | R1 | R2 | R3 | LCMS RT (min) | LCMS Ion [M + H]+ | 1H NMR |
|---|---|---|---|---|---|---|
| 65 | 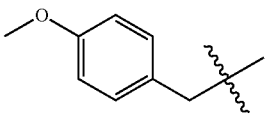 [SMILES: *Cc1ccc(OC)cc1] | 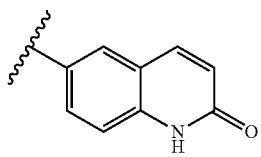 [SMILES: *c1ccc2[nH]c(=O)ccc2c1] | H | 1.505 | 378.38 | 400 MHz, DMSO-d6: δ 4.30 (d, J = 6.00 Hz, 2H), 5.19 (s, 2H), 6.52 (d, J = 9.60 Hz, 1H), 6.89 (d, J = 8.40 Hz, 2H), 7.26 (q, J = 12.80 Hz, 4H), 7.35 (d, J = 2.00 Hz, 1H), 7.82 (d, J = 9.60 Hz, 1H), 8.20 (d, J = 6.00 Hz, 1H), 11.69 (s, 1H) |
| 66 | 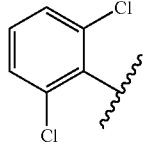 | 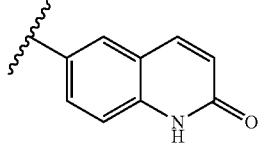 [SMILES: *c1ccc2[nH]c(=O)ccc2c1] | H | 1.539 | 403.22 | 400 MHz, MeOD: δ 5.28 (s, 2H), 6.67 (d, J = 9.60 Hz, 1H), 7.32-7.38 (m, 4H), 7.51 (d, J = 8.00 Hz, 2H), 7.96 (d, J = 9.60 Hz, 1H) |
| 67 | 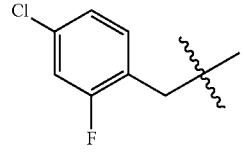 [SMILES: *Cc1ccc(Cl)cc1F] | 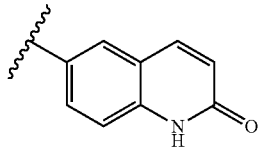 [SMILES: *c1ccc2[nH]c(=O)ccc2c1] | H | 1.663 | 401.0 | 400 MHz, MeOD: δ 4.51 (s, 2H), 5.22 (s, 2H), 6.65 (d, J = 9.60 Hz, 1H), 7.17-7.21 (m, 2H), 7.23-7.36 (m, 3H), 7.42 (t, J = 16.40 Hz, 1H), 7.94 (d, J = 9.60 Hz, 1H) |
| 68 | 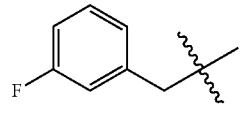 | 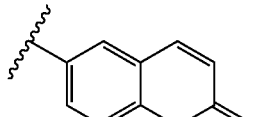 | H | 1.474 | 367.0 | 400 MHz, DMSO-d6: δ 4.41 (d, J = 6.00 Hz, 2H), 5.19 (s, 2H), 6.51 (d, J = 9.60 Hz, 1H), 7.07-7.27 (m, 5H), 7.34-7.41 (m, 2H), 7.82 (d, J = 9.60 Hz, 1H), 8.30 (t, J = 12.40 Hz, 1H), 11.66 (s, 1H) |
| 69 | 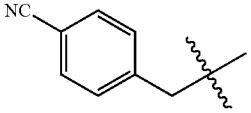 [SMILES: *Cc1ccc(C#N)cc1] | 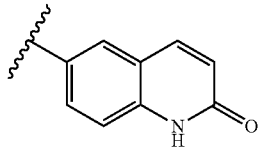 [SMILES: *c1ccc2[nH]c(=O)ccc2c1] | H | 1.342 | 373.36 | 400 MHz, MeOD: δ 4.57 (s, 2H), 5.22 (s, 2H), 6.65 (d, J = 9.60 Hz, 1H), 7.29 (dd, J = 2.80, 9.00 Hz, 1H), 7.34-7.36 (m, 2H), 7.55 (d, J = 8.80 Hz, 2H), 7.70-7.72 (m, 2H), 7.94 (d, J = 9.60 Hz, 1H) |
| 70 | 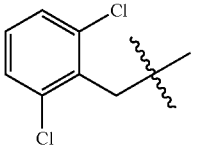 | 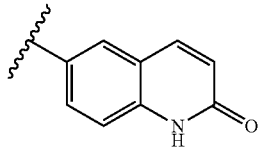 [SMILES: *c1ccc2[nH]c(=O)ccc2c1] | H | 1.651 | 417 | 400 MHz, MeOD: δ 4.78 (s, 2H), 5.22 (s, 2H), 6.65 (d, J = 9.60 Hz, 1H), 7.31-7.37 (m, 4H), 7.45 (d, J = 8.40 Hz, 2H), 7.95 (d, J = 9.60 Hz, 1H) |
| 71 | 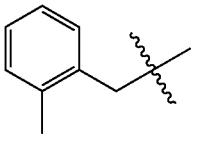 [SMILES: *Cc1ccccc1C] | 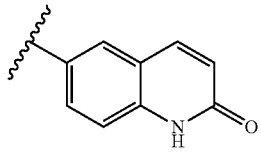 [SMILES: *c1ccc2[nH]c(=O)ccc2c1] | H | 1.568 | 362.38 | 400 MHz, MeOD: δ 2.36 (s, 3H), 4.48 (s, 2H), 5.22 (s, 2H), 6.65 (d, J = 9.60 Hz, 1H), 7.15-7.20 (m, 3H), 7.28-7.36 (m, 4H), 7.94 (d, J = 9.60 Hz, 1H) |
| 72 | 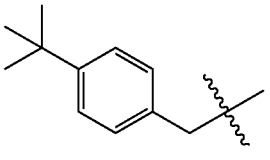 [SMILES: *Cc1ccc(C(C)(C)C)cc1] | 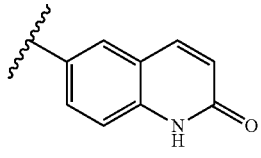 [SMILES: *c1ccc2[nH]c(=O)ccc2c1] | H | 1.861 | 404.46 | 400 MHz, MeOD: δ 4.43 (s, 2H), 5.21 (s, 2H), 6.65 (d, J = 9.60 Hz, 1H), 7.27-7.39 (m, 7H), 7.95 (d, J = 9.60 Hz, 1H) |

-continued

| Ex | R1 | R2 | R3 | LCMS RT (min) | LCMS Ion [M + H]+ | 1H NMR |
|---|---|---|---|---|---|---|
| 73 | 4-CF3, 3-Cl phenyl (CH2) | 6-quinolin-2(1H)-one | H | 1.892 | 437.0 | 400 MHz, DMSO-d6: δ 5.37 (s, 2H), 6.52 (dd, J = 2.00, 9.60 Hz, 1H), 7.28 (d, J = 1.60 Hz, 2H), 7.40 (s, 1H), 7.62 (d, J = 10.40 Hz, 1H), 7.84 (dd, J = 2.80, 9.20 Hz, 2H), 7.91 (d, J = 1.60 Hz, 1H), 11.33 (s, 1H), 11.68 (s, 1H) |
| 74 | 4-OCF3, 3-Cl phenyl (CH2) | 6-quinolin-2(1H)-one | H | 1.899 | 453.0 | 400 MHz, DMSO-d6: δ 5.35 (s, 2H), 6.52 (dd, J = 2.00, 9.20 Hz, 1H), 7.28 (d, J = 1.60 Hz, 2H), 7.39 (s, 1H), 7.55-7.57 (m, 2H), 7.84 (d, J = 9.60 Hz, 1H), 7.89 (d, J = 2.40 Hz, 1H), 11.07 (s, 1H), 11.67 (s, 1H) |
| 75 | 2-CF3 phenyl CH(CH3) | 6-quinolin-2(1H)-one | H | 1.613 | 417.0 | 400 MHz, DMSO-d6: δ 6.51 (d, J = 9.20 Hz, 1H), 7.24-7.27 (m, 2H), 7.35 (d, J = 2.40 Hz, 1H), 7.51 (t, J = 6.80 Hz, 1H), 7.62 (d, J = 7.60 Hz, 1H), 7.67 (t, J = 7.60 Hz, 1H), 7.74 (d, J = 7.60 Hz, 1H), 7.81 (d, J = 9.60 Hz, 1H), 8.39 (t, J = 6.40 Hz, 1H), 11.66 (s, 1H) |
| 76 | 4-CF3 phenyl CH(CH3) | 6-quinolin-2(1H)-one | H | 1.616 | 417.0 | 400 MHz, DMSO-d6: δ 4.49 (d, J = 6.00 Hz, 2H), 5.20 (s, 2H), 6.51 (dd, J = 1.60, 9.60 Hz, 1H), 7.22-7.28 (m, 2H), 7.35 (s, 1H), 7.56 (d, J = 8.40 Hz, 2H), 7.71 (d, J = 8.00 Hz, 2H), 7.82 (d, J = 9.60 Hz, 1H), 8.41 (t, J = 6.00 Hz, 1H), 11.69 (s, 1H) |
| 77 | 3-Cl phenyl CH(CH3) | 6-quinolin-2(1H)-one | H | 1.599 | 382.80 | 400 MHz, MeOD: δ 4.47 (s, 2H), 5.22 (s, 2H), 6.65 (d, J = 9.20 Hz, 1H), 7.28-7.39 (m, 7H), 7.94 (d, J = 9.60 Hz, 1H) |
| 78 | 4-tBu phenyl (CH2) | 6-quinolin-2(1H)-one | H | 1.893 | 390.44 | 400 MHz, DMSO-d6: δ 1.27 (s, 9H), 2.78 (d, J = 10.00 Hz, 1H), 3.09 (t, J = 7.20 Hz, 1H), 5.31 (s, 2H), 6.52 (d, J = 9.60 Hz, 1H), 7.28 (s, 2H), 7.34-7.46 (m, 5H), 7.84 (d, J = 9.60 Hz, 1H), 10.46 (s, 1H), 11.68 (s, 1H) |
| 79 | 2,3-dihydro-1,4-benzodioxin-6-yl CH(CH3) | 6-quinolin-2(1H)-one | H | 1.452 | 406.39 | 400 MHz, DMSO-d6: δ 4.23 (t, J = 17.60 Hz, 6H), 5.18 (s, 2H), 6.51 (d, J = 9.60 Hz, 1H), 6.78 (d, J = 2.00 Hz, 2H), 6.82 (d, J = 9.20 Hz, 1H), 7.21-7.27 (m, 2H), 7.34 (d, J = 2.40 Hz, 1H), 7.81 (d, J = 9.60 Hz, 1H), 8.16 (t, J = 12.40 Hz, 1H) |

| Ex | R1 | R2 | R3 | LCMS RT (min) | LCMS Ion [M + H]+ | 1H NMR |
|---|---|---|---|---|---|---|
| 80 | 3,4-dichlorophenyl-CH2- | 3,3-dimethyl-2-oxo-1,2,3,4-tetrahydroquinolin-6-yl | H | 1.969 | 433.29 | 400 MHz, DMSO-d6: δ 1.04 (s, 6H), 2.72 (s, 2H), 5.24 (s, 2H), 6.80 (d, J = 8.40 Hz, 1H), 6.86-6.91 (m, 2H), 7.48 (dd, J = 2.40, 9.00 Hz, 1H), 7.61 (d, J = 8.80 Hz, 1H), 7.89 (d, J = 2.40 Hz, 1H), 9.90 (s, 1H), 11.00 (s, 1H) |
| 81 | 4-(trifluoromethyl)phenyl-CH2- | 3,3-dimethyl-2-oxo-1,2,3,4-tetrahydroquinolin-6-yl | H | 1.88 | 432.40 | 400 MHz, DMSO-d6: δ 1.04 (s, 6H), 2.73 (s, 2H), 5.25 (s, 2H), 6.80 (d, J = 8.80 Hz, 1H), 6.87-6.92 (m, 2H), 7.71-7.77 (m, 4H), 9.90 (s, 1H), 11.08 (s, 1H) |
| 82 | 4-chlorophenyl-CH2- | 1H-indazol-5-yl | H | 1.576 | 341 | 400 MHz, DMSO-d6: δ 5.32 (s, 2H), 7.09-7.11 (m, 1H), 7.41 (t, J = 9.20 Hz, 3H), 7.49 (s, 1H), 7.57-7.59 (m, 2H), 8.00 (s, 1H), 10.74 (bs, 1H), 12.99 (s, 1H) |
| 83 | 4-chloro-3-fluorophenyl-CH2- | 3,3-dimethyl-2-oxo-1,2,3,4-tetrahydroquinolin-6-yl | H | 1.827 | 416.83 | 400 MHz, DMSO-d6: δ 1.04 (s, 6H), 2.72 (s, 2H), 5.24 (s, 2H), 6.80 (d, J = 8.80 Hz, 1H), 6.86-6.91 (m, 2H), 7.32-7.35 (m, 1H), 7.56 (t, J = 17.20 Hz, 1H), 7.66 (dd, J = 2.40, 11.60 Hz, 1H), 9.90 (s, 1H), 11.03 (s, 1H) |
| 84 | 3,4-dichlorophenyl-CH(CH3)- | 3,3-dimethyl-2-oxo-1,2,3,4-tetrahydroquinolin-6-yl | H | 1.797 | 447.31 | 400 MHz, DMSO-d6: δ 1.04 (s, 6H), 2.70 (s, 2H), 4.39 (d, J = 6.00 Hz, 2H), 5.09 (s, 2H), 6.77-6.86 (m, 3H), 7.34 (dd, J = 2.00, 8.20 Hz, 1H), 7.60-7.62 (m, 2H), 8.33 (t, J = Hz, 1H), 9.89 (s, 1H) |
| 85 | benzo[d][1,3]dioxol-5-yl-CH(CH3)- | 2-oxo-1,2-dihydroquinolin-6-yl | H | 1.518 | 392.7 | 400 MHz, MeOD: δ 4.37 (s, 2H), 5.21 (s, 2H), 5.93 (s, 2H), 6.65 (d, J = 9.20 Hz, 1H), 6.77 (d, J = 7.60 Hz, 1H), 6.82 (d, J = 1.60 Hz, 1H), 6.85 (s, 1H), 7.29-7.36 (m, 3H), 7.94 (d, J = 9.60 Hz, 1H). |
| 86 | 4-fluoro-3-methylphenyl-CH(CH3)- | 2-oxo-1,2-dihydroquinolin-6-yl | H | 1.634 | 381.0 | 400 MHz, MeOD: δ 2.26 (d, J = 2.00 Hz, 3H), 4.41 (s, 2H), 5.22 (s, 2H), 6.66 (d, J = 9.60 Hz, 1H), 6.99 (t, J = 18.00 Hz, 1H), 7.17-7.21 (m, 1H), 7.24 (d, J = 7.20 Hz, 1H), 7.29-7.37 (m, 3H), 7.95 (d, J = 9.20 Hz, 1H) |
| 87 | 4-(difluoromethoxy)-3-chlorophenyl-CH2- | 2-oxo-1,2-dihydroquinolin-6-yl | H | 1.825 | 435.0 | 400 MHz, DMSO-d6: δ 5.35 (s, 2H), 6.52 (dd, J = 2.00, 9.40 Hz, 1H), 6.95-7.40 (m, 5H), 7.49 (dd, J = 2.80, 8.80 Hz, 1H), 7.84 (t, J = 9.20 Hz, 2H), 10.92 (s, 1H), 11.68 (s, 1H) |

-continued

| Ex | R1 | R2 | R3 | LCMS RT (min) | LCMS Ion [M + H]⁺ | 1H NMR |
|---|---|---|---|---|---|---|
| 88 | (4-Cl, 3-OCHF₂-phenyl) | 6-quinolin-2(1H)-one | H | 1.852 | 435.0 | 400 MHz, DMSO-d6: δ 5.35 (s, 2H), 6.52 (d, J = 9.20 Hz, 1H), 7.06-7.44 (m, 5H), 7.57 (d, J = 8.80 Hz, 1H), 7.68 (d, J = 2.40 Hz, 1H), 7.84 (d, J = 9.60 Hz, 1H), 10.99 (s, 1H) |
| 89 | (3-phenoxyphenyl) | 6-quinolin-2(1H)-one | H | 1.919 | 427.0 | 400 MHz, DMSO-d6: δ 5311.00 (s, 2H), 6.51 (dd, J = 1.60, 9.60 Hz, 1H), 6.62-6.65 (m, 1H), 7.03-7.05 (m, 2H), 7.14 (t, J = 2.00 Hz, 1H), 7.16-7.43 (m, 8H), 7.83 (d, J = 9.60 Hz, 1H), 10.73 (s, 1H), 11.78 (s, 1H) |
| 90 | (4-F, 3-Me-phenyl) | 6-quinolin-2(1H)-one | H | 1.715 | 367.0 | 400 MHz, DMSO-d6: δ 2.23 (d, J = 1.60 Hz, 3H), 4.10 (s, 2H), 5.32 (s, 2H), 6.52 (dd, J = 2.00, 9.60 Hz, 1H), 7.13 (t, J = 9.20 Hz, 1H), 7.28 (s, 2H), 7.35-7.39 (m, 2H), 7.44 (dd, J = 2.40, 6.60 Hz, 1H), 7.84 (d, J = 9.60 Hz, 1H), 10.53 (s, 1H), 11.68 (s, 1H) |
| 91 | (4-phenoxyphenyl) | 6-quinolin-2(1H)-one | H | 1.965 | 427.0 | 400 MHz, DMSO-d6: δ 5.31 (s, 2H), 6.51 (d, J = 9.60 Hz, 1H), 6.62-6.65 (m, 1H), 7.03-7.05 (m, 1H), 7.14-7.18 (m, 1H), 7.26-7.36 (m, 5H), 7.38-7.42 (m, 3H), 7.83 (d, J = 9.60 Hz, 1H), 10.70 (s, 1H), 11.67 (s, 1H) |
| 92 | (4-Me, 3-Cl-phenyl) | 6-quinolin-2(1H)-one | H | 1.929 | 383.0 | 400 MHz, DMSO-d6: δ 2.28 (s, 3H), 5.34 (s, 2H), 6.52 (dd, J = 1.60, 9.60 Hz, 1H), 7.28-7.40 (m, 5H), 7.70 (d, J = 2.00 Hz, 1H), 7.84 (d, J = 9.60 Hz, 1H), 10.73 (s, 1H), 11.68 (s, 1H) |
| 93 | (4-OCHF₂-phenyl with iPr) | 6-quinolin-2(1H)-one | H | 1.80 | 393.0 | 400 MHz, DMSO-d6: δ 1.25 (d, J = 6.00 Hz, 6H), 4.50-4.56 (m, 1H), 5.32 (s, 2H), 6.52 (dd, J = 1.20, 9.60 Hz, 1H), 6.91 (d, J = 9.20 Hz, 2H), 7.28 (s, 2H), 7.40-7.45 (m, 3H), 7.84 (d, J = 9.60 Hz, 1H), 10.33 (s, 1H), 11.68 (s, 1H) |
| 94 | (3-methylbenzyl) | 6-quinolin-2(1H)-one | H | 1.712 | 363.0 | 400 MHz, DMSO-d6: δ 2.29 (s, 3H), 4.35 (d, J = 6.40 Hz, 2H), 5.20 (s, 1H), 6.51 (d, J = 9.60 Hz, 1H), 7.07-7.35 (m, 7H), 7.82 (d, J = 9.60 Hz, 1H), 8.23 (t, J = 12.40 Hz, 1H), 11.67 (s, 1H) |

-continued

| Ex | R1 | R2 | R3 | LCMS RT (min) | LCMS Ion [M + H]+ | 1H NMR |
|---|---|---|---|---|---|---|
| 95 | 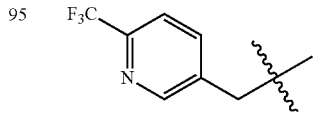 | 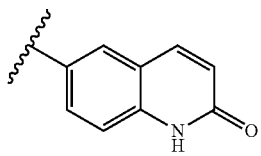 [SMILES: *c1ccc2[nH]c(=O)ccc2c1] | H | 1.430 | 436.0 | 400 MHz, DMSO-d6: δ 4.55 (d, J = 6.00 Hz, 2H), 5.20 (s, 2H), 6.51 (d, J = 9.60 Hz, 1H), 7.22-7.28 (m, 2H), 7.35 (d, J = 2.40 Hz, 1H), 7.82 (d, J = 9.60 Hz, 1H), 7.90 (d, J = 8.00 Hz, 1H), 8.05 (d, J = 8.40 Hz, 1H), 8.43 (t, J = 12.00 Hz, 1H), 8.76 (s, 1H), 11.67 (s, 1H) |
| 96 | 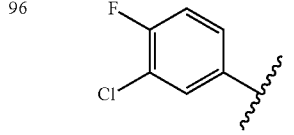 | 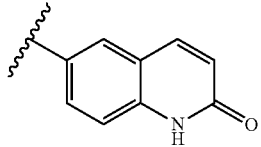 [SMILES: *c1ccc2[nH]c(=O)ccc2c1] | H | 1.866 | 387.0 | 400 MHz, DMSO-d6: δ 5.34 (s, 2H), 6.52 (d, J = 9.60 Hz, 1H), 7.28 (s, 2H), 7.40-7.46 (m, 3H), 7.81-7.85 (m, 2H), 10.87 (s, 1H), 11.68 (s, 1H) |
| 97 | 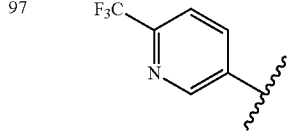 | 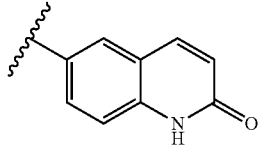 [SMILES: *c1ccc2[nH]c(=O)ccc2c1] | H | 1.643 | 402.0 | 400 MHz, DMSO-d6: δ 5.38 (s, 2H), 6.52 (d, J = 9.20 Hz, 1H), 7.29 (d, J = 1.60 Hz, 2H), 7.41 (s, 1H), 7.85 (d, J = 9.60 Hz, 1H), 7.93 (d, J = 8.80 Hz, 1H), 8.30 (dd, J = 2.80, 8.60 Hz, 1H), 8.82 (d, J = 2.40 Hz, 1H), 11.42 (s, 1H), 11.69 (s, 1H) |
| 98 | 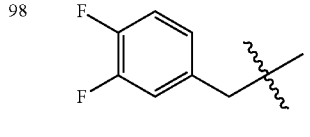 | 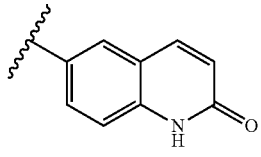 [SMILES: *c1ccc2[nH]c(=O)ccc2c1] | H | 1.551 | 384.33 | 400 MHz, MeOD: δ 4.45 (s, 2H), 5.22 (s, 2H), 6.65 (d, J = 9.60 Hz, 1H), 7.18-7.36 (m, 6H), 7.94 (d, J = 9.60 Hz, 1H) |
| 99 | 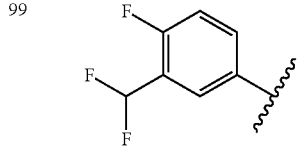 | 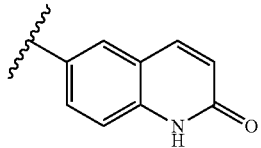 [SMILES: *c1ccc2[nH]c(=O)ccc2c1] | H | 1.660 | 403.0 | 400 MHz, DMSO-d6: δ 5.34 (s, 2H), 6.52 (d, J = 9.60 Hz, 1H), 7.24-7.42 (m, 5H), 7.68-7.72 (m, 1H), 7.83-7.89 (m, 2H), 10.87 (s, 1H), 11.68 (s, 1H) |
| 100 | 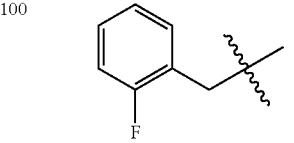 | 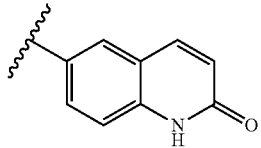 [SMILES: *c1ccc2[nH]c(=O)ccc2c1] | H | 1.505 | 367.0 | 400 MHz, DMSO-d6: δ 4.44 (d, J = 6.00 Hz, 2H), 5.20 (s, 2H), 6.51 (d, J = 9.60 Hz, 1H), 7.16-7.28 (m, 4H), 7.32-7.35 (m, 2H), 7.40-7.45 (m, 1H), 7.82 (d, J = 9.60 Hz, 1H), 8.30 (t, J = 12.00 Hz, 1H), 11.67 (s, 1H) |
| 101 | 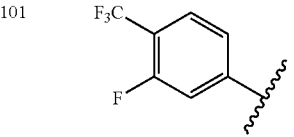 | 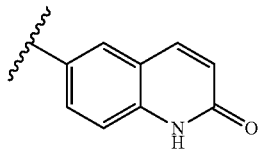 [SMILES: *c1ccc2[nH]c(=O)ccc2c1] | H | 1.606 | 420.08 | 400 MHz, MeOD: δ 5.35 (s, 2H), 6.66 (d, J = 9.60 Hz, 1H), 7.35-7.42 (m, 4H), 7.65 (dd, J = 8.80, 18.20 Hz, 2H), 7.97 (d, J = 9.60 Hz, 1H) |
| 102 | 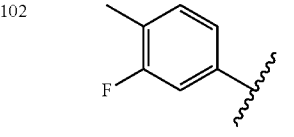 | 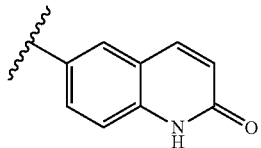 [SMILES: *c1ccc2[nH]c(=O)ccc2c1] | H | 1.653 | 366.9 | 400 MHz, DMSO-d6: δ 2.18 (s, 3H), 5.33 (s, 2H), 6.52 (d, J = 9.20 Hz, 1H), 7.18-7.27 (m, 4H), 7.42 (dd, J = 7.60, 16.80 Hz, 2H), 7.84 (d, J = 10.00 Hz, 1H), 10.75 (s, 1H), 11.69 (s, 1H) |

| Ex | R1 | R2 | R3 | LCMS RT (min) | LCMS Ion [M + H]+ | 1H NMR |
|---|---|---|---|---|---|---|
| 103 | 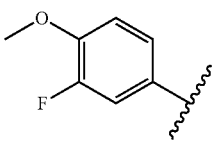 [SMILES: *c1ccc(OC)c(F)c1] | 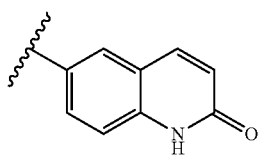 [SMILES: *c1ccc2[nH]c(=O)ccc2c1] | H | 1.564 | 383.4 | 400 MHz, DMSO-d6: δ 3.81 (s, 3H), 5.32 (s, 2H), 6.52 (d, J = 9.60 Hz, 1H), 7.17 (t, J = 18.40 Hz, 1H), 7.23-7.27 (m, 3H), 7.39 (s, 1H), 7.47 (dd, J = 2.40, 13.60 Hz, 1H), 7.84 (d, J = 9.60 Hz, 1H), 10.60 (s, 1H), 11.69 (s, 1H) |
| 104 | 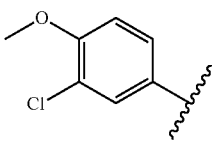 | 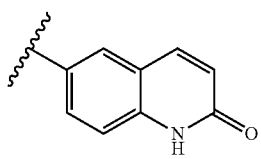 [SMILES: *c1ccc2[nH]c(=O)ccc2c1] | H | 1.78 | 400.2 | 400 MHz, DMSO-d6: δ 3.82 (s, 3H), 5.32 (s, 2H), 6.52 (dd, J = 1.60, 9.60 Hz, 1H), 7.16 (d, J = 9.20 Hz, 1H), 7.27 (s, 2H), 7.39-7.44 (m, 2H), 7.68 (d, J = 2.80 Hz, 1H), 7.84 (d, J = 9.60 Hz, 1H), 10.58 (s, 1H), 11.69 (s, 1H) |
| 105 | 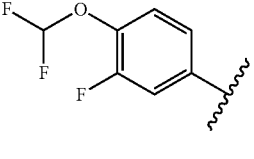 | 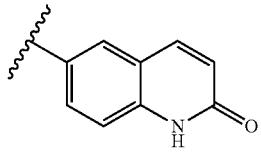 [SMILES: *c1ccc2[nH]c(=O)ccc2c1] | H | 1.494 | 418.08 | 400 MHz, DMSO-d6: δ 5.34 (s, 2H), 6.52 (d, J = 9.60 Hz, 1H), 6.97-7.40 (m, 6H), 7.63 (dd, J = 2.40, 12.80 Hz, 1H), 7.84 (d, J = 9.60 Hz, 1H), 10.95 (s, 1H), 11.68 (s, 1H) |
| 106 | 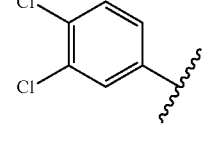 | 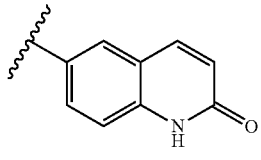 [SMILES: *c1ccc2[nH]c(=O)ccc2c1] | CH3 | 1.903 | 417.25 | 400 MHz, DMSO-d6: δ 1.72 (d, J = 6.40 Hz, 3H), 5.76 (q, J = 19.60 Hz, 1H), 6.51 (dd, J = 1.20, 9.60 Hz, 1H), 7.26 (d, J = 1.20 Hz, 2H), 7.38 (s, 1H), 7.45 (dd, J = 2.40, 8.80 Hz, 1H), 7.60 (d, J = 8.80 Hz, 1H), 7.81-7.86 (m, 2H), 11.01 (s, 1H), 11.69 (s, 1H) |
| 107 | 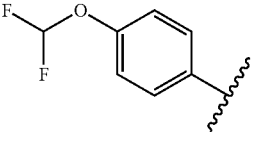 [SMILES: *c1ccc(OC(F)F)cc1] | 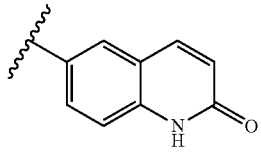 [SMILES: *c1ccc2[nH]c(=O)ccc2c1] | CH3 | 1.736 | 414.11 | 400 MHz, DMSO-d6: δ 1.72 (d, J = 6.40 Hz, 3H), 5.75 (q, J = 19.60 Hz, 1H), 6.50 (dd, J = 2.00, 9.60 Hz, 1H), 6.94-7.38 (m, 6H), 7.53-7.57 (m, 2H), 7.82 (d, J = 9.60 Hz, 1H), 1.67 (s, 1H), 11.69 (s, 1H) |
| 108 | 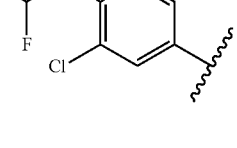 | 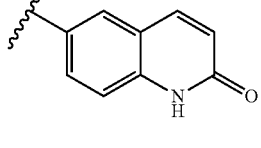 | CH3 | 1.839 | 448.81 | 400 MHz, DMSO-d6: δ 1.72 (d, J = 6.80 Hz, 3H), 5.76 (t, J = 19.60 Hz, 1H), 6.51 (dd, J = 2.00, 9.60 Hz, 1H), 6.99-7.48 (m, 6H), 7.80-7.83 (m, 2H), 10.92 (s, 1H), 11.69 (s, 1H) |
| 109 | 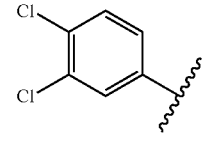 [SMILES: *c1ccc(Cl)c(Cl)c1] | 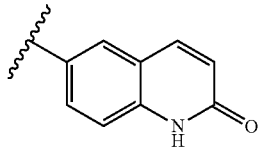 [SMILES: *c1ccc2[nH]c(=O)ccc2c1] | CH3 (enantiomer 1) | 1.908 | 417.25 | 400 MHz, MeOD: δ 1.83 (d, J = 6.80 Hz, 3H), 5.72 (q, J = 19.60 Hz, 1H), 6.65 (d, J = 9.60 Hz, 1H), 7.30-7.48 (m, 5H), 7.81 (d, J = 2.80 Hz, 1H), 7.95 (d, J = 9.60 Hz, 1H) |
| 110 | 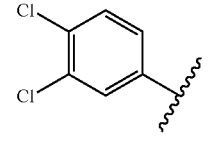 [SMILES: *c1ccc(Cl)c(Cl)c1] | 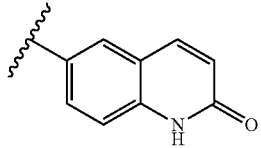 | CH3 (enantiomer 2) | 1.907 | 417.25 | 400 MHz, MeOD: δ 1.83 (d, J = 6.80 Hz, 3H), 5.72 (q, J = 19.60 Hz, 1H), 6.65 (d, J = 9.60 Hz, 1H), 7.30-7.48 (m, 5H), 7.81 (d, J = 2.80 Hz, 1H), 7.95 (d, J = 9.60 Hz, 1H) |

-continued

| Ex | R1 | R2 | R3 | LCMS RT (min) | LCMS Ion [M + H]+ | 1H NMR |
|---|---|---|---|---|---|---|
| 111 | 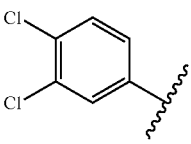 [SMILES: *c1ccc(Cl)c(Cl)c1] | 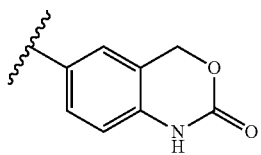 [SMILES: *c1ccc2c(c1)COC(=O)N2] | H | 1.81 | [M − H] 407.0 | 1H NMR: 400 MHZ, DMSO-d6: δ 5.25 (d, J = 10.00 Hz, 4H), 6.83 (t, J = 1.20 Hz, 1H), 6.97-7.00 (m, 2H), 7.47 (dd, J = 2.80, 8.80 Hz, 1H), 7.61 (d, J = 8.80 Hz, 1H), 7.88 (d, J = 2.80 Hz, 1H), 10.04 (s, 1H), 10.99 (s, 1H) |
| 112 | 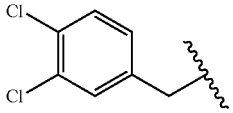 [SMILES: *Cc1ccc(Cl)c(Cl)c1] | 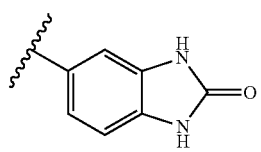 [SMILES: *c1ccc2[nH]c(=O)[nH]c2c1] | H | 1.45 | 407.0 | 1H NMR: 400 MHZ, DMSO-d6: δ 4.40 (d, J = 6.40 Hz, 2H), 5.10 (s, 2H), 6.60 (dd, J = 2.40, 8.40 Hz, 1H), 6.65 (d, J = 2.40 Hz, 1H), 6.81 (d, J = 8.40 Hz, 1H), 7.34 (dd, J = 1.60, 8.40 Hz, 1H), 7.60-7.62 (m, 2H), 8.32 (t, J = 6.00 Hz, 1H), 10.43 (s, 1H), 10.58 (s, 1H) |
| 113 | 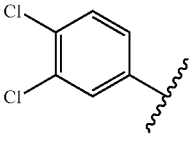 | 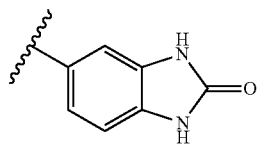 [SMILES: *c1ccc2[nH]c(=O)[nH]c2c1] | H | 1.86 | 394.0 | 1H NMR: 400 MHZ, DMSO-d6: δ 5.25 (s, 2H), 6.62-6.68 (m, 2H), 6.83 (d, J = 8.40 Hz, 1H), 7.47 (dd, J = 2.80, 9.00 Hz, 1H), 7.61 (d, J = 9.20 Hz, 1H), 7.88 (d, J = 2.40 Hz, 1H), 10.44 (s, 1H), 10.58 (s, 1H), 10.99 (s, 1H) |
| 114 | 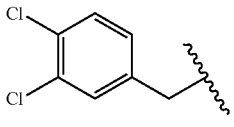 [SMILES: *Cc1ccc(Cl)c(Cl)c1] | 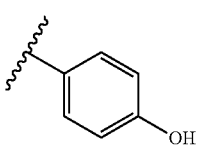 [SMILES: *c1ccc(O)cc1] | H | 1.78 | 368.0 | 1H NMR: 400 MHZ, DMSO-d6: δ 4.39 (d, J = 6.00 Hz, 2H), 5.03 (s, 2H), 6.68 (dd, J = 2.00, 6.80 Hz, 2H), 6.84 (dd, J = 2.00, 6.60 Hz, 2H), 7.34 (dd, J = 1.60, 8.40 Hz, 1H), 7.61 (t, J = 2.40 Hz, 2H), 8.30 (t, J = 6.00 Hz, 1H), 9.03 (s, 1H) |
| 115 | 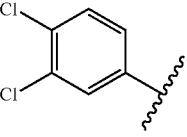 | 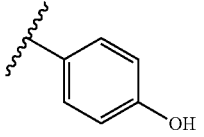 [SMILES: *c1ccc(O)cc1] | H | 1.78 | 352.0 | 1H NMR: 400 MHZ, DMSO-d6: δ 5.18 (s, 2H), 6.70 (d, J = 9.20 Hz, 2H), 6.88 (d, J = 8.00 Hz, 2H), 7.46 (dd, J = 2.40, 8.80 Hz, 1H), 7.60 (d, J = 8.80 Hz, 1H), 7.88 (d, J = 2.80 Hz, 1H), 9.06 (s, 1H), 10.98 (s, 1H) |
| 116 | 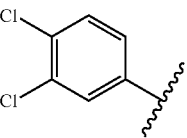 [SMILES: *c1ccc(Cl)c(Cl)c1] | 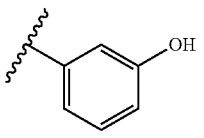 [SMILES: *c1cccc(O)c1] | H | 1.86 | 352.0 | 1H NMR: 400 MHz, DMSO-d6: δ 5.24 (s, 2H), 6.42-6.51 (m, 3H), 7.09 (t, J = 8.40 Hz, 1H), 7.47 (dd, J = 2.80, 8.80 Hz, 1H), 7.60 (d, J = 8.80 Hz, 1H), 7.88 (d, J = 2.40 Hz, 1H), 9.54 (s, 1H) |
| 117 | 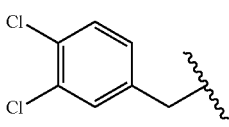 [SMILES: *Cc1ccc(Cl)c(Cl)c1] | 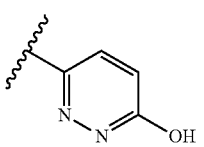 [SMILES: *c1ccc(O)nn1] | H | 1.61 | 368.3 | 1H NMR: 400 MHZ, MeOD: δ 4.46 (s, 2H), 5.28 (s, 2H), 7.00 (d, J = 10.00 Hz, 1H), 7.25 (d, J = 10.00 Hz, 1H), 7.31 (dd, J = 2.00, 8.00 Hz, 1H), 7.50 (d, J = 8.40 Hz, 1H), 7.54 (d, J = −6.00 Hz, 1H) |

-continued

| Ex | R1 | R2 | R3 | LCMS RT (min) | LCMS Ion [M + H]+ | 1H NMR |
|---|---|---|---|---|---|---|
| 118 | 3,4-dichlorophenyl-CH2- | 6-(3-hydroxypyridazinyl)- | H | 1.66 | 353.7 | 1H NMR: 400 MHZ, DMSO-d6: δ 5.35 (s, 2H), 6.94 (d, J = 10.00 Hz, 1H), 7.27 (d, J = 9.60 Hz, 1H), 7.48 (dd, J = 2.80, 8.80 Hz, 1H), 7.61 (d, J = 8.80 Hz, 1H), 7.88 (d, J = 2.40 Hz, 1H), 10.99 (s, 1H), 12.32 (s, 1H) |
| 119 | 3,4-dichlorophenyl-CH2- | 3,5-difluoro-4-hydroxyphenyl- | H | 1.85 | 387.5 | 1H NMR: 400 MHZ, DMSO-d6: δ 5.27 (s, 2H), 6.26 (s, 1H), 6.87 (dd, J = 7.20, 17.20 Hz, 2H), 7.47 (dd, J = 2.80, 8.80 Hz, 1H), 7.61 (d, J = 8.80 Hz, 1H), 7.89 (d, J = 2.40 Hz, 1H) |
| 120 | 3,4-dichlorophenyl-CH2- | 6-(1,2,3,4-tetrahydroquinolinyl)- | H | 1.60 | 407.0 | 1H NMR: 400 MHZ, MeOD: δ 1.89 (m, 4H), 2.72 (t, J = 6.40 Hz, 2H), 3.20 (dd, J = 5.60, 6.80 Hz, 1H), 4.45 (s, 2H), 4.99 (s, 2H), 6.50 (d, J = 9.20 Hz, 1H), 6.64 (m, 2H), 7.30 (dd, J = 2.00, 8.00 Hz, 1H), 7.50 (d, J = 8.40 Hz, 1H), 7.55 (d, J = 2.00 Hz, 1H) |
| 121 | 3,4-dichlorophenyl-CH2- | 6-(3,4-dihydroquinolin-2(1H)-one)- | H | 1.85 | 387.5 | 1H NMR: 400 MHZ, MeOD-d4: δ 2.09-2.11 (m, 2H), 2.95 (t, J = 6.80 Hz, 2H), 3.48 (t, J = 5.60 Hz, 2H), 5.29 (s, 2H) 7.03-7.05 (m, 2H), 7.17 (d, J = 9.60 Hz, 1H), 7.43 (d, J = 8.80 Hz, 1H), 7.49 (d, J = 8.80 Hz, 1H), 7.84 (d, J = 2.80 Hz, 1H) |
| 122 | 3,4-dichlorophenyl-CH2- | 6-(1-methyl-3,4-dihydroquinolin-2(1H)-one)- | H | 1.85 | 370.0 | 1H NMR: 400 MHZ, DMSO-d6: δ 2.50 (t, J = 7.20 Hz, 2H), 2.82 (t, J = 8.00 Hz, 2H), 3.22 (s, 3H), 4.39 (d, J = 6.00 Hz, 2H), 5.14 (s, 2H), 6.91-6.92 (m, 2H), 7.02 (d, J = 8.40 Hz, 1H), 7.34 (dd, J = 2.00, 8.40 Hz, 1H), 7.60-7.61 (m, 2H), 8.32 (t, J = 6.00 Hz, 1H) |
| 123 | 3,4-dichlorophenyl-CH2- | 6-(quinoxalin-2(1H)-one)- | H | 1.88 | 406.0 | 1H NMR: 400 MHz, DMSO-d6: δ 5.42 (s, 2H), 7.27-7.34 (m, 2H), 7.47 (dd, J = 2.80, 8.80 Hz, 1H), 7.53 (d, J = 2.80 Hz, 1H), 7.61 (d, J = 8.80 Hz, 1H), 7.88 (d, J = 2.40 Hz, 1H), 8.19 (d, J = 2.40 Hz, 1H), 11.01 (s, 1H), 12.38 (s, 1H) |
| 124 | 4-(trifluoromethyl)phenyl-CH2- | 6-(quinoxalin-2(1H)-one)- | H | 1.79 | 404.0 | 1H NMR: 400 MHz, DMSO-d6: δ 5.43 (s, 2H), 6.52-7.35 (m, 2H), 7.54 (d, J = 2.40 Hz, 1H), 7.72 (d, J = 9.20 Hz, 2H), 7.76 (d, J = 9.20 Hz, 2H), 8.20 (d, J = 2.00 Hz, 1H), 11.11 (s, 1H), 12.39 (s, 1H) |

| Ex | R1 | R2 | R3 | LCMS RT (min) | LCMS Ion [M + H]+ | 1H NMR |
|---|---|---|---|---|---|---|
| 125 | 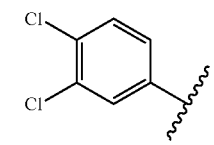 [SMILES: *c1ccc(Cl)c(Cl)c1] | 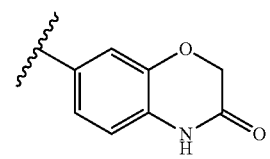 [SMILES: *c1ccc2c(c1)OCC(=O)N2] | H | 1.90 | 409.0 | 1H NMR: 400 MHz, DMSO-d6: δ 4.55 (s, 2H), 5.27 (s, 2H), 6.68 (dd, J = 2.40, 8.60 Hz, 1H), 6.75 (d, J = 2.40 Hz, 1H), 6.83 (d, J = 8.80 Hz, 1H), 7.48 (dd, J = 2.40, 8.80 Hz, 1H), 7.62 (d, J = 8.80 Hz, 1H), 7.89 (d, J = 2.40 Hz, 1H), 10.59 (s, 1H), 11.01 (s, 1H) |
| 126 | 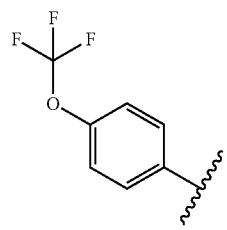 [SMILES: *c1ccc(OC(F)(F)F)cc1] | 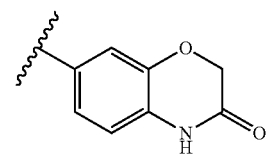 [SMILES: *c1ccc2c(c1)OCC(=O)N2] | H | 1.84 | 423.0 | 1H NMR: 400 MHz, DMSO-d6: δ 4.55 (s, 2H), 5.25 (s, 2H), 6.68 (dd, J = 2.80, 8.80 Hz, 1H), 6.76 (d, J = 2.40 Hz, 1H), 6.83 (d, J = 8.40 Hz, 1H), 7.38 (d, J = 8.40 Hz, 1H), 7.66 (dd, J = 2.40, 7.00 Hz, 1H), 10.59 (s, 1H), 10.84 (s, 1H) |
| 127 | 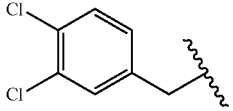 [SMILES: *Cc1ccc(Cl)c(Cl)c1] | 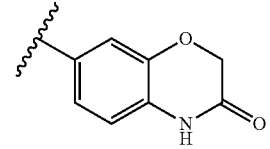 [SMILES: *c1ccc2c(c1)OCC(=O)N2] | H | 1.83 | 423.0 | 1H NMR: 400 MHz, DMSO-d6: δ 4.39 (d, J = 6.00 Hz, 2H), 4.54 (s, 2H), 5.11 (s, 2H), 6.63 (d, J = 2.80 Hz, 1H), 6.70 (d, J = 2.40 Hz 1H), 6.81 (d, J = 8.80 Hz, 1H), 7.34 (dd, J = 2.00, 8.40 Hz, 1H), 7.60-7.61 (m, 2H), 8.33 (t, J = 6.00 Hz, 1H), 10.56 (s, 1H) |

Example 128

4-(2-(5-(3,4-dichlorobenzylamino)-1,3,4-oxadiazol-2-yl)ethyl)phenol

N-(3,4-dichlorobenzyl)-2-(3-(4-hydroxyphenyl)propanoyl)hydrazinecarbothioamide

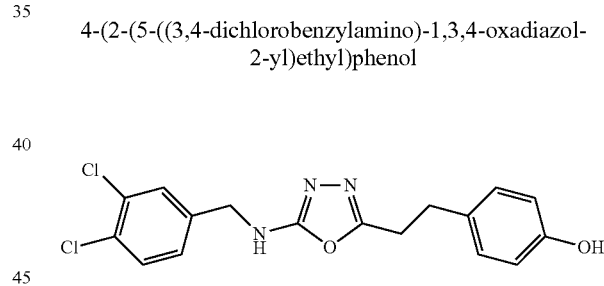

By a procedure analogous to the preparation of N-(4-chlorophenyl)-2-(2-(2-oxo-1,2,3,4-tetrahydroquinolin-6-yloxy)acetyl)hydrazinecarbothioamide, N-(3,4-dichlorobenzyl)-2-(3-(4-hydroxyphenyl)propanoyl)hydrazinecarbothioamide (0.24 g, 52%) was synthesized. LCMS: RT 1.69 min. LCMS (ES-API), m/z 398.0 (M+H).

4-(2-(5-((3,4-dichlorobenzylamino)-1,3,4-oxadiazol-2-yl)ethyl)phenol

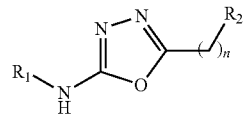

By a procedure analogous to the preparation of 6-((5-(4-chlorophenylamino)-1,3,4-oxadiazol-2-yl)methoxy)-3,4-dihydroquinolin-2(1H)-one, 4-(2-(5-((3,4-dichlorobenzylamino)-1,3,4-oxadiazol-2-yl)ethyl)phenol (0.165 g, 81%) was synthesized. 1H NMR: 400 MHZ, MeOD: δ 2.93-2.94 (m, 4H), 4.41 (s, 2H), 6.70 (dd, J=2.00, 6.40 Hz, 2H), 6.99 (dd, J=2.00, 6.40 Hz, 2H), 7.28 (dd, J=2.00, 8.40 Hz, 1H), 7.52 (dd, J=8.40, 10.80 Hz, 2H). LCMS: RT 1.81 min. LCMS (ES-API), m/z 366.0 (M+H).

The following compounds were synthesized by methods similar to that described for 4-(2-(5-(3,4-dichlorobenzylamino)-1,3,4-oxadiazol-2-yl)ethyl)phenol.

| Ex | R1 | R2 | n | LCMS RT (min) | LCMS Ion [M+H]+ | 1H NMR |
|---|---|---|---|---|---|---|
| 129 | 4-Cl-phenyl | 3,4-dihydroquinolin-2(1H)-on-6-yl | 2 | 1.711 | 369.0 | 400 MHz, DMSO-d6: δ 2.42 (q, J = 7.20 Hz, 2H), 2.83 (t, J = 7.60 Hz, 2H), 2.92 (t, J = 7.60 Hz, 2H), 3.04 (t, J = 7.60 Hz, 2H), 6.77 (d, J = 8.00 Hz, 1H), 7.02 (dd, J = 2.00, 8.00 Hz, 1H), 7.08 (s, 1H), 7.39 (dd, J = 2.00, 9.40 Hz, 2H), 7.55 (dd, J = 2.80, 9.40 Hz, 2H), 10.00 (s, 1H), 10.54 (s, 1H) |
| 130 | 4-CF3-phenyl | 3,4-dihydroquinolin-2(1H)-on-6-yl | 2 | 1.787 | 403.0 | 400 MHz, DMSO-d6: δ 2.43 (q, J = 7.60 Hz, 2H), 2.84 (t, J = 8.00 Hz, 2H), 2.94 (t, J = 7.60 Hz, 2H), 3.07 (t, J = 7.60 Hz, 2H), 6.78 (d, J = 8.00 Hz, 1H), 7.03 (dd, J = 2.00, 8.00 Hz, 1H), 7.09 (s, 1H), 7.71 (q, J = 9.60 Hz, 4H), 10.01 (s, 1H), 10.87 (s, 1H) |
| 131 | 3,4-diCl-phenyl | 3,4-dihydroquinolin-2(1H)-on-6-yl | 2 | 1.867 | 403.0 | 400 MHz, DMSO-d6: δ 2.42 (q, J = 7.20 Hz, 2H), 2.83 (t, J = 7.60 Hz, 2H), 2.92 (t, J = 7.20 Hz, 2H), 3.05 (t, J = 7.60 Hz, 2H), 3.51 (s, 1H), 6.77 (d, J = 8.00 Hz, 1H), 7.02 (d, J = 8.00 Hz, 1H), 7.08 (s, 1H), 7.44 (d, J = 9.20 Hz, 1H), 7.57 (d, J = 7.60 Hz, 1H), 7.87 (d, J = 2.40 Hz, 1H), 10.00 (s, 1H), 10.77 (s, 1H) |
| 132 | 3,4-diCl-benzyl | 3,4-dihydroquinolin-2(1H)-on-6-yl | 2 | 1.758 | 417.0 | 400 MHz, DMSO-d6: δ 2.41 (t, J = 7.20 Hz, 2H), 2.74-2.86 (m, 5H), 2.91 (d, J = 7.60 Hz, 2H), 3.17 (d, J = 5.20 Hz, 1H), 3.51 (s, 1H), 4.35 (d, J = 6.40 Hz, 2H), 6.75 (d, J = 8.00 Hz, 1H), 6.96 (d, J = 8.00 Hz, 1H), 7.01 (s, 1H), 7.33 (dd, J = 1.60, 8.20 Hz, 1H), 7.59-7.62 (m, 2H), 8.03 (t, J = 6.00 Hz, 1H), 9.99 (s, 1H) |

-continued

| Ex | R1 | R2 | n | LCMS RT (min) | LCMS Ion [M + H]+ | 1H NMR |
|---|---|---|---|---|---|---|
| 133 | 4-(difluoromethoxy)phenyl | 3,4-dihydroquinolin-2(1H)-one-6-yl | 2 | 1.689 | 401.0 | 400 MHz, DMSO-d6: δ 2.43 (q, J = 7.60 Hz, 2H), 2.84 (t, J = 8.00 Hz, 2H), 2.93 (t, J = 7.20 Hz, 2H), 3.04 (t, J = 7.60 Hz, 2H), 6.78 (d, J = 8.00 Hz, 1H), 6.94-7.31 (m, 5H), 7.54-7.58 (m, 2H), 10.01 (s, 1H), 10.44 (s, 1H) |
| 134 | 4-(trifluoromethoxy)phenyl | 3,4-dihydroquinolin-2(1H)-one-6-yl | 2 | 1.893 | 419.0 | 400 MHz, DMSO-d6: δ 2.43 (q, J = 7.20 Hz, 2H), 2.84 (t, J = 7.60 Hz, 2H), 2.93 (t, J = 7.20 Hz, 2H), 3.05 (t, J = 7.60 Hz, 2H), 6.78 (d, J = 8.00 Hz, 1H), 7.03 (d, J = 8.00 Hz, 1H), 7.08 (s, 1H), 7.35 (d, J = 8.40 Hz, 2H), 7.63 (dd, J = 2.40, 6.80 Hz, 2H), 10.01 (s, 1H), 10.61 (s, 1H) |
| 135 | 4-chloro-3-fluorophenyl | 3,4-dihydroquinolin-2(1H)-one-6-yl | 2 | 1.846 | 387.0 | 400 MHz, DMSO-d6: δ 2.43 (q, J = 7.20 Hz, 2H), 2.84 (t, J = 8.00 Hz, 2H), 2.93 (t, J = 7.20 Hz, 2H), 3.05 (t, J = 7.60 Hz, 2H), 6.77 (d, J = 8.40 Hz, 1H), 7.02 (dd, J = 2.00, 8.00 Hz, 1H), 7.08 (s, 1H), 7.30 (dd, J = 1.60, 9.00 Hz, 1H), 7.53 (t, J = 8.80 Hz, 1H), 7.65 (dd, J = 2.80, 11.80 Hz, 1H), 10.00 (s, 1H), 10.82 (s, 1H) |
| 136 | 3,4-dichlorophenyl | quinolin-2(1H)-one-6-yl | 2 | 1.798 | 401.0 | 400 MHz, DMSO-d6: δ 3.09 (dd, J = 6.80, 22.20 Hz, 4H), 6.48 (dd, J = 2.00, 9.60 Hz, 1H), 7.24 (d, J = 8.40 Hz, 1H), 7.42 (dd, J = 2.00, 8.60 Hz, 1H), 7.52-7.54 (m, 3H), 7.83-7.88 (m, 2H), 10.85 (s, 1H), 11.68 (s, 1H) |
| 137 | 3-chloro-4-(trifluoromethoxy)phenyl | quinolin-2(1H)-one-6-yl | 2 | 1.934 | 451.0 | 400 MHz, DMSO-d6: δ 3.10 (dd, J = 6.80, 22.80 Hz, 4H), 6.48 (dd, J = 2.00, 9.60 Hz, 1H), 7.24 (d, J = 8.40 Hz, 1H), 7.42 (dd, J = 2.00, 8.40 Hz, 1H), 7.50-7.57 (m, 3H), 7.83-7.89 (m, 2H), 10.87 (s, 1H), 11.71 (s, 1H) |

-continued
| Ex | R1 | R2 | n | LCMS RT (min) | LCMS Ion [M + H]+ | 1H NMR |
|---|---|---|---|---|---|---|
| 138 | 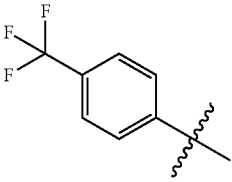 [SMILES: *c1ccc(C(F)(F)F)cc1] | 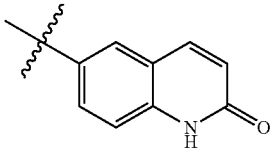 [SMILES: *c1ccc2[nH]c(=O)ccc2c1] | 2 | 1.547 | 399.0 | 400 MHz, DMSO-d6: δ 3.11 (dd, J = 6.80, 21.00 Hz, 4H), 6.48 (dd, J = 2.00, 9.60 Hz, 1H), 7.25 (d, J = 8.80 Hz, 1H), 7.43 (dd, J = 2.00, 8.40 Hz, 1H), 7.56 (d, J = 1.20 Hz, 1H), 7.70 (t, J = 10.00 Hz, 4H), 7.85 (d, J = 9.60 Hz, 1H), 10.86 (s, 1H), 11.69 (s, 1H) |
| 139 | 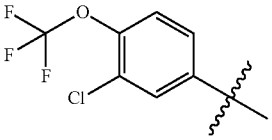 [SMILES: *c1ccc(OC(F)(F)F)c(Cl)c1] | 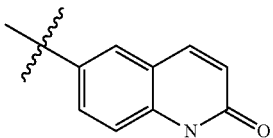 | 2 | 1.565 | 431.0 | 400 MHz, DMSO-d6: δ 3.04-3.19 (m, 4H), 6.48 (d, J = 9.60 Hz, 1H), 6.97-7.46 (m, 5H), 7.55 (d, J = 1.60 Hz, 1H), 7.81-7.86 (m, 2H), 10.70 (s, 1H), 11.69 (s, 1H) |
| 140 | 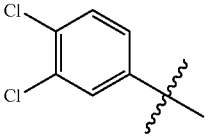 | 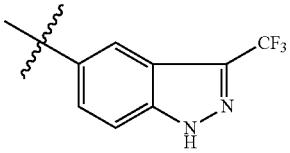 [SMILES: *c1ccc2[nH]nc(C(F)(F)F)c2c1] | 3 | 2.068 | 456.25 | 400 MHz, MeOD: δ 1.49 (d, J = 6.80 Hz, 3H), 3.15-3.18 (m, 2H), 3.47-3.53 (m, 2H), 7.31 (dd, J = 2.40, 8.80 Hz, 1H), 7.41 (d, J = 8.80 Hz, 1H), 7.46 (dd, J = 1.60, 8.80 Hz, 1H), 7.60-7.65 (m, 2H), 7.71 (d, J = 2.80 Hz, 1H) |
| 141 | 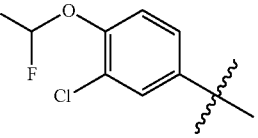 | 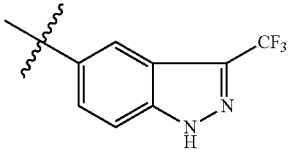 [SMILES: *c1ccc2[nH]nc(C(F)(F)F)c2c1] | 3 | 1.914 | 483.25 | 400 MHz, MeOD: δ 1.49 (d, J = 7.20 Hz, 3H), 3.15-3.18 (m, 2H), 3.46-3.51 (m, 1H), 6.76 (t, J = 147.60 Hz, 1H), 7.22 (d, J = 8.80 Hz, 1H), 7.34 (dd, J = 2.80, 8.80 Hz, 1H), 7.47 (dd, J = 1.60, 8.80 Hz, 1H), 7.60-7.67 (m, 3H) |
| 142 | 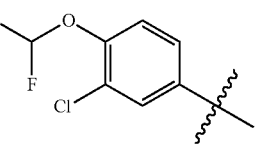 | 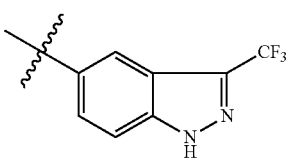 [SMILES: *c1ccc2[nH]nc(C(F)(F)F)c2c1] | 2 | 1.935 | 474.0 | 400 MHz, DMSO-d6: δ 2.39-2.47 (m, 4H), 5.97 (t, J = 147.20 Hz, 1H), 6.45 (d, J = 9.20 Hz, 1H), 6.57-6.63 (m, 2H), 6.80 (d, J = 8.40 Hz, 1H), 6.86 (s, 1H), 6.92 (d, J = 2.40 Hz, 1H) |
| 143 | 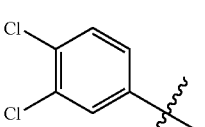 | 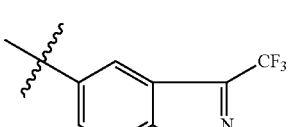 | 2 | 2.036 | 442.0 | 400 MHz, MeOD: δ 3.18-3.24 (m, 4H), 7.36 (dd, J = 2.40, 8.80 Hz, 1H), 7.41-7.46 (m, 2H), 7.60 (dd, J = 0.80, 8.60 Hz, 1H), 7.66 (s, 1H), 7.77 (d, J = 2.40 Hz, 1H) |

| Ex | R1 | R2 | n | LCMS RT (min) | LCMS Ion [M + H]+ | 1H NMR |
|---|---|---|---|---|---|---|
| 144 | F₃C-phenyl | 1H-indazol-5-yl | 2 | 1.635 | 372 [M − H]⁻ | 400 MHz, DMSO-d6: δ 3.14 (d, J = 3.60 Hz, 4H), 7.27 (d, J = 8.40 Hz, 1H), 7.47 (d, J = 8.40 Hz, 1H), 7.62-7.72 (m, 5H), 7.99 (s, 1H), 10.88 (s, 1H), 12.98 (s, 1H) |
| 145 | 3,4-dichlorophenyl | 1H-indazol-5-yl | 3 | 1.955 | 386 [M − H]⁻ | 400 MHz, DMSO-d6: δ 1.99-2.09 (m, 2H), 2.79 (t, J = 14.80 Hz, 4H), 7.24 (d, J = 7.60 Hz, 1H), 7.45-7.49 (m, 2H), 7.57-7.61 (m, 2H), 7.90 (d, J = 2.40 Hz, 1H), 7.99 (s, 1H), 10.78 (s, 1H), 12.96 (s, 1H) |
| 146 | 4-chloro-3-fluorophenyl | 1H-indazol-5-yl | 3 | 1.923 | 370 [M − H]⁻ | 400 MHz, DMSO-d6: δ 2.01-2.05 (m, 2H), 2.79 (t, J = 15.20 Hz, 4H), 7.23 (d, J = 1.60 Hz, 1H), 7.26 (d, J = 1.20 Hz, 1H), 7.31-7.34 (m, 1H), 7.48 (d, J = 8.40 Hz, 1H), 7.52-7.57 (m, 1H), 7.66-7.69 (m, 1H), 7.99 (s, 1H), 10.81 (s, 1H), 12.96 (s, 1H) |
| 147 | 3,4-dichlorophenyl | 3-hydroxyphenyl | 1 | 1.78 | 338.0 | 400 MHZ, DMSO-d6: δ 4.10 (s, 2H), 6.67-6.74 (m, 3H), 7.15 (t, J = 7.60 Hz, 1H), 7.45 (dd, J = 2.40, 8.80 Hz, 1H), 7.59 (d, J = 8.80 Hz, 1H), 7.87 (d, J = 2.80 Hz, 1H), 9.47 (s, 1H), 10.83 (s, 1H) |
| 148 | 3,4-dichlorobenzyl | 3-hydroxyphenyl | 1 | 1.62 | 351.0 | 400 MHZ, DMSO-d6: δ 3.96 (s, 2H), 4.34 (d, J = 6.40 Hz, 2H), 6.65-6.67 (m, 3H), 7.10-7.10 (m, 1H), 7.32 (dd, J = 2.40, 8.20 Hz, 1H), 7.59-7.61 (m, 2H), 8.08 (t, J = 6.00 Hz, 1H), 9.44 (s, 1H) |
| 149 | 3,4-dichlorophenyl | 4-hydroxyphenyl | 1 | 1.75 | 337.0 | 400 MHZ, DMSO-d6: δ 4.05 (s, 2H), 6.74 (dd, J = 2.00, 6.80 Hz, 2H), 7.11 (d, J = 8.80 Hz, 2H), 7.44 (dd, J = 2.80, 9.00 Hz, 1H), 7.58 (d, J = 8.80 Hz, 1H), 7.86 (d, J = 2.40 Hz, 1H), 9.37 (s, 1H), 10.77 (s, 1H) |

-continued

| Ex | R1 | R2 | n | LCMS RT (min) | LCMS Ion [M+H]+ | 1H NMR |
|---|---|---|---|---|---|---|
| 150 | 3,4-dichlorobenzyl | 4-hydroxyphenyl | 1 | 1.63 | 351.0 | 400 MHZ, DMSO-d6: δ 3.91 (s, 2H), 4.33 (d, J = 6.00 Hz, 2H), 6.27 (s, 1H), 6.71 (d, J = 8.80 Hz, 2H), 7.04 (d, J = 8.80 Hz, 2H), 7.31 (dd, J = 2.00, 8.40 Hz, 1H), 7.59 (d, J = 8.40 Hz, 2H), 8.02 (t, J = 6.40 Hz, 1H), 9.37 (s, 1H). |
| 151 | 3,4-dichlorophenyl | 4-hydroxyphenyl | 2 | 1.91 | 352.0 | 400 MHZ, MeOD: δ 2.97-3.09 (m, 4H), 6.72 (dd, J = 2.00, 6.40 Hz, 2H), 7.05 (d, J = 8.40 Hz, 2H), 7.38 (dd, J = 2.80, 8.80 Hz, 1H), 7.46 (d, J = 8.80 Hz, 1H), 7.79 (d, J = 2.40 Hz, 1H) |
| 152 | 4-(trifluoromethyl)phenyl | 4-hydroxyphenyl | 2 | 1.78 | 350.0 | 400 MHz, DMSO-d6: δ 2.91 (t, J = 7.6 Hz, 2H), 3.04 (t, J = 7.60 Hz, 2H), 6.68 (d, J = 2.00 Hz, 1H), 6.69 (d, J = 2.00 Hz, 1H), 7.06 (d, J = 2.00 Hz, 1H), 7.71 (s, 4H), 9.21 (s, 1H), 10.86 (s, 1H) |
| 153 | 4-(trifluoromethoxy)phenyl | 4-hydroxyphenyl | 2 | 1.808 | 366.0 | 400 MHz, DMSO-d6: δ 2.91 (t, J = 7.60 Hz, 2H), 3.01 (t, J = 7.60 Hz, 2H), 6.67-6.70 (m, 2H), 7.05 (d, J = 8.40 Hz, 2H), 7.35 (d, J = 8.40 Hz, 2H), 7.60-7.64 (m, 2H), 9.21 (s, 1H), 10.6 (s, 1H) |

Example 154
6-(2-(5-((4-(trifluoromethyl)phenyl)amino)-1,3,4-oxadiazol-2-yl)cyclopropyl)quinolin-2(1H)-one
6-bromo-1-(4-methoxybenzyl)quinolin-2(1H)-one

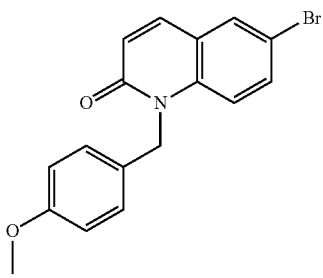 [SMILES: COc1ccc(Cn2c(=O)ccc3cc(Br)ccc32)cc1]

To a stirred solution of 6-bromoquinolin-2(1H)-one (2 g, 8.92 mmol) in DMF (20 mL) was added NaH (0.26 g, 10.7 mmol) at 0° C. After stirring for 30 min, 1-(chloromethyl)-4-methoxybenzene (1.67 g, 10.7 mmol) was added and the resulting reaction mixture was stirred at RT overnight. The reaction mixture was diluted with water and the precipitate was filtered, washed with water and dried. The crude product was purified by flash chromatography on silica gel using hexane/ethyl acetate to give 6-bromo-1-(4-methoxybenzyl)quinolin-2(1H)-one as yellow solid (2.4 g, 80%). 1HNMR: 400 MHz, DMSO-d6: δ 3.70 (s, 3H), 5.43 (s, 2H), 6.78 (d, J=9.60 Hz, 1H), 6.87 (dd, J=2.00, 6.40 Hz, 2H), 7.14 (d, J=8.80 Hz, 2H), 7.38 (d, J=8.80 Hz, 1H), 7.66 (dd, J=2.40, 8.80 Hz, 1H), 7.94 (d, J=-8.40 Hz, 1H), 8.01 (d, J=2.40 Hz, 1H).

(E)-ethyl 3-(1-(4-methoxybenzyl)-2-oxo-1,2-dihydroquinolin-6-yl)acrylate

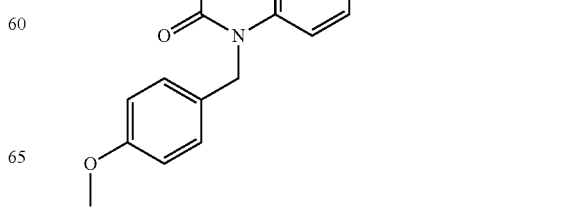

To a stirred solution of 6-bromo-1-(4-methoxybenzyl)quinolin-2(1H)-one (1 g, 2.9 mmol) in DMF (10 mL) were added potassium carbonate (1.19 g, 8.69 mmol), n-tert butyl ammonium chloride (0.66 g, 2.9 mmol), ethyl acrylate (1.16 g, 11.6 mmol) and palladium acetate (0.65 g, 2.9 mmol). The reaction mixture was stirred at room temperature for 20 min, then heated to 120° C. overnight. The reaction mixture was concentrated. To this, was added water and extracted with ethyl acetate, and the combined organic layer was dried over sodium sulfate and concentrated. The crude product was purified by flash chromatography on silica gel using hexane/ethyl acetate to give (E)-ethyl 3-(1-(4-methoxybenzyl)-2-oxo-1,2-dihydroquinolin-6-yl)acrylate as a white solid (0.8 g, 80%).

Ethyl 2-(1-(4-methoxybenzyl)-2-oxo-1,2-dihydroquinolin-6-yl)cyclopropanecarboxylate

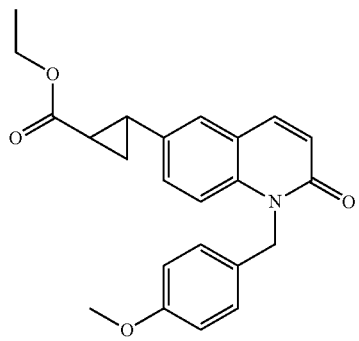 [SMILES: CCOC(=O)C1CC1c1ccc2c(ccc(=O)n2Cc2ccc(OC)cc2)c1]

To a stirred solution of (E)-ethyl 3-(1-(4-methoxybenzyl)-2-oxo-1,2-dihydroquinolin-6-yl)acrylate (1.2 g, 3.21 mmol) in diethyl ether (50 mL) was added palladium (II) acetate (0.031 g, 0.138 mmol). The reaction mixture was cooled to −10° C., and a cold solution of diazomethane (1.351 g, 32.1 mmol) in ether (generated from aqueous KOH (8 g, 143 mmol) and 1-methyl-1-nitrosourea (4 g, 38.8 mmol) at −15° C.) was added. The reaction mixture was stirred at room temperature for 12 h. The reaction mixture was filtered through celite, diluted with diethyl ether, and washed with water and saturated NaCl solution. The organic layer was dried over sodium sulfate, concentrated, and purified by flash chromatography on silica gel column using 15% ethyl acetate in hexane to give ethyl 2-(1-(4-methoxybenzyl)-2-oxo-1,2-dihydroquinolin-6-yl)cyclopropanecarboxylate as a yellow gum (510 mg, 57%). 1H NMR 400 MHz, CDCl3: δ 1.29 (t, J=4.80 Hz, 3H), 1.31 (d, J=4.80 Hz, 1H), 1.62 (d, J=4.80 Hz, 1H), 1.84-1.89 (m, 1H), 2.51-2.56 (m, 1H), 3.76 (d, J=2.80 Hz, 3H), 3.98 (q, J=174.00 Hz, 2H), 5.47 (s, 2H), 6.77-6.83 (m, 3H), 7.13-7.28 (m, 5H), 7.66 (d, J=9.60 Hz, 1H).

6-(2-(5-((4-(trifluoromethyl)phenyl)amino)-1,3,4-oxadiazol-2-yl)cyclopropyl)quinolin-2(1H)-one

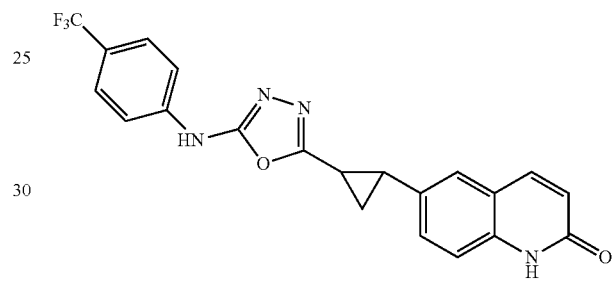

To a stirred solution of 1-(4-methoxybenzyl)-6-(2-(5-((4-(trifluoromethyl)phenyl)amino)-1,3,4-oxadiazol-2-yl)cyclopropyl)quinolin-2(1H)-one (35 mg, 0.065 mmol) in DCM (5 mL) was added TFA (0.5 mL, 6.49 mmol) and stirred at room temperature overnight. The solvent was concentrated to give a crude product, purified by preparative HPLC on a Sunfire C18 column (150×19, 5μ) using a gradient of 0-100% ACN in 0.1% TFA to give trans-6-(2-(5-((4-(trifluoromethyl)phenyl)amino)-1,3,4-oxadiazol-2-yl)cyclopropyl)quinolin-2(1H)-one. 1H NMR 400 MHz, MeOD: δ 1.65-1.79 (m, 2H), 2.43-2.47 (m, 1H), 2.70-2.75 (m, 1H), 6.64 (d, J=9.20 Hz, 1H), 7.35 (d, J=8.80 Hz, 1H), 7.47 (dd, J=2.00, 8.60 Hz, 1H), 7.57 (d, J=1.60 Hz, 1H), 7.68 (dd, J=8.80, 23.20 Hz, 4H), 7.97 (d, J=9.20 Hz, 1H). LCMS, RT 1.869 min; LCMS (ES-API), m/z 412.11.

Example 155 was synthesized by a procedure analogous to that used in Example 154.

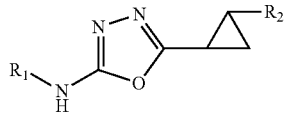

| Ex | R1 | R2 | LCMS RT (min) | LCMS Ion [M + H]+ | 1H NMR |
|---|---|---|---|---|---|
| 155 | ![R1 structure with F, O, CF2H, Cl on phenyl] | ![R2 quinolin-2-one] | 1.873 | 445.0 | 400 MHz, (METHANOL-d₄) δ ppm 1.65-1.81 (m, 2H) 2.39-2.47 (m, 1H) 2.71 (ddd, J = 9.16, 6.15, 4.77 Hz, 1H) 6.59-6.98 (m, 2H) 7.25-7.39 (m, 2H) 7.41-7.51 (m, 2H) 7.57 (d, J = 2.01 Hz, 1H) 7.80 (d, J = 2.51 Hz, 1H) 7.96 (d, J = 9.54 Hz, 1H) |

Example 156

6-((3-(3,4-dichlorophenylamino)-1,2,4-oxadiazol-5-yl)methoxy)-3,4-dihydroquinolin-2(1H)-one

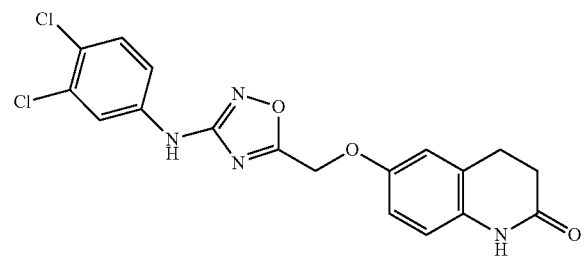 [SMILES: O=C1CCc2cc(OCc3nc(Nc4ccc(Cl)c(Cl)c4)no3)ccc2N1]

To a stirred solution of 2-(2-oxo-1,2,3,4-tetrahydroquinolin-6-yloxy)acetic acid (0.15 g, 0.67 mmol) were added HOBt (0.1 g, 0.74 mmol), EDC (0.15 g, 0.74 mmol) and DIPEA (0.22 g, 1.69 mmol). The resulting reaction mixture was stirred at room temperature for 30 min. (E)-1-(3,4-dichlorophenyl)-2-hydroxyguanidine (0.15 g, 0.67 mmol) in DMF was added to the above reaction mixture followed by sodium sulfate (0.48 g, 3.39 mmol) and the reaction mixture was heated at 110° C. for 12 h. The reaction mixture was concentrated under reduced pressure. Water was added and the mixture was extracted with ethyl acetate. The combined organic layer was dried over sodium sulfate and concentrated. Purification was by preparative HPLC to give 6-((3-(3,4-dichlorophenylamino)-1,2,4-oxadiazol-5-yl)methoxy)-3,4-dihydroquinolin-2(1H)-one (9.3 mg, 7%). ¹HNMR: 400 MHz, DMSO-d6: δ 2.42 (q, J=7.20 Hz, 2H), 2.85 (t, J=7.60 Hz, 2H), 5.41 (s, 2H), 6.78-6.87 (m, 2H), 6.94 (d, J=2.40 Hz, 1H), 7.41 (dd, J=2.80, 8.80 Hz, 1H), 7.59 (d, J=8.80 Hz, 1H), 7.71 (d, J=2.80 Hz, 1H), 9.96 (s, 1H), 10.39 (s, 1H). LCMS, RT 1.880 min; LCMS (ES-API), m/z 405.1.

The following compounds were synthesized by methods similar to that described for 6-((3-(3,4-dichlorophenylamino)-1,2,4-oxadiazol-5-yl)methoxy)-3,4-dihydroquinolin-2(1H)-one.

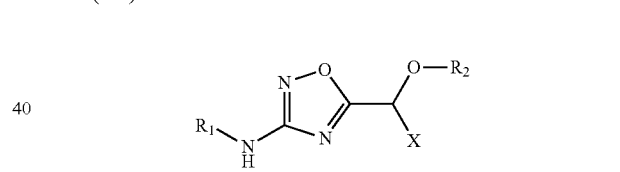

| Ex. | R1 | R2 | X | LCMS RT (min) | LCMS Ion [M + H]⁺ | 1H NMR |
|---|---|---|---|---|---|---|
| 157 | ![R1 with CF3, F on phenyl] | ![R2 quinolin-2-one] | H | 1.938 | 421.0 | 400 MHz, DMSO-d6: δ 5.54 (s, 2H), 6.52 (dd, J = 2.00, 9.60 Hz, 1H), 2.00 (d, J = 2.00 Hz, 2H), 7.39 (d, J = 8.40 Hz, 2H), 7.50 (d, J = 13.60 Hz, 1H), 7.74 (t, J = 8.80 Hz, 1H), 7.83 (d, J = 9.60 Hz, 1H), 10.76 (s, 1H), 11.68 (s, 1H) |

-continued

| Ex. | R1 | R2 | X | LCMS RT (min) | LCMS Ion [M + H]+ | 1H NMR |
|---|---|---|---|---|---|---|
| 158 | 4-F-phenyl | quinolin-2(1H)-one-6-yl | H | 2.284 | 351.0 | 400 MHz, DMSO-d6: δ 5.49 (s, 2H), 6.51 (dd, J = 2.00, 9.40 Hz, 1H), 7.15-7.20 (m, 2H), 7.29 (d, J = 1.60 Hz, 2H), 7.37 (s, 1H), 7.44-7.47 (m, 2H), 7.83 (d, J = 9.60 Hz, 1H), 10.00 (s, 1H), 11.68 (s, 1H) |
| 159 | 2,3-diCl-phenyl | quinolin-2(1H)-one-6-yl | H | 1.98 | 401.0 | 400 MHz, DMSO-d6: δ 5.49 (s, 2H), 6.52 (dd, J = 2.00, 9.60 Hz, 1H), 0.00 (d, J = 1.60 Hz, 2H), 7.36-7.41 (m, 3H), 7.77-7.85 (m, 2H), 9.43 (s, 1H), 11.70 (s, 1H) |
| 160 Rac | 4-Cl-3-F-phenyl | quinolin-2(1H)-one-6-yl | Me | 2.440 | 399.0 | 400 MHz, DMSO-d6: δ 1.75 (d, J = 6.40 Hz, 3H), 5.86 (q, J = 6.40 Hz, 1H), 6.49-6.52 (m, 1H), 7.23-7.29 (m, 3H), 7.35 (s, 1H), 7.43-7.55 (m, 2H), 7.81 (d, J = 9.60 Hz, 1H), 10.43 (s, 1H), 11.69 (s, 1H) |
| 161 | 3-Cl-phenyl | quinolin-2(1H)-one-6-yl | H | 1.797 | 368.77 | 400 MHz, DMSO-d6: δ 5.47 (s, 2H), 6.52 (d, J = 9.60 Hz, 1H), 7.09-7.13 (m, 1H), 7.28 (d, J = 1.60 Hz, 2H), 7.33-7.37 (m, 2H), 7.49 (dd, J = 1.20, 8.00 Hz, 1H), 7.77 (dd, J = 1.60, 8.20 Hz, 1H), 7.84 (d, J = 9.60 Hz, 1H), 9.13 (s, 1H), 11.68 (s, 1H) |

-continued
| Ex. | R1 | R2 | X | LCMS RT (min) | LCMS Ion [M + H]+ | 1H NMR |
|---|---|---|---|---|---|---|
| 162 Rac | 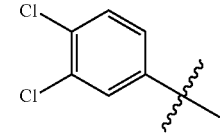 | 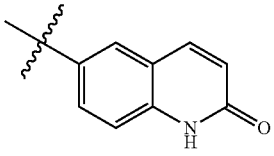 [SMILES: *c1ccc2[nH]c(=O)ccc2c1] | Me | 2.024 | 417.25 | 400 MHz, DMSO-d6: δ 1.74 (d, J = 6.40 Hz, 3H), 5.83-5.88 (m, 1H), 6.50 (dd, J = 2.00, 9.60 Hz, 1H), 7.26 (d, J = 1.20 Hz, 2H), 7.35-7.39 (m, 2H), 7.57 (d, J = 8.80 Hz, 1H), 7.67 (d, J = 2.40 Hz, 1H), 7.81 (d, J = 9.60 Hz, 1H), 10.38 (s, 1H), 11.67 (s, 1H) |
| 163 Rac | 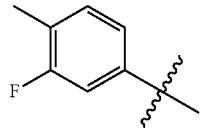 [SMILES: *c1ccc(C)c(F)c1] | 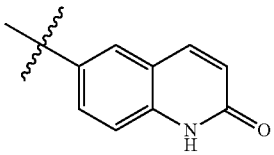 [SMILES: *c1ccc2[nH]c(=O)ccc2c1] | Me | 1.881 | 380.37 | 400 MHz, DMSO-d6: δ 1.74 (d, J = 6.40 Hz, 3H), 2.16 (d, J = 0.80 Hz, 3H), 5.82-5.87 (m, 1H), 6.50 (dd, J = 1.60, 9.60 Hz, 1H), 7.12 (dd, J = 2.40, 8.20 Hz, 1H), 7.18-7.29 (m, 4H), 7.35 (s, 1H), 7.81 (d, J = 9.60 Hz, 1H), 10.12 (s, 1H), 11.69 (s, 1H) |
| 164 | 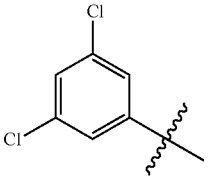 [SMILES: *c1cc(Cl)cc(Cl)c1] | 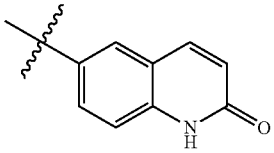 [SMILES: *c1ccc2[nH]c(=O)ccc2c1] | H | 2.063 | 403.0 | 400 MHz, MeOD: δ 3.93 (t, J = 10.40 Hz, 3H), 4.24 (dd, J = 2.00, 5.80 Hz, 2H), 4.29 (t, J = 10.40 Hz, 3H), 5.42 (s, 2H), 6.65 (d, J = 9.60 Hz, 1H), 7.02 (t, J = 3.60 Hz, 1H), 7.36-7.38 (m, 4H), 7.48 (d, J = 2.00 Hz, 2H), 7.65 (s, 1H), 7.72 (s, 1H), 7.96 (d, J = 9.60 Hz, 1H), 8.14 (s, 1H), 8.56 (s, 1H) |

-continued

| Ex. | R1 | R2 | X | LCMS RT (min) | LCMS Ion [M + H]+ | 1H NMR |
|---|---|---|---|---|---|---|
| 165 | 4-methylphenyl (isopropylidene linker) | 6-(quinolin-2(1H)-one) (isopropylidene linker) | H | 1.796 | 349.0 | 400 MHz, MeOD: δ 0.12 (s, 3H), 2.30 (s, 3H), 2.67 (s, 1H), 5.38 (s, 2H), 6.65 (d, J = 9.60 Hz, 1H), 7.12 (d, J = 8.40 Hz, 2H), 7.32-7.36 (m, 6H), 7.96 (d, J = 9.60 Hz, 1H) |
| 166 | 3-fluoro-4-methoxyphenyl (CH2 linker) | 6-(quinolin-2(1H)-one) | H | 1.839 | 383.0 | 400 MHz, DMSO-d6: δ 3.80 (s, 3H), 5.49 (s, 2H), 6.52 (d, J = 9.60 Hz, 1H), 7.13-7.37 (m, 6H), 7.83 (d, J = 9.60 Hz, 1H), 9.97 (s, 1H), 11.70 (s, 1H) |
| 167 | 3-chloro-4-methoxyphenyl (CH2 linker) | 6-(quinolin-2(1H)-one) | H | 1.874 | 399.0 | 400 MHz, DMSO-d6: δ 3.81 (s, 3H), 5.49 (s, 2H), 6.52 (d, J = 9.60 Hz, 1H), 7.15 (d, J = 9.20 Hz, 1H), 7.29 (d, J = 1.60 Hz, 2H), 7.35-7.38 (m, 2H), 7.53 (d, J = 2.40 Hz, 1H), 7.84 (d, J = 9.60 Hz, 1H), 9.96 (s, 1H), 11.70 (s, 1H) |
| 168 Rac | 3-chloro-4-methoxyphenyl (CH(Me) linker) | 6-(quinolin-2(1H)-one) (CH(Me) linker) | Me | 1.813 | 413.0 | 400 MHz, DMSO-d6: δ 1.73 (d, J = 6.40 Hz, 3H), 3.80 (s, 3H), 5.83 (d, J = 6.80 Hz, 1H), 6.50 (d, J = 9.60 Hz, 1H), 7.13 (d, J = 9.20 Hz, 1H), 7.26 (s, 2H), 7.34 (t, J = 11.20 Hz, 2H), 7.50 (d, J = 2.40 Hz, 1H), 7.81 (d, J = 12.00 Hz, 1H), 9.94 (s, 1H), 11.67 (s, 1H) |

| Ex. | R1 | R2 | X | LCMS RT (min) | LCMS Ion [M + H]+ | 1H NMR |
|---|---|---|---|---|---|---|
| 169 Rac | 3,5-dichlorophenyl | quinolin-2(1H)-on-6-yl | Me | 2.048 | 415.0 | 400 MHz, DMSO-d6: δ 1.74 (d, J = 6.40 Hz, 3H), 5.86 (q, J = 19.60 Hz, 1H), 6.50 (dd, J = 1.60, 9.60 Hz, 1H), 7.16 (t, J = 3.60 Hz, 1H), 7.26 (d, J = 1.60 Hz, 2H), 7.35 (d, J = 1.20 Hz, 1H), 7.44 (d, J = 2.00 Hz, 2H), 7.81 (d, J = 9.60 Hz, 1H), 10.49 (s, 1H), 11.67 (s, 1H) |
| 170 Rac | 4-chlorophenyl | quinolin-2(1H)-on-6-yl | Me | 1.846 | 384.0 | 400 MHz, DMSO-d6: δ 1.74 (d, J = 6.40 Hz, 3H), 5.84 (q, J = 19.60 Hz, 1H), 6.50 (d, J = 9.60 Hz, 2H), 7.26 (d, J = 1.20 Hz, 2H), 7.34-7.38 (m, 3H), 7.42-7.45 (m, 2H), 7.81 (d, J = 9.60 Hz, 1H), 10.15 (s, 1H), 11.67 (s, 1H) |
| 171 Rac | 4-(difluoromethoxy)-3-methylphenyl | 1H-indazol-5-yl | Me | 1.778 | 402.0 | 400 MHz, MeOD: δ 1.82 (d, J = 6.80 Hz, 3H), 2.27 (s, 3H), 5.66 (q, J = 19.60 Hz, 1H), 6.69 (t, J = 149.60 Hz, 1H), 7.05 (d, J = 8.40 Hz, 1H), 7.19 (dd, J = 2.40, 9.00 Hz, 1H), 7.28-7.34 (m, 3H), 7.50 (d, J = 9.20 Hz, 1H), 7.96 (s, 1H) |
| 172 rac | 3,4-dichlorophenyl | 1H-indazol-5-yl | Me | 1.11 | 388.15 [M − H]− | 400 MHz, MeOD: δ 1.81 (d, J = 6.80 Hz, 3H), 5.51 (s, 1H), 5.67 (q, J = 6.80 Hz, 1H), 7.26-7.35 (m, 3H), 7.40-7.47 (m, 2H), 7.69 (d, J = 2.40 Hz, 1H), 8.43 (s, 1H) |

-continued
| Ex. | R1 | R2 | X | LCMS RT (min) | LCMS Ion [M + H]+ | 1H NMR |
|---|---|---|---|---|---|---|
| 173 rac | 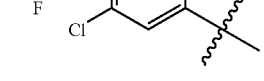 | 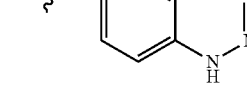 | Me | 2.027 | 420.0 [M − H]− | 400 MHz, DMSO-d6: δ 1.75 (d, J = 6.80 Hz, 3H), 5.83 (q, J = 19.60 Hz, 1H), 6.96-7.48 (m, 5H), 7.56 (d, J = 48.00 Hz, 1H), 7.62 (s, 1H), 7.97 (s, 1H), 10.29 (s, 1H), 12.98 (s, 1H) |
| 174 isomer A |  |  | Me | 1.935 | 390 | 400 MHz, MeOD: δ 1.82 (d, J = 6.40 Hz, 3H), 5.68 (q, J = 19.60 Hz, 1H), 7.17 (d, J = 2.40 Hz, 1H), 7.33 (dd, J = 2.00, 4.00 Hz, 2H), 7.36 (d, J = 2.80 Hz, 1H), 7.46 (dd, J = 8.80, 29.80 Hz, 1H), 7.70 (d, J = 2.40 Hz, 1H), 7.96 (s, 1H) |
| 175 isomer B | 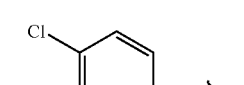 | 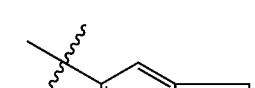 | Me | 1.935 | 390 | 400 MHz, MeOD: δ 1.82 (d, J = 6.40 Hz, 3H), 5.68 (q, J = 20.00 Hz, 1H), 7.18 (dd, J = 2.40, 8.80 Hz, 1H), 7.32-7.36 (m, 2H), 7.42 (d, J = 9.20 Hz, 1H), 7.49 (d, J = 9.20 Hz, 1H), 7.70 (d, J = 2.80 Hz, 1H), 7.96 (s, 1H) |
| 176 Isomer A |  |  | Me | 1.814 | 422 | 400 MHz, MeOD: δ 1.82 (d, J = 6.80 Hz, 3H), 5.67 (q, J = 19.60 Hz, 1H), 6.74 (t, J = 148.00 Hz, 1H), 7.18 (q, J = 11.60 Hz, 1H), 7.23 (d, J = 9.20 Hz, 1H), 7.33 (d, J = 2.00 Hz, 1H), 7.38 (dd, J = 11.60, Hz, 1H), 7.49 (d, J = 8.80 Hz, 1H), 7.67 (d, J = 2.80 Hz, 1H), 7.95 (s, 1H) |

| Ex. | R1 | R2 | X | LCMS RT (min) | LCMS Ion [M + H]⁺ | 1H NMR |
| --- | --- | --- | --- | --- | --- | --- |
| 177 Isomer B | B 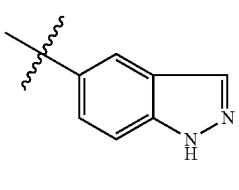 [SMILES: *c1ccc2[nH]ncc2c1] | 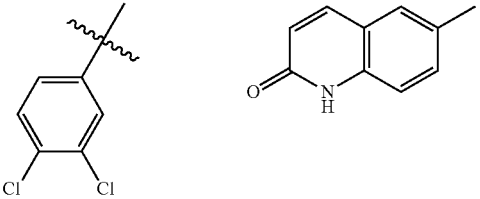 | Me | 1.813 | 422 | 400 MHz, MeOD: δ 1.82 (d, J = 6.40 Hz, 3H), 5.67 (q, J = 20.00 Hz, 1H), 6.74 (t, J = 148.00 Hz, 1H), 7.17-7.24 (m, 2H), 7.33 (d, J = 2.40 Hz, 1H), 7.37 (dd, J = 2.80, 9.00 Hz, 1H), 7.49 (d, J = 9.20 Hz, 1H), 7.66 (d, J = 2.80 Hz, 1H), 7.95 (s, 1H) |
| 178 | 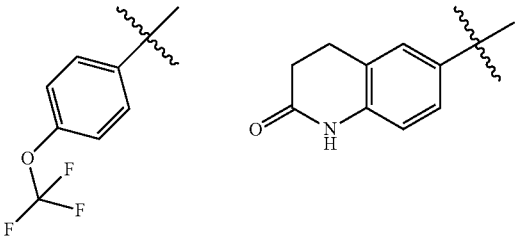 | | H | 1.94 | 403 | 1HNMR: 400 MHz, DMSO-d6: δ 5.52 (s, 2H), 6.51 (dd, J = 2.00, 9.60 Hz, 1H), 7.29 (d, J = 1.60 Hz, 2H), 7.37-7.42 (m, 2H), 7.59 (d, J = 8.80 Hz, 1H), 7.70 (d, J = 2.40 Hz, 1H), 7.83 (d, J = 9.60 Hz, 1H), 10.39 (s, 1H), 11.68 (s, 1H) |
| 179 | | | H | 1.933 | 421 | 1HNMR: 400 MHz, DMSO-d6: δ 2.42 (q, J = 7.20 Hz, 2H), 2.85 (t, J = 7.60 Hz, 2H), 5.40 (s, 2H), 6.79 (d, J = 8.80 Hz, 1H), 6.86 (dd, J = 2.80, 8.80 Hz, 1H), 6.94 (d, J = 2.80 Hz, 1H), 7.36 (d, J = 8.40 Hz, 2H), 7.52-7.55 (m, 2H), 9.97 (s, 1H), 10.24 (s, 1H) |

-continued

| Ex. | R1 | R2 | X | LCMS RT (min) | LCMS Ion [M + H]+ | 1H NMR |
|---|---|---|---|---|---|---|
| 180 | 4-(trifluoromethyl)phenyl | 3,4-dihydro-2-oxo-quinolin-6-yl | H | 1.941 | 403 [M − H]− | 1HNMR: 400 MHz, DMSO-d6: δ 2.41 (q, J = 7.20 Hz, 2H), 2.85 (t, J = 8.00 Hz, 2H), 5.42 (s, 2H), 6.79 (d, J = 8.80 Hz, 1H), 6.85 (d, J = 2.80 Hz, 1H), 6.94 (d, J = 2.80 Hz, 1H), 7.63 (d, J = 8.80 Hz, 2H), 7.70 (d, J = 8.80 Hz, 2H), 9.95 (s, 1H), 10.48 (s, 1H) |
| 181 | 4-(trifluoromethyl)phenyl | 2-oxo-quinolin-6-yl | H | 2.004 | 401 [M − H]− | 1HNMR: 400 MHz, DMSO-d6: δ 5.52 (s, 2H), 6.51 (dd, J = 1.60, 9.60 Hz, 1H), 7.29 (s, 2H), 7.37 (s, 1H), 7.62 (d, J = 8.80 Hz, 2H), 7.70 (d, J = 8.80 Hz, 2H), 7.83 (d, J = 6.00 Hz, 1H), 10.48 (s, 1H), 11.68 (s, 1H) |
| 182 | 4-chlorophenyl | 3,4-dihydro-2-oxo-quinolin-6-yl | H | 1.998 | 369 [M − H]− | 1HNMR: 400 MHz, DMSO-d6: δ 2.42 (q, J = 7.20 Hz, 2H), 2.85 (t, J = 8.00 Hz, 2H), 5.39 (s, 2H), 6.52 (s, 1H), 6.80 (d, J = 8.80 Hz, 1H), 6.86 (dd, J = 2.40, 8.60 Hz, 1H), 6.93 (d, J = 2.40 Hz, 1H), 7.39 (dd, J = 2.40, 6.80 Hz, 2H), 7.46 (dd, J = 2.80, 6.00 Hz, 2H), 9.95 (s, 1H), 10.16 (s, 1H) |

-continued

| Ex. | R1 | R2 | X | LCMS RT (min) | LCMS Ion [M + H]+ | 1H NMR |
|---|---|---|---|---|---|---|
| 183 | 4-Cl-phenyl | 2-oxo-1,2-dihydroquinolin-6-yl | H | 1.929 | 369 | 1HNMR: 400 MHz, DMSO-d6: δ 5.50 (s, 2H), 7.29 (d, J = 1.60 Hz, 2H), 7.37-7.40 (m, 3H), 7.47 (dd, J = 2.40, 6.80 Hz, 2H), 7.83 (d, J = 9.60 Hz, 1H), 10.15 (s, 1H), 11.68 (s, 1H) |
| 184 | 3,4-diCl-phenyl | 4-hydroxyphenyl | H | 2.026 | 350 [M − H]− | 1HNMR: 400 MHz, DMSO-d6: 5.35 (s, 2H), 6.70 (dd, J = 0.00, 12.80 Hz, 2H), 6.88 (dd, J = 4.00, 12.80 Hz, 2H), 7.41 (dd, J = 2.40, 8.80 Hz, 1H), 7.59 (d, J = 8.80 Hz, 1H), 7.71 (d, J = 2.80 Hz, 1H), 9.06 (s, 1H), 10.37 (s, 1H) |
| 185 | 4-CF3-phenyl | 4-hydroxyphenyl | H | 1.977 | 350 [M − H]− | 1HNMR: 400 MHz, DMSO-d6: δ 5.35 (s, 2H), 6.71 (dd, J = 0.00, 6.80 Hz, 2H), 6.89 (dd, J = 2.40, 6.60 Hz, 2H), 7.63 (d, J = 8.80 Hz, 2H), 7.70 (d, J = 8.80 Hz, 2H), 9.06 (s, 1H), 10.47 (s, 1H) |
| 186 | 4-(OCHF2)-phenyl | 2-oxo-1,2,3,4-tetrahydroquinolin-6-yl | H | 1.873 | 401 [M − H]− | 400 MHz, DMSO-d6: δ 2.42 (q, J = 7.60 Hz, 2H), 2.85 (t, J = 8.00 Hz, 2H), 5.39 (s, 2H), 6.79-6.87 (m, 2H), 6.93-7.30 (m, 4H), 7.48 (dd, J = 2.40, 6.80 Hz, 2H), 9.95 (s, 1H), 10.06 (s, 1H) |

| Ex. | R1 | R2 | X | LCMS RT (min) | LCMS Ion [M + H]+ | 1H NMR |
|---|---|---|---|---|---|---|
| 187 | 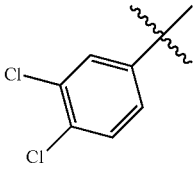 [SMILES: *c1ccc(Cl)c(Cl)c1] | 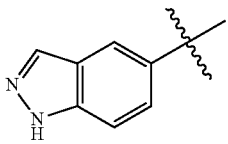 [SMILES: *c1ccc2[nH]ncc2c1] | H | 2.003 | 374 [M − H]− | 1HNMR: 400 MHz, DMSO-d6: δ 5.50 (s, 2H), 7.13 (dd, J = 0.00, 9.00 Hz, 1H), 7.35 (d, J = 2.40 Hz, 1H), 7.41 (dd, J = 2.40, 9.00 Hz, 1H), 7.50 (d, J = 9.20 Hz, 1H), 7.59 (d, J = 8.80 Hz, 1H), 7.70 (d, J = 2.40 Hz, 1H), 7.98 (s, 1H), 10.39 (s, 1H), 13.00 (s, 1H) |
| 188 | 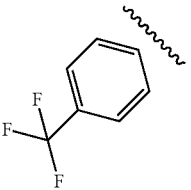 | 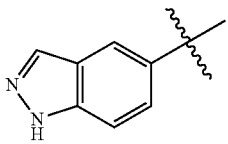 [SMILES: *c1ccc2[nH]ncc2c1] | H | 1.977 | 374 [M − H]− | 400 MHz, DMSO-d6: δ 5.51 (s, 2H), 7.14 (dd, J = 0.00, 9.20 Hz, 1H), 7.35 (d, J = 2.40 Hz, 1H), 7.51 (d, J = 9.20 Hz, 1H), 7.63 (d, J = 8.80 Hz, 2H), 7.70 (d, J = 8.80 Hz, 2H), 7.98 (s, 1H), 10.48 (s, 1H), 12.99 (s, 1H) |
| 189 | 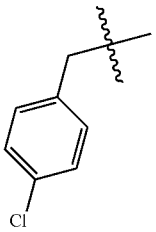 [SMILES: *Cc1ccc(Cl)cc1] | 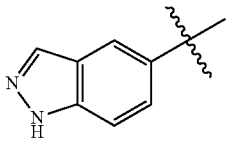 [SMILES: *c1ccc2[nH]ncc2c1] | H | 1.684 | 354 [M − H]− | 400 MHz, DMSO-d6: δ 4.27 (d, J = 6.40 Hz, 2H), 5.33 (s, 1H), 7.08-7.10 (m, 1H), 7.29 (d, J = 2.00 Hz, 1H), 7.32-7.39 (m, 4H), 7.49 (d, J = 8.80 Hz, 1H), 7.55-7.59 (m, 1H), 7.98 (s, 1H), 12.99 (s, 1H) |
| 190 | 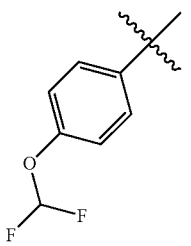 [SMILES: *c1ccc(OC(F)F)cc1] | 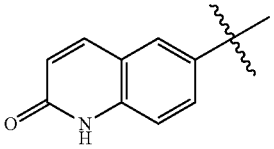 [SMILES: *c1ccc2[nH]c(=O)ccc2c1] | H | 1.898 | 399 [M − H]− | 400 MHz, DMSO-d6: δ 5.49 (s, 2H), 6.50-6.53 (m, 1H), 6.93-7.30 (m, 5H), 7.37 (s, 1H), 7.46-7.49 (m, 2H), 7.84 (d, J = 9.60 Hz, 1H), 10.06 (s, 1H), 11.68 (s, 1H) |

-continued

| Ex. | R1 | R2 | X | LCMS RT (min) | LCMS Ion [M + H]+ | 1H NMR |
|---|---|---|---|---|---|---|
| 191 | (4-(difluoromethoxy)-3-chlorophenyl group) | (2-oxo-1,2-dihydroquinolin-6-yl group) | H | 1.919 | 433 [M − H]− | 400 MHz, DMSO-d6: δ 5.51 (s, 2H), 6.52 (d, J = 9.60 Hz, 1H), 6.68-7.38 (m, 3H), 7.41-7.44 (m, 3H), 7.65 (d, J = 2.80 Hz, 1H), 7.84 (d, J = 9.60 Hz, 1H), 10.32 (s, 1H), 11.70 (s, 1H) |
| 192 | (3-chloro-4-fluorophenyl group) | (2-oxo-1,2-dihydroquinolin-6-yl group) | H | 1.905 | 387.0 | 400 MHz, DMSO-d6: δ 5.51 (s, 2H), 6.50-6.51 (m, 1H), 7.29 (d, J = 1.60 Hz, 2H), 7.37-7.39 (m, 3H), 7.62-7.64 (m, 1H), 7.83 (d, J = 9.60 Hz, 1H), 10.24 (s, 1H), 11.68 (s, 1H) |
| 193 | (3-chlorophenyl group) | (2-oxo-1,2-dihydroquinolin-6-yl group) | H | 1.879 | 396.06 | 400 MHz, DMSO-d6: δ 5.51 (s, 2H), 6.50-6.51 (m, 1H), 7.01-7.01 (m, 1H), 7.29-7.33 (m, 5H), 7.54 (d, J = 1.60 Hz, 1H), 7.84 (d, J = 9.60 Hz, 1H), 10.27 (s, 1H), 11.70 (s, 1H) |

Example 194

6-(2-(3-(3,4-dichlorophenylamino)-1,2,4-oxadiazol-5-yl)ethyl)-3,4-dihydroquinolin-2(1H)-one 3-(1-(4-methoxybenzyl)-2-oxo-1,2,3,4-tetrahydroquinolin-6-yl)propanoic acid

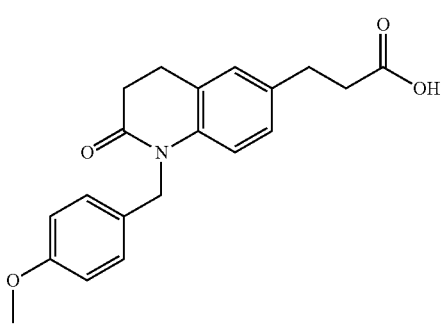 [SMILES: COc1ccc(CN2C(=O)CCc3cc(CCC(=O)O)ccc32)cc1]

To a stirred solution of ethyl 3-(1-(4-methoxybenzyl)-2-oxo-1,2,3,4-tetrahydroquinolin-6-yl)propanoate (0.76 g, 2.07 mmol) in 1:1 THF/methanol (20 mL) was added a solution of LiOH (0.26 g, 6.21 mmol) in water (5 mL). The reaction mixture was stirred at room temperature for 3 h. Solvents were concentrated and the reaction mixture was acidified with citric acid solution to pH 6. Solid was filtered and dried to afford 3-(1-(4-methoxybenzyl)-2-oxo-1,2,3,4-tetrahydroquinolin-6-yl)propanoic acid as a pale brown solid (0.6 g, 86%). $^1$HNMR 400 MHz, DMSO-d6: δ 2.46-2.51 (m, 2H), 2.65-2.87 (m, 4H), 2.89 (t, J=16.00 Hz, 2H), 3.71 (s, 3H), 5.05 (s, 2H), 6.85-6.87 (m, 3H), 6.96-6.99 (m, 1H), 7.08 (s, 1H), 7.14-7.16 (m, 2H), 12.08 (s, 1H). LCMS: RT 2.023 min; LCMS (ES-API), RT; 0.81 min; m/z 340.0 [M−H]−.

6-(2-(3-(3,4-dichlorophenylamino)-1,2,4-oxadiazol-5-yl)ethyl)-1-(4-methoxybenzyl)-3,4-dihydroquinolin-2(1H)-one

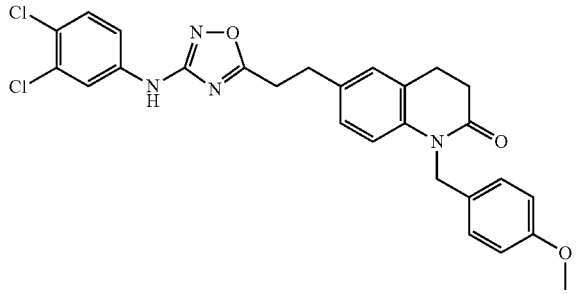 [SMILES: COc1ccc(CN2C(=O)CCc3cc(CCc4nc(Nc5ccc(Cl)c(Cl)c5)no4)ccc32)cc1]

To a solution of 3-(1-(4-methoxybenzyl)-2-oxo-1,2,3,4-tetrahydroquinolin-6-yl)propanoic acid (200 mg, 0.589 mmol) in DMF (3 mL) were added HOBT (99 mg, 0.648 mmol), EDC (124 mg, 0.648 mmol), and DIPEA (0.154 mL, 0.884 mmol). The reaction mixture was stirred for 30 minutes, then (E)-1-(3,4-dichlorophenyl)-2-hydroxyguanidine (130 mg, 0.589 mmol) was added followed by sodium sulfate (419 mg, 2.95 mmol). The reaction mixture was heated at 110° C. for 12 h, then concentrated, diluted with water, and extracted with ethyl acetate. The organic layer was dried over sodium sulfate and concentrated. The crude product was purified by flash chromatography on silica gel using 10-100% EtOAc/hexane to give 6-(2-(3-((3,4-dichlorophenyl)amino)-1,2,4-oxadiazol-5-yl)ethyl)-1-(4-methoxybenzyl)-3,4-dihydroquinolin-2(1H)-one as a yellow solid (0.06 g, 11% yield). 1H NMR 400 MHz, DMSO-d6: δ 2.65-2.68 (m, 2H), 2.90 (t, J=15.20 Hz, 2H), 2.95 (t, J=12.40 Hz, 2H), 3.16 (t, J=15.20 Hz, 2H), 3.70 (s, 3H), 5.05 (s, 2H), 6.84-6.90 (m, 3H), 7.02-7.04 (m, 1H), 7.14-7.16 (m, 3H), 7.38-7.41 (m, 1H), 7.57 (d, J=8.80 Hz, 1H), 7.69 (s, 1H), 10.23 (s, 1H). LCMS (ES-API), RT: 2.20 min; m/z 523.0 [M−H]−.

6-(2-(3-(3,4-dichlorophenylamino)-1,2,4-oxadiazol-5-yl)ethyl)-3,4-dihydroquinolin-2(1H)-one

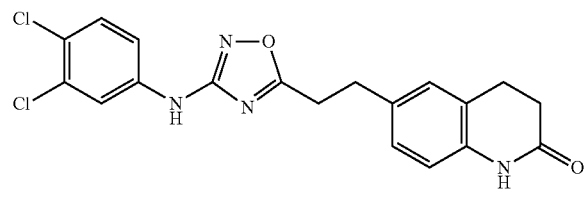 [SMILES: O=C1CCc2cc(CCc3nc(Nc4ccc(Cl)c(Cl)c4)no3)ccc2N1]

To 6-(2-(3-(3,4-dichlorophenylamino)-1,2,4-oxadiazol-5-yl)ethyl)-1-(4-methoxybenzyl)-3,4-dihydroquinolin-2(1H)-one (0.06 g 0.011 mmol) was added TFA (0.13 g, 0.11 mmol) and anisole (0.012 mmol). The resulting reaction mixture was heated to 60° C. for 4 h. TFA and anisole were removed under vacuum and the crude material was washed with hexane and diethyl ether to afford 6-(2-(3-(3,4-dichlorophenylamino)-1,2,4-oxadiazol-5-yl)ethyl)-3,4-dihydroquinolin-2(1H)-one as a brown solid (19.2 mg, 41%). 1HNMR: 400 MHz, DMSO-d6: δ 2.45 (q, J=7.20 Hz, 2H), 2.84 (t, J=7.60 Hz, 2H), 2.99 (t, J=7.60 Hz, 2H), 3.17 (t, J=7.60 Hz, 2H), 6.77 (d, J=7.60 Hz, 1H), 7.03 (t, J=1.20 Hz, 1H), 7.10 (s, 1H), 7.40 (dd, J=2.40, 8.80 Hz, 1H), 7.57 (d, J=8.80 Hz, 1H), 7.70 (d, J=2.40 Hz, 1H), 10.00 (s, 1H), 10.23 (s, 1H). LCMS: RT 2.023 min; LCMS (ES-API), m/z 401.0 [M−H]−.

The following compounds were synthesized by methods similar to that described for 6-(2-(3-(3,4-dichlorophenylamino)-1,2,4-oxadiazol-5-yl)ethyl)-3,4-dihydroquinolin-2(1H)-one.

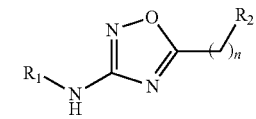

| Ex | R1 | R2 | n | LCMS RT (min) | LCMS Ion [M + H]+ | 1H NMR |
|---|---|---|---|---|---|---|
| 195 | ![F3CO-phenyl] | 5-(3-CF3)-1H-indazolyl | 2 | 2.132 | 458.0 | 400 MHz, MeOD: δ 3.23-3.31 (m, 4H), 7.21 (dd, J = 0.40, 9.00 Hz, 2H), 7.45 (dd, J = 1.20, 8.60 Hz, 1H), 7.50-7.52 (m, 2H), 7.60 (dd, J = 0.40, 8.60 Hz, 1H), 7.69 (s, 1H) |
| 196 | 3,4-dichlorophenyl | 5-(3-CF3)-1H-indazolyl | 2 | 2.149 | 442.7 | 400 MHz, DMSO-d6: δ 2.42-2.50 (m, 4H), 6.53 (dd, J = 2.80, 8.80 Hz, 1H), 6.59-6.64 (m, 2H), 6.79 (d, J = 8.40 Hz, 1H), 6.87-6.90 (m, 2H) |
| 197 | 4-(CHF2O)-3-Cl-phenyl | 5-(3-CF3)-1H-indazolyl | 2 | 2.064 | 474.0 | 400 MHz, MeOD: δ 3.22-3.31 (m, 4H), 6.75 (t, J = 147.60 Hz, 1H), 7.23 (d, J = 9.20 Hz, 1H), 7.37 (dd, J = 2.40, 9.00 Hz, 1H), 7.45 (dd, J = 1.60, 8.60 Hz, 1H), 7.60 (dd, J = 0.40, 8.80 Hz, 1H), 7.67 (t, J = 7.20 Hz, 2H) |

-continued

| Ex | R1 | R2 | n | LCMS RT (min) | LCMS Ion [M + H]⁺ | 1H NMR |
|---|---|---|---|---|---|---|
| 198 | 3,4-dichlorophenyl | 5-(1H-indazolyl) | 2 | 2.03 | 372 [M − H]⁻ | 400 MHz, DMSO-d6: δ 3.19 (t, J = 6.80 Hz, 2H), 3.25 (t, J = 6.80 Hz, 2H), 7.28 (d, J = 8.80 Hz, 1H), 7.39 (d, J = 8.00 Hz, 1H), 7.48 (d, J = 8.40 Hz, 1H), 7.55 (s, 1H), 7.62 (s, 1H), 7.69 (s, 1H), 7.99 (s, 1H), 10.22 (s, 1H), 12.99 (s, 1H) |
| 199 | 3,4-dichlorophenyl | 6-(3,4-dihydroquinolin-2(1H)-one) | 2 | 2.023 | 401 [M − H]⁻ | 400 MHz, DMSO-d6: δ 2.45 (q, J = 7.20 Hz, 2H), 2.84 (t, J = 7.60 Hz, 2H), 2.99 (t, J = 7.60 Hz, 2H), 3.17 (t, J = 7.60 Hz, 2H), 6.77 (d, J = 7.60 Hz, 1H), 7.03 (t, J = 1.20 Hz, 1H), 7.10 (s, 1H), 7.40 (dd, J = 2.40, 8.80 Hz, 1H), 7.57 (d, J = 8.80 Hz, 1H), 7.70 (d, J = 2.40 Hz, 1H), 10.00 (s, 1H), 10.23 (s, 1H) |
| 200 | 4-chlorobenzyl | 4-hydroxyphenyl | 2 | 1.70 | 330 | 400 MHz, DMSO-d6: δ 2.88 (t, J = 14.80 Hz, 2H), 2.98 (t, J = 16.00 Hz, 2H), 4.25 (d, J = 6.40 Hz, 2H), 6.65-6.67 (m, 2H), 7.01 (d, J = 12.00 Hz, 2H), 7.31-7.40 (m, 5H), 9.20 (s, 1H) |
| 201 | 4-(difluoromethoxy)phenyl | 5-(1H-indazolyl) | 2 | 1.833 | 372 | 400 MHz, DMSO-d6: δ 3.18-3.23 (m, 4H), 6.92-7.16 (m, 3H), 7.28-7.29 (m, 1H), 7.45-7.49 (m, 3H), 7.62 (s, 1H), 8.00 (s, 1H), 9.91 (s, 1H), 12.99 (s, 1H) |
| 202 | 3,4-dichlorophenyl | 5-(1H-indazolyl) | 3 | 2.06 | 386 [M − H]⁻ | 400 MHz, DMSO-d6: δ 2.05-2.13 (m, 2H), 2.80 (t, J = 15.20 Hz, 2H), 2.88 (t, J = 14.80 Hz, 2H), 7.23-7.26 (m, 1H), 7.40-7.43 (m, 1H), 7.48 (d, J = 8.40 Hz, 1H), 7.58 (d, J = 8.80 Hz, 2H), 7.72 (d, J = 2.80 Hz, 1H), 8.00 (s, 1H), 10.26 (s, 1H), 12.97 (s, 1H) |

| Ex | R1 | R2 | n | LCMS RT (min) | LCMS Ion [M + H]+ | 1H NMR |
|---|---|---|---|---|---|---|
| 203 | 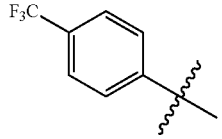 | 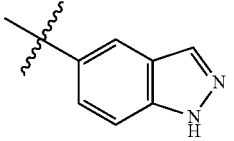 [SMILES: *c1ccc2[nH]ncc2c1] | 3 | 2.08 | 386 [M − H]− | 400 MHz, DMSO-d6: δ 2.09-2.12 (m, 2H), 2.81 (t, J = 14.80 Hz, 2H), 2.89 (t, J = 14.80 Hz, 2H), 7.24-7.26 (m, 1H), 7.48 (d, J = 8.40 Hz, 1H), 7.58 (s, 1H), 7.63-7.70 (m, 4H), 8.00 (s, 1H), 10.33 (s, 1H), 12.95 (s, 1H) |
| 204 | 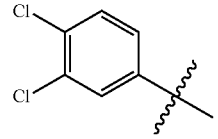 [SMILES: *c1ccc(Cl)c(Cl)c1] | 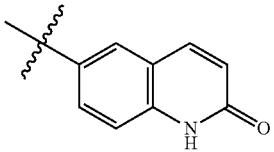 [SMILES: *c1ccc2[nH]c(=O)ccc2c1] | 2 | 1.84 | 401 | 400 MHz, DMSO-d6: δ 3.12 (t, J = 14.80 Hz, 2H), 3.25 (t, J = 17.20 Hz, 2H), 6.48 (d, J = 9.20 Hz, 1H), 7.24 (d, J = 8.40 Hz, 1H), 7.38-7.45 (m, 2H), 7.56-7.58 (m, 2H), 7.70 (d, J = 2.80 Hz, 1H), 7.84 (d, J = 12.00 Hz, 1H), 10.22 (s, 1H), 11.69 (s, 1H) |
| 205 | 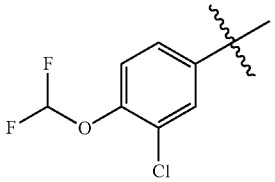 | 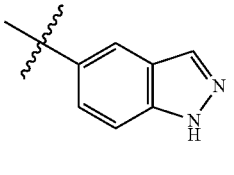 [SMILES: *c1ccc2[nH]ncc2c1] | 2 | 1.99 | 404 [M − H]− | 400 MHz, DMSO-d6: δ 3.18 (t, J = 13.60 Hz, 2H), 3.25 (t, J = 16.40 Hz, 2H), 6.96-7.49 (m, 5H), 7.62-7.64 (m, 2H), 8.00 (s, 1H), 10.15 (s, 1H), 13.03 (s, 1H) |
| 206 | 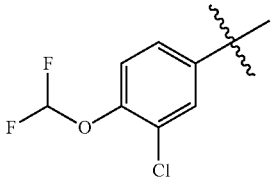 [SMILES: *c1ccc(OC(F)F)c(Cl)c1] | 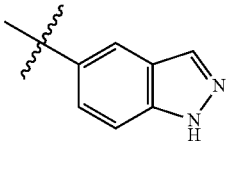 [SMILES: *c1ccc2[nH]ncc2c1] | 3 | 2.04 | 420 | 400 MHz, DMSO-d6: δ 2.08-2.11 (m, 2H), 2.80 (t, J = 15.20 Hz, 2H), 2.88 (t, J = 14.80 Hz, 2H), 6.97-7.36 (m, 3H), 7.42-7.49 (m, 2H), 7.57 (s, 1H), 7.67 (d, J = 2.40 Hz, 1H), 8.00 (s, 1H), 10.14 (s, 1H), 12.95 (s, 1H) |
| 207 | 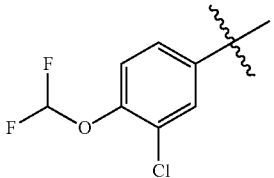 [SMILES: *c1ccc(OC(F)F)c(Cl)c1] | 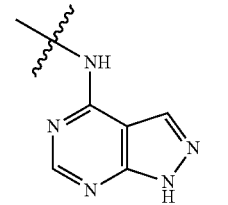 [SMILES: *Nc1ncnc2[nH]ncc12] | 2 | 1.87 | 423 | 400 MHz, DMSO-d6: δ 3.25 (t, J = 13.60 Hz, 2H), 3.49 (s, 1H), 3.92-3.93 (m, 2H), 6.96-7.36 (m, 1H), 7.40-7.43 (m, 2H), 7.65 (d, J = 2.80 Hz, 1H), 8.08 (s, 1H), 8.25 (s, 1H), 8.41 (s, 1H), 10.15 (s, 1H), 13.43 (s, 1H) |
| 208 | 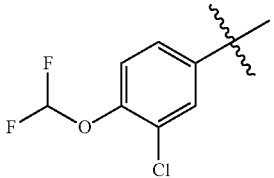 | 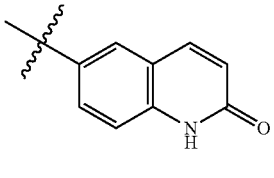 | 2 | 1.93 | 431 [M − H]− | 400 MHz, DMSO-d6: δ 3.13 (t, J = 7.60 Hz, 2H), 3.23 (t, J = 7.60 Hz, 2H), 6.48 (d, J = 10.40 Hz, 1H), 6.96-7.45 (m, 5H), 7.56 (s, 1H), 7.64 (d, J = 2.40 Hz, 1H), 7.84 (d, J = 9.60 Hz, 1H), 10.13 (s, 1H), 11.69 (s, 1H), |

| Ex | R1 | R2 | n | LCMS RT (min) | LCMS Ion [M + H]+ | 1H NMR |
|---|---|---|---|---|---|---|
| 209 | 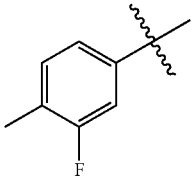 [SMILES: *c1ccc(C)c(F)c1] | 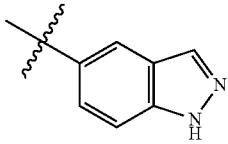 [SMILES: *c1ccc2[nH]ncc2c1] | 2 | 2.27 | 336 [M − H]− | 400 MHz, DMSO-d6: δ 2.16 (s, 3H), 3.17-3.24 (m, 4H), 7.11-7.30 (m, 4H), 7.48 (d, J = 8.80 Hz, 1H), 7.62 (s, 1H), 8.00 (s, 1H), 9.93 (s, 1H), 12.98 (s, 1H) |
| 210 | 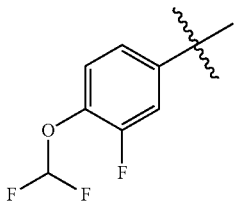 | 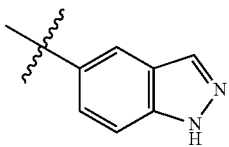 [SMILES: *c1ccc2[nH]ncc2c1] | 2 | 2.10 | 388 [M − H]− | 400 MHz, DMSO-d6: δ 3.19 (t, J = 6.80 Hz, 2H), 3.24 (t, J = 6.80 Hz, 2H), 6.94-7.30 (m, 4H), 7.31-7.49 (m, 2H), 7.62 (s, 1H), 8.00 (s, 1H), 10.15 (s, 1H), 13.00 (s, 1H) |
| 211 | 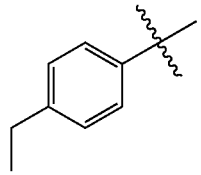 [SMILES: *c1ccc(CC)cc1] | 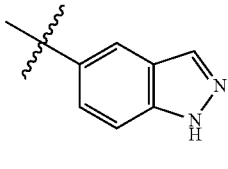 [SMILES: *c1ccc2[nH]ncc2c1] | 2 | 1.92 | 334 | 400 MHz, DMSO-d6: δ 1.16 (t, J = 14.80 Hz, 3H), 2.53 (q, J = 14.00 Hz, 2H), 3.17-3.21 (m, 4H), 7.13 (d, J = 8.80 Hz, 2H), 7.27-7.36 (m, 3H), 7.47 (d, J = 8.40 Hz, 1H), 7.62 (s, 1H), 7.99 (s, 1H), 9.66 (s, 1H), 12.97 (s, 1H) |
| 212 | 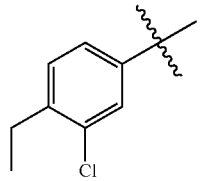 [SMILES: *c1ccc(CC)c(Cl)c1] | 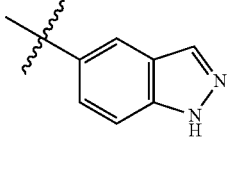 [SMILES: *c1ccc2[nH]ncc2c1] | 2 | 2.01 | 368 | 400 MHz, DMSO-d6: δ 1.15 (t, J = 15.20 Hz, 3H), 2.63 (q, J = 20.40 Hz, 2H), 3.16-3.23 (m, 4H), 7.26-7.33 (m, 3H), 7.48 (d, J = 8.80 Hz, 1H), 7.52 (s, 1H), 7.62 (s, 1H), 8.00 (s, 1H), 9.94 (s, 1H), 12.98 (s, 1H) |
| 213 | 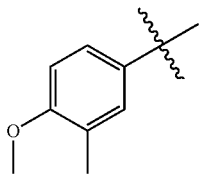 [SMILES: *c1ccc(OC)c(C)c1] | 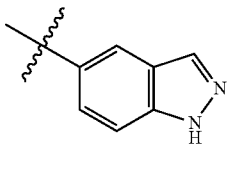 [SMILES: *c1ccc2[nH]ncc2c1] | 2 | 1.87 | 350 | 400 MHz, DMSO-d6: δ 2.13 (s, 3H), 3.17-3.20 (m, 4H), 3.74 (s, 3H), 6.87 (d, J = 8.80 Hz, 1H), 7.19 (d, J = 2.40 Hz, 1H), 7.23-7.29 (m, 2H), 7.47 (d, J = 8.40 Hz, 1H), 7.62 (s, 1H), 8.00 (s, 1H), 9.46 (s, 1H), 12.98 (s, 1H) |
| 214 | 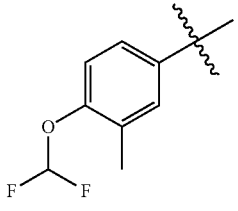 [SMILES: *c1ccc(OC(F)F)c(C)c1] | 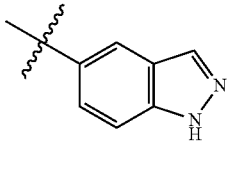 [SMILES: *c1ccc2[nH]ncc2c1] | 2 | 1.985 | 386 | 400 MHz, DMSO-d6: δ 2.21 (s, 3H), 3.18-3.23 (m, 4H), 6.86-7.33 (m, 5H), 7.48 (d, J = 8.40 Hz, 1H), 7.62 (s, 1H), 8.00 (s, 1H), 9.81 (s, 1H), 13.00 (s, 1H) |

| Ex | R1 | R2 | n | LCMS RT (min) | LCMS Ion [M + H]⁺ | 1H NMR |
|---|---|---|---|---|---|---|
| 215 | 4-ethyl-2-fluorophenyl | 1H-indazol-5-yl | 2 | 2.02 | 352 | 400 MHz, DMSO-d6: δ 1.15 (t, J = 15.20 Hz, 3H), 2.54 (q, J = 16.00 Hz, 2H), 3.18-3.23 (m, 4H), 7.14-7.30 (m, 4H), 7.47 (d, J = 8.40 Hz, 1H), 7.62 (s, 1H), 8.00 (s, 1H), 9.94 (s, 1H), 12.98 (s, 1H) |
| 216 | 3-(difluoromethyl)-4-fluorophenyl | 1H-indazol-5-yl | 2 | 1.963 | 374 | 400 MHz, DMSO-d6: δ 3.17-3.26 (m, 4H), 7.08-7.36 (m, 3H), 7.48 (d, J = 8.80 Hz, 1H), 7.58-7.62 (m, 2H), 7.70-7.71 (m, 1H), 8.00 (s, 1H), 10.11 (s, 1H), 13.05 (s, 1H) |
| 217 | 3-fluoro-4-methylphenyl | 4,4-dimethyl-2-oxo-1,2,3,4-tetrahydroquinolin-6-yl | 2 | 1.963 | 395 [M − H]⁻ | 400 MHz, DMSO-d6: δ 1.56 (s, 6H), 2.17 (s, 3H), 3.03 (t, J = 7.20 Hz, 2H), 3.15 (t, J = 7.60 Hz, 2H), 6.81 (d, J = 8.00 Hz, 1H), 7.15-7.27 (m, 5H), 9.94 (s, 1H), 10.12 (s, 1H) |
| 218 | 4-(difluoromethoxy)-3-fluorophenyl | 4,4-dimethyl-2-oxo-1,2,3,4-tetrahydroquinolin-6-yl | 2 | 2.248 | 449 | 400 MHz, DMSO-d6: δ 1.56 (s, 6H), 3.02 (t, J = 14.80 Hz, 2H), 3.18 (t, J = 15.20 Hz, 2H), 6.80 (d, J = 8.40 Hz, 1H), 7.12-7.36 (m, 6H), 7.42-7.46 (m, 1H), 10.12 (s, 1H), 10.15 (s, 1H) |
| 219 | 4-(difluoromethoxy)-3-fluorophenyl | 4-hydroxyphenyl | 2 | 2.215 | 366 | 400 MHz, DMSO-d6: δ 3.03-3.12 (m, 4H), 6.55-6.92 (m, 3H), 7.06-7.08 (m, 2H), 7.20-7.22 (m, 2H), 7.45-7.48 (m, 1H) |
| 220 | 4-(difluoromethoxy)-3-fluorophenyl | 2-oxo-2,3-dihydrobenzo[d]oxazol-6-yl | 2 | 2.04 | 452 | 400 MHz, DMSO-d6: δ 3.09 (t, J = 15.20 Hz, 2H), 3.21 (t, J = 15.20 Hz, 2H), 6.94-7.36 (m, 6H), 7.42-7.46 (m, 1H), 10.15 (s, 1H), 11.54 (s, 1H) |

| Ex | R1 | R2 | n | LCMS RT (min) | LCMS Ion [M + H]+ | 1H NMR |
|---|---|---|---|---|---|---|
| 221 | 3-chloro-4-(difluoromethoxy)phenyl | pyrimidin-2-ylamino | 2 | 1.840 | 351 | 400 MHz, DMSO-d6: δ 3.14 (t, J = 13.60 Hz, 2H), 3.67-3.72 (m, 2H), 6.61 (t, J = 9.20 Hz, 1H), 7.32 (t, J = 11.60 Hz, 1H), 7.40-7.42 (m, 1H), 7.57 (d, J = 8.80 Hz, 1H), 7.71 (d, J = 2.40 Hz, 1H), 8.29 (d, J = 4.40 Hz, 2H), 10.23 (s, 1H) |
| 222 | 3,4-dichlorophenyl | pyrimidin-2-ylamino | 2 | 1.759 | 383 | 400 MHz, DMSO-d6: δ 3.14 (t, J = 13.60 Hz, 2H), 3.69 (q, J = 19.20 Hz, 2H), 6.61 (t, J = 9.60 Hz, 1H), 6.97-7.44 (m, 4H), 7.65 (d, J = 2.80 Hz, 1H), 8.31 (t, J = 16.80 Hz, 2H), 10.16 (s, 1H) |
| 223 | 4-(trifluoromethyl)phenyl | 4-hydroxyphenyl | 2 | 2.012 | 348 [M − H]− | 1HNMR: 400 MHz, DMSO-d6: δ 2.97 (t, J = 7.60 Hz, 2H), 3.12 (t, J = 0.00 Hz, 2H), 6.67 (dd, J = 2.00, 6.40 Hz, 2H), 7.05 (d, J = 8.80 Hz, 2H), 7.61 (d, J = 8.80 Hz, 2H), 7.68 (d, J = 8.80 Hz, 2H), 9.21 (s, 1H), 10.31 (s, 1H) |
| 224 | 4-(trifluoromethoxy)phenyl | 4-hydroxyphenyl | 2 | 2.043 | 364 [M − H]− | 1HNMR: 400 MHz, DMSO-d6: δ 2.96 (t, J = 7.20 Hz, 2H), 3.12 (t, J = 0.00 Hz, 2H), 6.67 (d, J = 8.40 Hz, 2H), 7.05 (d, J = 8.40 Hz, 2H), 7.33 (d, J = 8.80 Hz, 2H), 7.52 (dd, J = 2.00, 7.00 Hz, 2H), 9.20 (s, 1H), 10.04 (s, 1H) |
| 225 | 4-chlorophenyl | 4-hydroxyphenyl | 2 | 1.965 | 314 [M − H]− | 1HNMR: 400 MHz, DMSO-d6: δ 2.96 (d, J = 7.60 Hz, 2H), 3.11 (t, J = 0.00 Hz, 2H), 6.67 (dd, J = 2.00, 6.60 Hz, 2H), 7.05 (d, J = 8.40 Hz, 2H), 7.36 (dd, J = 2.00, 6.80 Hz, 2H), 7.45 (dd, J = 2.00, 7.00 Hz, 2H), 9.20 (s, 1H), 9.98 (s, 1H) |
| 226 | 4-(difluoromethoxy)phenyl | 4-hydroxyphenyl | 2 | 1.940 | 346 [M − H]− | 400 MHz, DMSO-d6: δ 2.96 (t, J = 7.60 Hz, 2H), 3.11 (t, J = 0.00 Hz, 2H), 6.68 (dd, J = 2.00, 6.40 Hz, 2H), 6.92-7.29 (m, 5H), 7.47 (dd, J = 2.00, 6.80 Hz, 2H), 9.20 (s, 1H), 9.88 (s, 1H) |

| Ex | R1 | R2 | n | LCMS RT (min) | LCMS Ion [M + H]+ | 1H NMR |
|---|---|---|---|---|---|---|
| 227 | 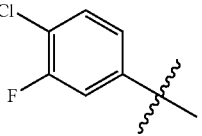 | 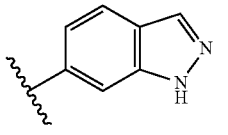 [SMILES: *c1ccc2cn[nH]c2c1] | 2 | 2.02 | 358.7 | 400 MHz, DMSO-d6: δ 3.22-3.23 (m, 4H), 7.04 (d, J = 1.20 Hz, 1H), 7.06-7.06 (m, 1H), 7.39 (s, 1H), 7.44-7.45 (m, 2H), 7.69 (d, J = 8.00 Hz, 1H), 8.01 (s, 1H), 10.26 (s, 1H), 12.95 (s, 1H) |
| 228 | 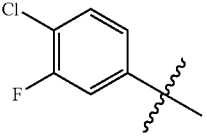 | 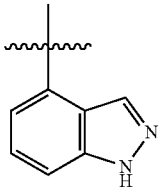 [SMILES: *c1cccc2[nH]ncc12] | 2 | 1.92 | 356.0 | 400 MHz, DMSO-d6: δ 3.28-3.28 (m, 2H), 3.49 (d, J = 7.60 Hz, 2H), 7.02 (s, 1H), 7.16-7.17 (m, 1H), 7.17-7.19 (m, 2H), 7.31-7.33 (m, 2H), 7.47 (s, 1H) |
| 229 | 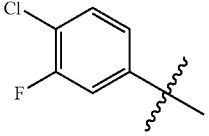 | 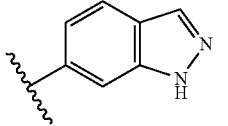 [SMILES: *c1ccc2cn[nH]c2c1] | 3 | 2.01 | 370 | 400 MHz, DMSO-d6: δ 2.08-2.10 (m, 2H), 2.82-2.84 (m, 2H), 2.88-2.90 (m, 2H), 7.00 (d, J = 1.20 Hz, 1H), 7.02-7.02 (m, 1H), 7.35 (s, 1H), 7.47-7.48 (m, 2H), 7.69 (d, J = 8.40 Hz, 1H), 8.00 (s, 1H), 10.27 (s, 1H), 12.93 (s, 1H) |
| 230 | 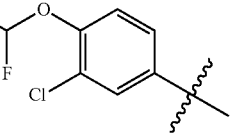 | 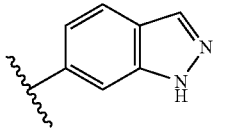 [SMILES: *c1ccc2cn[nH]c2c1] | 2 | 1.89 | 404.0 | 400 MHz, DMSO-d6: δ 3.21-3.23 (m, 4H), 6.96-7.04 (m, 5H), 7.64 (d, J = 2.40 Hz, 1H), 7.69 (d, J = 8.00 Hz, 1H), 8.01 (s, 1H), 10.16 (s, 1H), 12.97 (s, 1H) |
| 231 | 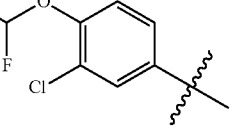 | 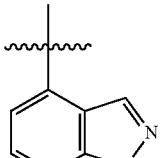 | 2 | 1.94 | 406 | 400 MHz, DMSO-d6: δ 3.31 (d, J = 7.60 Hz, 2H), 3.49 (d, J = 7.60 Hz, 2H), 6.56-6.75 (m, 1H), 7.02 (d, J = 7.20 Hz, 1H), 7.31-7.33 (m, 3H), 7.66 (d, J = 2.40 Hz, 1H), 8.17 (s, 1H), |
| 232 | 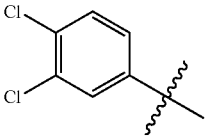 | 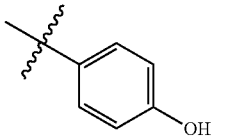 [SMILES: *c1ccc(O)cc1] | 2 | 2.034 | 348 [M − H]− | 400 MHz, DMSO-d6: δ 2.96 (t, J = 7.60 Hz, 2H), 3.14 (t, J = 7.60 Hz, 2H), 6.68 (dd, J = 1.60, 6.60 Hz, 2H), 7.05 (d, J = 8.80 Hz, 2H), 7.40 (dd, J = 2.40, 8.80 Hz, 1H), 7.57 (d, J = 8.80 Hz, 1H), 7.70 (d, J = 2.40 Hz, 1H), 9.21 (s, 1H), 10.23 (s, 1H) |
| 233 | 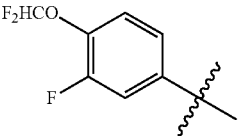 [SMILES: *c1ccc(OC(F)F)c(F)c1] | 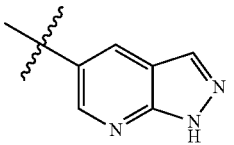 [SMILES: *c1cnc2[nH]ncc2c1] | 2 | 2.18 | 391.0 | 400 MHz, DMSO-d6) δ ppm: 300-3.28 (m, 4H) 6.87-7.49 (m, 5H) 8.04-8.21 (m, 2H) 8.48 (d, J = 2.01 Hz, 1H) 10.15 (s, 1H) 13.56 (br. s., 1H) |

-continued

| Ex | R1 | R2 | n | LCMS RT (min) | LCMS Ion [M + H]+ | 1H NMR |
|---|---|---|---|---|---|---|
| 234 | 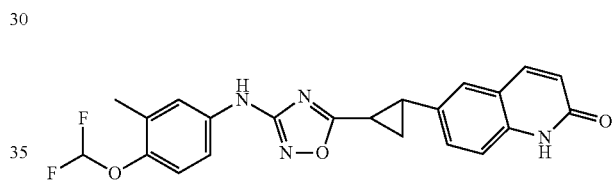 | | 2 | 2.15 | 438.0 | 400 MHz, DMSO-d6: δ 3.22-3.23 (m, 4H), 6.96 (s, 2H), 7.14 (s, 2H), 7.33-7.33 (m, 2H), 7.64 (s, 1H), 10.13 (s, 1H), 13.22 (s, 1H) |

Example 235

6-(2-(3-((4-(difluoromethoxy)-3-methylphenyl)amino)-1,2,4-oxadiazol-5-yl)cyclopropyl)quinolin-2(1H)-one (E)-6-(2-(3-((4-(difluoromethoxy)-3-methylphenyl)amino)-1,2,4-oxadiazol-5-yl)vinyl)quinolin-2(1H)-one

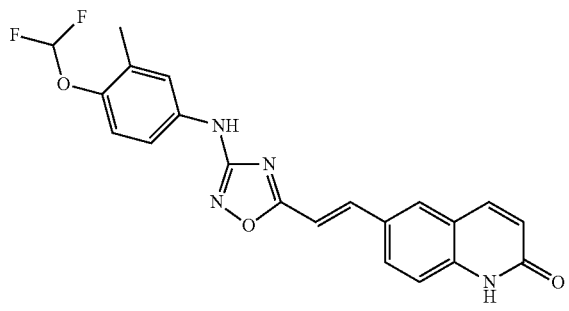 [SMILES: Cc1cc(Nc2noc(/C=C/c3ccc4[nH]c(=O)ccc4c3)n2)ccc1OC(F)F]

To a solution of (E)-3-(2-oxo-1-((2-(trimethylsilyl)ethoxy)methyl)-1,2-dihydroquinolin-6-yl)acrylic acid (80 mg, 0.232 mmol) and HATU (132 mg, 0.347 mmol) in DMF (2 ml) was added TEA (0.097 mL, 0.695 mmol). The reaction mixture was stirred for 30 minutes. A solution of (E)-1-(4-(difluoromethoxy)-2-methylphenyl)-2-hydroxyguanidine (80 mg, 0.347 mmol) in DMF was then added to and stirred at room temperature for 1 h. Sodium sulfate (99 mg, 0.695 mmol) was added and the reaction mixture was heated at 90° C. overnight. Water was added and the mixture was extracted with ethyl acetate (2×50 mL). The organic layer was dried over sodium sulfate and concentrated. The crude product was purified by flash chromatography on silica gel using 10-12% chloroform in ethyl acetate to obtain (E)-6-(2-(3-((4-(difluoromethoxy)-3-methylphenyl)amino)-1,2,4-oxadiazol-5-yl)vinyl)quinolin-2(1H)-one (65 mg, 52%). LCMS, RT 2.298 min; LCMS (ES-API), m/z 541.

6-(2-(3-((4-(difluoromethoxy)-3-methylphenyl)amino)-1,2,4-oxadiazol-5-yl)cyclopropyl)-1-((2-(trimethylsilyl)ethoxy)methyl)quinolin-2(1H)-one

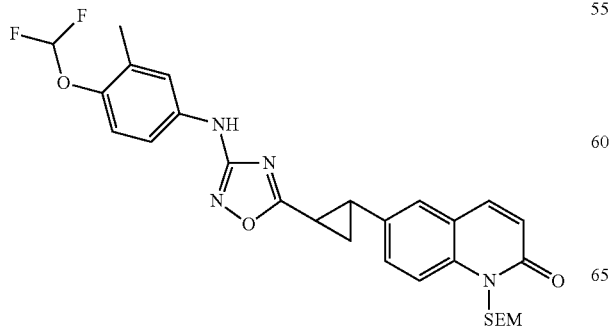

To a solution of (E)-6-(2-(3-((4-(difluoromethoxy)-3-methylphenyl)amino)-1,2,4-oxadiazol-5-yl)vinyl)-1-((2-(trimethylsilyl)ethoxy)methyl)quinolin-2(1H)-one (65 mg, 0.120 mmol) in diethylether (20 mL) were added palladium (II) acetate (2.70 mg, 0.012 mmol) and a diazomethane solution [prepared from N-nitroso-N-methylurea (62.0 mg, 0.601 mmol) and KOH (33.7 mg, 0.61 mmol)]. The reaction was stirred at room temperature overnight, The reaction mixture was filtered through celite and concentrated to give trans-6-(2-(3-((4-(difluoromethoxy)-3-methylphenyl)amino)-1,2,4-oxadiazol-5-yl)cyclopropyl)-1-((2-(trimethylsilyl)ethoxy)methyl)quinolin-2(1H)-one (45 mg, 67%). LCMS, RT 2.25 min; LCMS (ES-API), m/z 555.

6-(2-(3-((4-(difluoromethoxy)-3-methylphenyl)amino)-1,2,4-oxadiazol-5-yl)cyclopropyl)quinolin-2(1H)-one

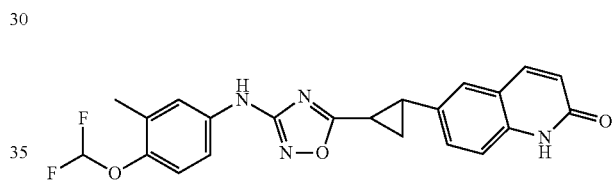

To a solution of 6-(2-(3-((4-(difluoromethoxy)-3-methylphenyl)amino)-1,2,4-oxadiazol-5-yl)cyclopropyl)-1-((2-(trimethylsilyl)ethoxy)methyl)quinolin-2(1H)-one (60 mg, 0.108 mmol) in DCM (2 mL) was added TFA (0.042 mL, 0.541 mmol) at 0° C. and the mixture was stirred at room temperature for 4 h. The reaction mixture was diluted with DCM and washed with sat. NaHCO$_3$ solution. The organic layer was dried Na$_2$SO$_4$, and concentrated. The crude product which was purified by preparative HPLC on a Sunfire C18 column (150×19, 5µ) using a buffer of mobile phase A: 0.1% TFA/Mobile Phase-B: ACN to give trans-6-(2-(3-((4-(difluoromethoxy)-3-methylphenyl)amino)-1,2,4-oxadiazol-5-yl)cyclopropyl)quinolin-2(1H)-one as an off white solid (12 mg, 11%). 1H NMR (400 MHz, DMSO-d6) δ ppm 1.70-1.83 (m, 2H) 2.22 (s, 3H) 2.56-2.64 (m, 1H) 2.72-2.78 (m, 1H) 6.51 (dd, J=9.54, 2.01 Hz, 1H) 6.84-7.15 (m, 2H) 7.24 (d, J=3.01 Hz, 1H) 7.29-7.35 (m, 2H) 7.43 (dd, J=8.66, 1.88 Hz, 1H) 7.58 (d, J=1.76 Hz, 1H) 7.84 (d, J=9.54 Hz, 1H) 9.83 (s, 1H) 11.72 (s, 1H). LCMS, RT 2.23 min; LCMS (ES-API), m/z 425.2.

The following compounds were synthesized by methods similar to that described for Example 235.

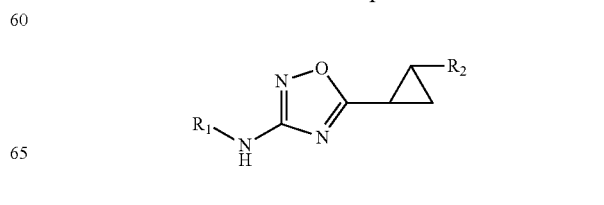

| Ex | R1 | R2 | LCMS RT (min) | LCMS Ion [M + H]+ | 1H NMR |
|----|----|----|---------------|-------------------|--------|
| 236 | F₂HCO- (with methyl) phenyl | 1H-indazol-5-yl | 1.946 | 398.2 | 400 MHz, DMSO-d6, δ ppm 1.70-1.84 (m, 2H) 2.19-2.26 (m, 3H) 2.55-2.60 (m, 1H) 2.76-2.86 (m, 1H) 6.84-7.13 (m, 2H) 7.23-7.38 (m, 3H) 7.49 (d, J = 8.53 Hz, 1H) 7.66 (s, 1H) 8.01 (s, 1H) 9.83 (s, 1H) 13.02 (s, 1H) |
| 237 | F₂HCO- (with Cl) phenyl | 2-oxo-1,2-dihydroquinolin-6-yl | 1.916 | 443 | 400 MHz, DMSO-d6, δ ppm 1.72-1.85 (m, 2H) 2.59 (dd, J = 9.03, 5.02 Hz, 1H) 2.71-2.81 (m, 1H) 6.48-6.53 (m, 1H) 6.95-7.27 (m, 2H) 7.32-7.37 (m, 1H) 7.41-7.48 (m, 2H) 7.58 (d, J = 1.51 Hz, 1H) 7.65 (d, J = 2.51 Hz, 1H) 7.84 (d, J = 9.54 Hz, 1H) 10.14 (s, 1H) 11.72 (s, 1H) |
| 238 | F₂HCO- (with F) phenyl | 1H-indazol-5-yl | 2.288 | 402.2 | 400 MHz, DMSO-d6, δ ppm 1.73-1.86 (m, 2H) 2.53-2.62 (m, 2H) 2.82 (ddd, J = 9.22, 6.59, 4.27 Hz, 1H) 7.08-7.39 (m, 4H) 7.42-7.52 (m, 2H) 7.66 (s, 1H) 8.01 (s, 1H) 10.16 (s, 1H) 13.02 (br. s., 1H) |

Example 239

6-((5-((3,4-dichlorophenyl)amino)-1,2,4-oxadiazol-3-yl)methoxy)-3,4-dihydroquinolin-2(1H)-one

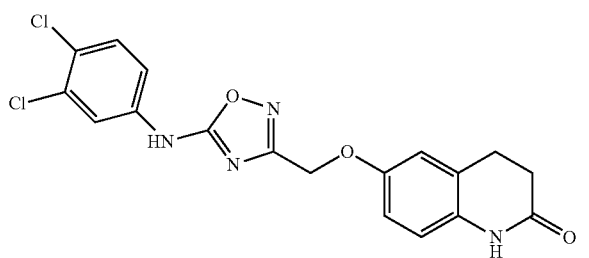 [SMILES: O=C1CCc2cc(OCc3noc(Nc4ccc(Cl)c(Cl)c4)n3)ccc2N1]

To a solution of (E)-N'-hydroxy-2-((2-oxo-1,2,3,4-tetrahydroquinolin-6-yl)oxy)acetimidamide (0.1 g, 0.425 mmol) in ethyl acetate (10 mL) was added a 0.5M solution of zinc chloride (0.073 mL, 0.510 mmol) followed by N-(3,4-dichlorophenyl)cyanamide (0.080 g, 0.425 mmol) and stirred at room temperature for 12 h. Then reaction mixture was concentrated. Ethanol (10.00 mL) was added along with HCl (0.1 mL, 3.29 mmol) and the reaction mixture was heated at 80° C. for 6 h. The reaction mixture was concentrated and basified with sodium bicarbonate solution, then the resulting solid was filtered and was washed with acetonitrile to give 6-((5-((3,4-dichlorophenyl)amino)-1,2,4-oxadiazol-3-yl)methoxy)-3,4-dihydroquinolin-2(1H)-one as a white solid (12 mg, 6.8% yield). 1H NMR 400 MHz, DMSO-d6: δ 2.41 (t, J=15.20 Hz, 2H), 2.84 (t, J=15.20 Hz, 2H), 4.94 (s, 2H), 6.77-6.79 (m, 1H), 6.84-6.87 (m, 1H), 6.93 (d, J=2.80 Hz, 1H), 7.30 (s, 1H), 7.37 (s, 1H), 7.80 (s, 1H), 9.91 (s, 1H). LCMS: RT 1.963 min; LCMS (ES-API), m/z 403.0 [M−H]⁻.

Example 240

6-((5-((3,4-dichlorophenylamino)-1,3,4-thiadiazol-2-yl)methoxy)-3,4-dihydroquinolin-2(1H)-one

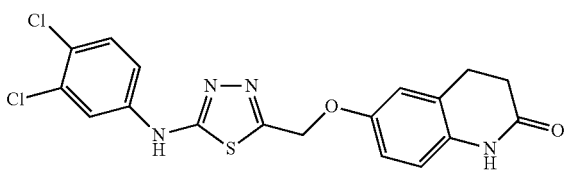 [SMILES: O=C1CCc2cc(OCc3nnc(Nc4ccc(Cl)c(Cl)c4)s3)ccc2N1]

N-(3,4-dichlorophenyl)-2-(2-((2-oxo-1,2,3,4-tetrahydroquinolin-6-yl)oxy)acetyl)hydrazinecarbothioamide (0.15 g, 0.341 mmol) and concentrated sulfuric acid (1 mL) were placed in a reaction beaker and the mixture was subjected to ultrasonic irradiation for 15 min. The reaction contents were poured into ice cold water. The precipitate was filtered and basified with 10% sodium bicarbonate (30 mL). Crude product was crystallized with ethanol/DMSO to afford 6-((5-(3, 4-dichlorophenylamino)-1,3,4-thiadiazol-2-yl)methoxy)-3,4-dihydroquinolin-2(1H)-one (0.045 g, 31%) as an off white solid. 1H NMR 400 MHZ, DMSO-d6: δ 2.42 (dd, J=7.20, 8.20 Hz, 2H), 2.85 (t, J=7.60 Hz, 2H), 5.37 (s, 2H), 6.79 (d, J=8.80 Hz, 1H), 6.88 (dd, J=2.40, 8.60 Hz, 1H), 6.95 (d, J=2.00 Hz, 1H), 7.48 (dd, J=2.40, 8.80 Hz, 1H), 8.08 (d, J=2.80 Hz, 1H), 9.96 (s, 1H), 10.75 (s, 1H). LCMS: RT 1.97 min, LCMS (ES-API), m/z 423.0 (M+H).

The following compounds were synthesized by a method similar to that described for Example 240.

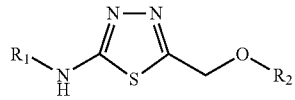

| Ex | R1 | R2 | LCMS RT (min) | LCMS [M + H]+ | 1H NMR |
|---|---|---|---|---|---|
| 241 | 4-(trifluoromethyl)phenyl | quinolin-2(1H)-one-6-yl | 1.87 | 419.0 | 1H NMR: 400 MHZ, DMSO-d6: δ 5.47 (s, 2H), 6.51 (d, J = 9.20 Hz, 1H), 7.28 (s, 2H), 7.40 (s, 1H), 7.71 (d, J = 8.80 Hz, 2H), 7.83 (dd, J = 6.40, Hz, 3H), 10.85 (s, 1H), 11.68 (s, 1H) |
| 242 | 4-(trifluoromethyl)phenyl | 3,4-dihydroquinolin-2(1H)-one-6-yl | 1.88 | 421.0 | 1H NMR: 400 MHZ, DMSO-d6: δ 2.41 (t, J = 7.20 Hz, 2H), 2.85 (t, J = 7.60 Hz, 2H), 5.37 (s, 2H), 6.79 (d, J = 8.80 Hz, 1H), 6.88 (d, J = 8.80 Hz, 1H), 6.95 (s, 1H), 7.71 (d, J = 8.40 Hz, 2H), 7.82 (d, J = 8.80 Hz, 2H), 9.95 (s, 1H), 10.80 (s, 1H) |
| 243 | 3,4-dichlorophenyl | quinolin-2(1H)-one-6-yl | 1.96 | 421.0 | 1H NMR: 400 MHZ, DMSO-d6: δ 5.46 (s, 2H), 6.52 (d, J = 9.60 Hz, 1H), 7.28 (d, J = 1.20 Hz, 2H), 7.40 (s, 1H), 7.48 (dd, J = 2.40, 9.00 Hz, 1H), 7.59 (d, J = 9.20 Hz, 1H), 7.85 (d, J = 9.60 Hz, 1H), 8.08 (d, J = 2.80 Hz, 1H), 10.76 (s, 1H), 11.68 (s, 1H) |
| 244 | 4-chlorophenyl | quinolin-2(1H)-one-6-yl | 1.82 | 385.0 | 1H NMR: 400 MHZ, DMSO-d6: δ 5.45 (s, 2H), 6.51 (d, J = 9.20 Hz, 1H), 7.28 (s, 2H), 7.40 (t, J = 2.00 Hz, 3H), 7.66 (d, J = 9.20 Hz, 2H), 7.84 (d, J = 9.60 Hz, 1H), 10.57 (s, 1H), 11.68 (s, 1H) |
| 245 | 4-(trifluoromethoxy)phenyl | quinolin-2(1H)-one-6-yl | 1.92 | 435.0 | 1H NMR: 400 MHZ, DMSO-d6: δ 5.45 (s, 2H), 6.52 (d, J = 9.60 Hz, 1H), 7.28 (s, 2H), 7.35-7.41 (m, 3H), 7.74 (d, J = 8.80 Hz, 2H), 7.85 (d, J = 9.60 Hz, 1H), 10.63 (s, 1H), 11.68 (s, 1H) |

-continued

| Ex | R1 | R2 | LCMS RT (min) | LCMS [M + H]⁺ | 1H NMR |
|---|---|---|---|---|---|
| 246 | 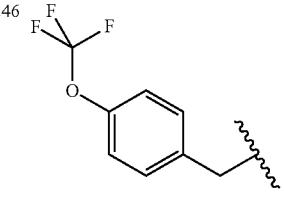 | 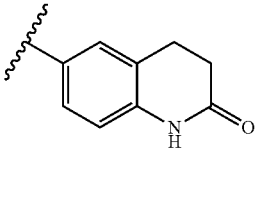 [SMILES: *c1ccc2c(c1)CCC(=O)N2] | 1.91 | 452.0 | 1H NMR: 400 MHZ, DMSO-d6: δ 2.40 (t, J = 6.80 Hz, 2H), 2.83 (t, J = 7.60 Hz, 2H), 4.52 (d, J = 6.00 Hz, 2H), 5.22 (s, 2H), 6.76-6.78 (m, 2H), 6.89 (d, J = 2.00 Hz, 1H), 7.35 (d, J = 8.00 Hz, 2H), 7.48 (d, J = 8.80 Hz, 2H), 8.36 (d, J = 5.60 Hz, 1H), 9.93 (s, 1H) |
| 247 | 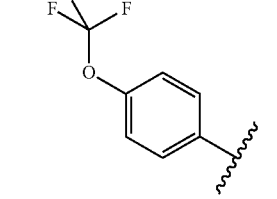 | 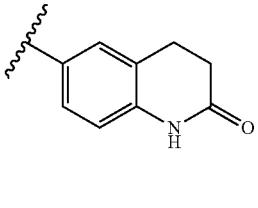 | 1.91 | 437.0 | 1H NMR: 400 MHZ, DMSO-d6: δ 2.40 (t, J = 7.20 Hz, 2H), 2.84 (t, J = 8.00 Hz, 2H), 5.35 (s, 2H), 6.79 (d, J = 8.80 Hz, 1H), 6.87 (dd, J = 2.80, 8.40 Hz, 1H), 6.94 (d, J = 2.80 Hz, 1H), 7.36 (d, J = 8.00 Hz, 2H), 7.73 (dd, J = 2.40, 7.00 Hz, 2H), 9.94 (s, 1H), 10.61 (s, 1H) |
| 248 | 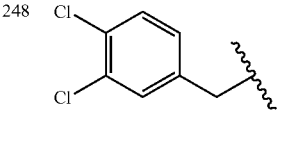 | 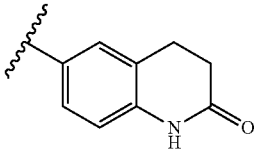 [SMILES: *c1ccc2c(c1)CCC(=O)N2] | 1.66 | 436.0 | 1H NMR: 400 MHZ, DMSO-d6: δ 2.40 (t, J = 7.20 Hz, 2H), 2.83 (t, J = 8.00 Hz, 2H), 4.50 (d, J = 6.00 Hz, 2H), 5.22 (s, 2H), 6.76-6.84 (m, 2H), 6.89 (d, J = 2.40 Hz, 1H), 7.35 (dd, J = 2.00, 8.40 Hz, 1H), 7.61 (d, J = 8.40 Hz, 2H), 8.38 (t, J = 5.60 Hz, 1H), 9.93 (s, 1H) |
| 249 | 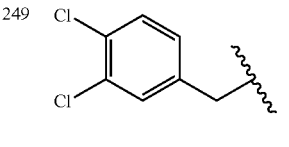 | 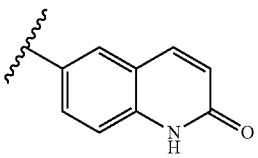 [SMILES: *c1ccc2[nH]c(=O)ccc2c1] | 1.66 | 435.0 | 1H NMR: 400 MHZ, DMSO-d6: δ 4.25 (s, 2H), 4.50 (d, J = 3.20 Hz, 2H), 5.32 (s, 2H), 6.50 (d, J = 9.60 Hz, 1H), 7.21-7.22 (m, 2H), 7.34-7.34 (m, 2H), 7.61 (dd, J = 2.00, 5.20 Hz, 2H), 7.83 (d, J = 7.20 Hz, 1H), 8.45 (s, 1H), 11.69 (s, 1H) |
| 250 | 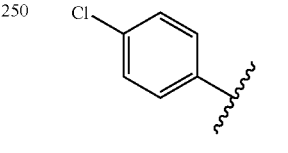 | 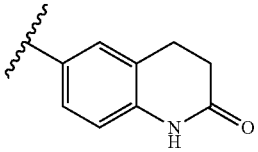 [SMILES: *c1ccc2c(c1)CCC(=O)N2] | 1.55 | 387.0 | 1H NMR: 400 MHZ, DMSO-d6: δ 2.40 (t, J = 7.20 Hz, 2H), 2.84 (t, J = 7.60 Hz, 2H), 5.35 (s, 2H), 6.79 (d, J = 8.40 Hz, 1H), 6.87 (dd, J = 2.4, 8.4 Hz, 1H), 6.94 (d, J = 2.80 Hz, 1H), 7.40 (d, J = 8.80 Hz, 2H), 7.66 (d, J = 8.80 Hz, 2H), 9.95 (s, 1H), 10.56 (s, 1H) |

-continued

| Ex | R1 | R2 | LCMS RT (min) | LCMS [M + H]+ | 1H NMR |
|---|---|---|---|---|---|
| 251 | 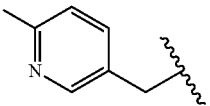 | 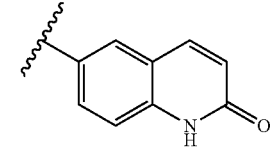 [SMILES: *c1ccc2[nH]c(=O)ccc2c1] | 1.24 | 400.0 | 1H NMR: 400 MHZ, DMSO-d6: δ 4.52 (s, 2H), 5.32 (s, 2H), 6.50 (d, J = 9.60 Hz, 2H), 7.23-7.27 (m, 2H), 7.35 (d, J = 2.00 Hz, 1H), 7.50 (d, J = 8.00 Hz, 1H), 7.81-7.85 (m, 2H), 8.41 (d, J = 2.00 Hz, 2H), 11.69 (s, 1H) |

Example 252

6-((2-(3,4-dichlorophenylamino)thiazol-4-yl)methoxy)-3,4-dihydroquinolin-2(1H)-one 6-(3-bromo-2-hydroxypropoxy)-3,4-dihydroquinolin-2(1H)-one

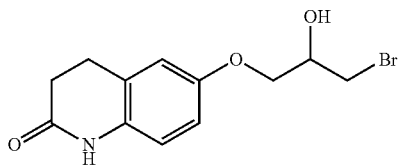 [SMILES: O=C1CCc2cc(OCC(O)CBr)ccc2N1]

To a stirred solution of 6-(oxiran-2-ylmethoxy)-3,4-dihydroquinolin-2(1H)-one (0.2 g, 0.909 mmol) in dry THF (5 mL) was added acetic acid (0.162 g, 2.272 mmol) and lithium bromide (0.118 g, 1.363 mmol). The reaction mixture was stirred at room temperature for 3 h. The reaction mixture was concentrated to remove solvent and water was added (25 mL). The solid was filtered and dried to give crude 6-(3-bromo-2-hydroxypropoxy)-3,4-dihydroquinolin-2(1H)-one as an off-white solid (0.25 g, 91.675 mmol). LCMS: RT 0.65 min; LCMS (ES-API), m/z 300.0 (M+H).

6-(3-bromo-2-oxopropoxy)-3,4-dihydroquinolin-2(1H)-one

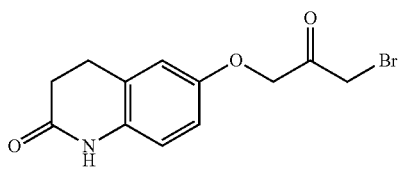 [SMILES: O=C(CBr)COc1ccc2c(c1)CCC(=O)N2]

To a stirred solution of 6-(3-bromo-2-hydroxypropoxy)-3,4-dihydroquinolin-2(1H)-one (0.2 g, 0.666 mmol) in DCM was added 4 Å molecular sieves powder (0.2 g) and pyridinium chlorochromate (0.287 g, 1.333 mmol). The reaction mixture was stirred at room temperature for 12 h. The reaction mixture was filtered through celite and washed with DCM (50 mL). The filtrate was concentrated and the crude product purified by flash chromatography on silica gel using 60% ethyl acetate in hexane to give 6-(3-bromo-2-oxopropoxy)-3,4-dihydroquinolin-2(1H)-one as an off white solid (0.15 g, 76%). LCMS: RT 0.67 min; LCMS (ES-API), m/z 298.0 (M+H).

6-((2-(3,4-dichlorophenylamino)thiazol-4-yl)methoxy)-3,4-dihydroquinolin-2(1H)-one

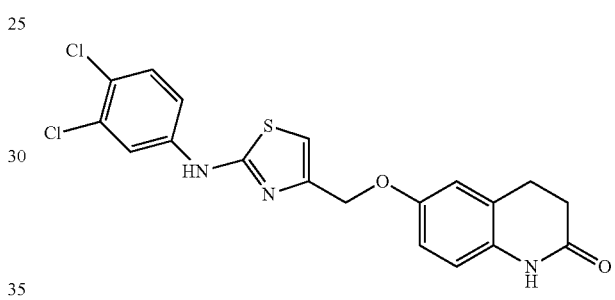

To a stirred solution of 6-(3-bromo-2-oxopropoxy)-3,4-dihydroquinolin-2(1H)-one (0.15 g, 0.503 mmol) in ethanol (3 mL) was added 1-(3,4-dichlorophenyl)thiourea (0.133 g, 0.604 mmol). The reaction mixture was refluxed for 12 h, then concentrated and purified by preparative HPLC to afford a white solid (0.05 g, 24%). $^1$H NMR 400 MHz, DMSO-d6: δ 2.40 (t, J=7.20 Hz, 2H), 2.85 (t, J=8.00 Hz, 2H), 4.99 (s, 2H), 6.80 (d, J=8.80 Hz, 1H), 6.87 (q, J=2.80 Hz, 1H), 6.92 (d, J=2.40 Hz, 1H), 6.98 (s, 1H), 7.48-7.49 (m, 2H), 8.06 (d, J=2.00 Hz, 1H), 9.92 (s, 1H), 10.56 (s, 1H). LCMS: RT 1.99 min; LCMS (ES-API), m/z 420. LCMS: RT 1.99 min; LCMS (ES-API), m/z 420.

Example 253

6-((3-(4-(difluoromethoxy)benzylamino)isoxazol-5-yl)methoxy)quinolin-2(1H)-one 6-(allyloxy)-3,4-dihydroquinolin-2(1H)-one 6-(allyloxy)-3,4-dihydroquinolin-2(1H)-one

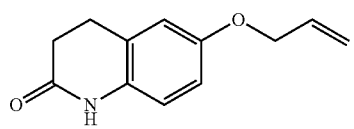

To a solution of 6-hydroxy-3,4-dihydroquinolin-2(1H)-one (1.5 g, 9.19 mmol) in DMF (20 mL), $K_2CO_3$ (2.54 g, 18.39 mmol) and allyl bromide (0.955 mL, 11.03 mmol) were added. The reaction mixture was stirred at room temperature for 3 h then concentrated. The residue was dissolved in ethyl acetate, washed with 10% NaOH solution, water, and brine. The organic layer was dried over anhydrous sodium sulfate, and concentrated to give 6-(allyloxy)-3,4-dihydroquinolin-2 (1H)-one as a white solid (1.7 g, 89%). 1HNMR: 400 MHz, DMSO-d6: δ 2.40 (q, J=7.60 Hz, 2H), 2.83 (t, J=8.00 Hz, 2H), 4.48-4.50 (m, 2H), 5.22-5.26 (m, 1H), 5.35-5.40 (m, 1H), 5.97-6.07 (m, 1H), 6.72-6.80 (m, 3H), 9.89 (s, 1H), LCMS (ES-API), RT 1.566 min, m/z 204.2 (M+H).

6-((3-bromo-4,5-dihydroisoxazol-5-yl)methoxy)-3,4-dihydroquinolin-2(1H)-one

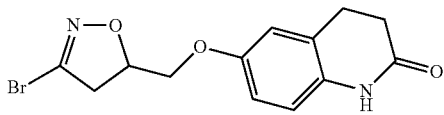 [SMILES: O=C1CCc2cc(OCC3CC(Br)=NO3)ccc2N1]

To a solution of 6-(allyloxy)-3,4-dihydroquinolin-2(1H)-one (1.85 g, 9.10 mmol) in DMF (20 mL) and water (5 mL), $K_2CO_3$ (3.77 g, 27.3 mmol) were added and the reaction mixture was cooled to 0° C. Hydroxycarbonimidic dibromide (3.69 g, 18.21 mmol) was added and the reaction mixture was stirred at room temperature overnight. The reaction mixture was diluted with ethyl acetate and washed with water, brine, and dried over $Na_2SO_4$. The organic layer was concentrated and the crude material purified by flash chromatography on silica gel using ethyl acetate/hexane as eluant to give 6-((3-bromo-4,5-dihydroisoxazol-5-yl)methoxy)-3,4-dihydro-quinolin-2(1H)-one as a white solid (1.8 g, 59.6%). $^1$HNMR: 400 MHz, DMSO-d6: δ 2.40 (q, J=7.20 Hz, 2H), 2.83 (t, J=8.00 Hz, 2H), 3.18 (dd, J=7.60, 17.60 Hz, 1H), 3.50 (dd, J=10.80, 17.40 Hz, 1H), 4.01-4.09 (m, 2H), 4.98-5.03 (m, 1H), 6.72-6.81 (m, 3H), 9.92 (s, 1H). LCMS: RT 1.408 min; LCMS (ES-API), m/z 327 (M+H).

6-((3-(4-(difluoromethoxy)benzylamino)-4,5-dihydroisoxazol-5-yl)methoxy)-3,4-dihydroquinolin-2(1H)-one

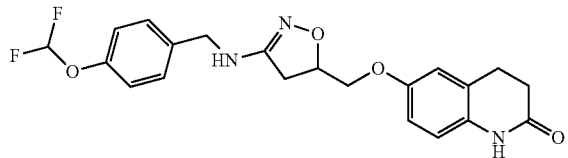 [SMILES: O=C1CCc2cc(OCC3CC(NCc4ccc(OC(F)F)cc4)=NO3)ccc2N1]

6-((3-bromo-4,5-dihydroisoxazol-5-yl)methoxy)-3,4-dihydroquinolin-2(1H)-one (0.1 g, 0.308 mmol) and (4-(difluoromethoxy)phenyl)methanamine (0.149 g, 0.923 mmol) were heated at 160° C. for 30 min. The reaction mixture was dissolved in methanol, concentrated, and the crude product purified by preparative HPLC on a Kromasil C4 column (250×20 mm) using a 0-100% gradient of ACN in 0.1% TFA to give 6-((3-(4-(difluoromethoxy)benzylamino)-4,5-dihydroisoxazol-5-yl)methoxy)-3,4-dihydroquinolin-2(1H)-one as a white solid (0.015 g, 23%). $^1$H NMR 400 MHz, DMSO-d6: δ 2.41 (q, J=7.20 Hz, 2H), 2.78-2.85 (m, 3H), 3.08 (q, J=9.60 Hz, 1H), 3.89-3.97 (m, 2H), 4.18 (d, J=6.00 Hz, 2H), 4.62-4.65 (m, 1H), 6.62 (t, J=6.00 Hz, 1H), 6.72-6.78 (m, 2H), 6.81 (d, J=2.00 Hz, 1H), 7.02-7.39 (m, 5H), 9.91 (s, 1H). LCMS: RT 1.501 min; LCMS (ES-API), m/z 418.2 (M+H).

6-((3-(4-(difluoromethoxy)benzylamino)isoxazol-5-yl)methoxy)quinolin-2(1H)-one

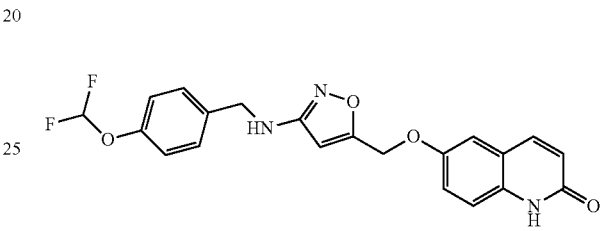

Into a sealed tube was placed a solution of 6-((3-((4-(difluoromethoxy)benzyl)amino)-4,5-dihydroisoxazol-5-yl)methoxy)-3,4-dihydroquinolin-2(1H)-one (0.12 g, 0.287 mmol), imidazole (0.117 g, 1.725 mmol), and iodine (0.219 g, 0.862 mmol) in toluene (5 mL). The tube was sealed and heated at 110° C. for 24 h. The reaction mixture was diluted with ethyl acetate, washed with 10% $Na_2S_2O_4$ and brine, dried over $Na_2SO_4$, and concentrated. The crude product was purified by preparative HPLC on an Xbridge phenyl column (150×19×5μ) using a 10 mM $NH_4OAc$/ACN gradient (0-100%) to give 6-((3-(4-(difluoromethoxy)benzylamino)isoxazol-5-yl)methoxy)quinolin-2(1H)-one as a white solid (0.023 g, 23%). 1HNMR: 400 MHz, DMSO-d6: δ 4.24 (d, J=6.00 Hz, 2H), 5.11 (s, 2H), 6.06 (s, 1H), 6.51 (d, J=9.20 Hz, 1H), 6.73 (t, J=6.00 Hz, 1H), 7.01-7.39 (m, 8H), 7.83 (d, J=9.60 Hz, 1H), 11.66 (s, 1H). LCMS: RT 1.558 min; LCMS (ES-API), m/z 412.0 (M−H).

The following compounds were synthesized by a method similar to that described for Example 253.

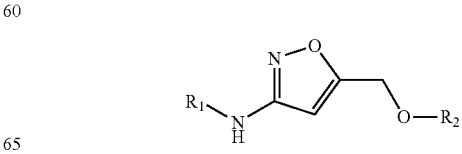

| Ex | R1 | R2 | LCMS RT (min) | LCMS Ion [M + H]+ | 1H NMR |
|---|---|---|---|---|---|
| 254 | 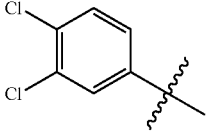 [SMILES: *c1ccc(Cl)c(Cl)c1] | 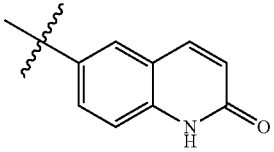 [SMILES: *c1ccc2[nH]c(=O)ccc2c1] | 1.983 | 402.0 | 400 MHz, DMSO-d6: δ 5.26 (s, 2H), 6.31 (s, 1H), 6.52 (d, J = 9.60 Hz, 1H), 7.27 (s, 2H), 7.33 (dd, J = 2.80, 8.80 Hz, 1H), 7.38 (s, 1H), 7.53 (d, J = 8.80 Hz, 1H), 7.75 (d, J = 2.40 Hz, 1H), 7.84 (d, J = 9.60 Hz, 1H), 9.60 (s, 1H), 11.67 (s, 1H) |
| 255 | 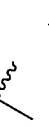 | 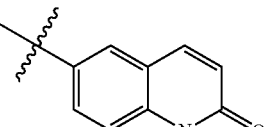 | 1.875 | 434.0 | 400 MHz, DMSO-d6: δ 1.19 (t, J = 7.20 Hz, 2H), 3.11 (s, 1H), 5.26 (s, 2H), 6.29 (s, 1H), 6.52 (dd, J = 1.60, 9.40 Hz, 1H), 6.95-7.38 (m, 6H), 7.70 (d, J = 2.00 Hz, 1H), 7.84 (d, J = 9.60 Hz, 1H), 9.51 (s, 1H), 11.67 (s, 1H) |
| 256 | 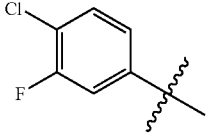 | 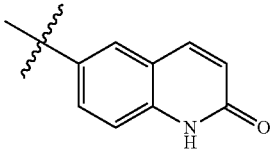 [SMILES: *c1ccc2[nH]c(=O)ccc2c1] | 1.897 | 386.0 | 400 MHz, DMSO-d6: δ 5.25 (s, 2H), 6.30 (s, 1H), 6.51 (dd, J = 1.60, 9.40 Hz, 1H), 7.17 (dd, J = 0.40, 2.60 Hz, 1H), 7.27 (J = 1.60, 2H), 7.38 (s, 1H), 7.47-7.53 (m, 2H), 7.84 (d, J = 9.60 Hz, 1H), 9.64 (s, 1H), 11.68 (s, 1H) |
| 257 | 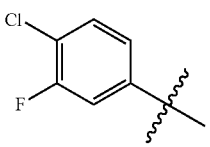 [SMILES: *c1ccc(Cl)c(F)c1] | 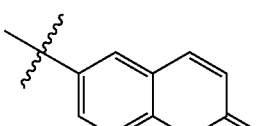 | 1.764 | 386.0 | 400 MHz, DMSO-d6: δ 6.31 (s, 1H), 6.52 (d, J = 9.60 Hz, 1H), 7.18-7.21 (m, 1H), 7.27 (s, 2H), 7.38 (d, J = 0.80 Hz, 1H), 7.45-7.54 (m, 2H), 7.84 (d, J = 9.60 Hz, 1H), 9.67 (s, 1H), 11.67 (s, 1H) |
| 258 | 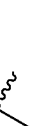 | 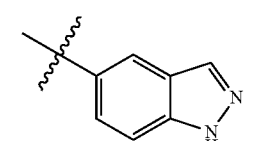 | 1.837 | 407.0 | 400 MHz, DMSO-d6: δ 6.30 (s, 1H), 6.95-7.36 (m, 6H), 7.49 (d, J = 9.20 Hz, 1H), 7.70 (t, J = 0.40 Hz, 1H), 7.98 (d, J = 0.80 Hz, 1H), 9.53 (s, 1H), 12.99 (s, 1H) |
| 260 | 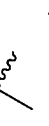 | 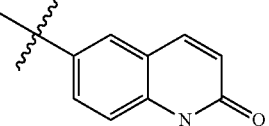 | 1.794 | 400.0 | 400 MHz, DMSO-d6: δ 5.24 (s, 2H), 6.26 (s, 1H), 6.51 (dd, J = 1.60, 9.40 Hz, 1H), 6.90-7.44 (m, 5H), 7.45 (s, 1H), 7.46 (d, J = 3.60 Hz, 2H), 7.84 (d, J = 9.60 Hz, 1H), 9.27 (s, 1H), 11.67 (s, 1H) |
| 261 | 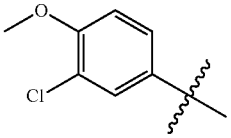 [SMILES: *c1ccc(OC)c(Cl)c1] | 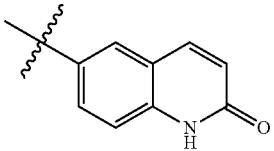 [SMILES: *c1ccc2[nH]c(=O)ccc2c1] | 1.468 | 398.0 | 400 MHz, DMSO-d6: 3.81 (s, 3H), 5.24 (s, 2H), 6.23 (s, 1H), 6.51 (dd, J = 2.00, 9.40 Hz, 1H), 7.11 (d, J = 9.20 Hz, 1H), 7.27-7.31 (m, 3H), 7.38 (s, 1H), 7.57 (d, J = 2.80 Hz, 1H), 7.84 (d, J = 9.60 Hz, 1H), 9.16 (s, 1H), 11.67 (s, 1H) |
| 262 | 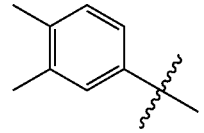 [SMILES: *c1ccc(C)c(C)c1] | 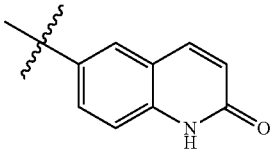 [SMILES: *c1ccc2[nH]c(=O)ccc2c1] | 1.58 | 362.2 | 400 MHz, DMSO-d6: δ 2.17 (d, J = 17.20 Hz, 6H), 5.22 (s, 2H), 6.21 (s, 1H), 6.51 (dd, J = 2.00, 9.60 Hz, 1H), 7.03 (d, J = 8.00 Hz, 1H), 7.13-7.17 (m, 2H), 7.26 (s, 2H), 7.37 (s, 1H), 7.84 (d, J = 9.60 Hz, 1H), 8.97 (s, 1H), 11.68 (s, 1H),. |

| Ex | R1 | R2 | LCMS RT (min) | LCMS Ion [M + H]+ | 1H NMR |
|---|---|---|---|---|---|
| 263 | 4-Cl, 3-CF3-phenyl | 6-quinolin-2(1H)-one | 1.825 | 436.0 | 400 MHz, DMSO-d6: δ 5.26 (s, 2H), 6.33 (s, 1H), 6.51 (dd, J = 2.00, 9.60 Hz, 1H), 7.27 (d, J = 1.60 Hz, 2H), 7.38 (s, 1H), 7.62-7.67 (m, 2H), 7.84 (d, J = 9.60 Hz, 1H), 7.95 (d, J = 2.40 Hz, 1H), 9.79 (s, 1H), 11.68 (s, 1H) |
| 264 | 4-CF3-phenyl | 6-quinolin-2(1H)-one | 1.666 | 402.0 | 400 MHz, DMSO-d6: δ 5.27 (s, 2H), 6.34 (s, 1H), 6.51 (dd, J = 2.00, 9.60 Hz, 1H), 7.27 (d, J = 1.60 Hz, 2H), 7.39 (s, 1H), 7.58 (d, J = 8.40 Hz, 2H), 7.65 (d, J = 8.80 Hz, 2H), 7.84 (d, J = 9.60 Hz, 1H), 9.71 (s, 1H), 11.69 (s, 1H) |
| 265 | 4-ethyl-phenyl | 6-quinolin-2(1H)-one | 1.611 | 362.2 | 400 MHz, DMSO-d6: δ 1.15 (t, J = 7.60 Hz, 3H), 2.54 (s, 2H), 5.23 (s, 2H), 6.23 (s, 1H), 6.51 (dd, J = 2.00, 9.60 Hz, 1H), 7.12 (d, J = 8.80 Hz, 2H), 7.26-7.38 (m, 5H), 7.84 (d, J = 9.60 Hz, 1H), 9.07 (s, 1H), 11.68 (s, 1H) |
| 266 | 4-propyl-phenyl | 6-quinolin-2(1H)-one | 1.767 | 376.2 | 400 MHz, DMSO-d6: δ 0.87 (t, J = 2.40 Hz, 3H), 1.56 (q, J = 7.60 Hz, 2H), 2.47 (d, J = 7.60 Hz, 2H), 5.22 (s, 2H), 6.23 (s, 1H), 6.51 (dd, J = 2.00, 9.60 Hz, 1H), 7.10 (d, J = 8.80 Hz, 2H), 7.26-7.37 (m, 5H), 7.84 (d, J = 9.60 Hz, 1H), 9.07 (s, 1H), 11.66 (s, 1H) |
| 267 | 4-OCHF2, 3-F-phenyl | 6-quinolin-2(1H)-one | 1.562 | 418.0 | 400 MHz, DMSO-d6: δ 5.25 (s, 2H), 6.30 (s, 1H), 6.51 (dd, J = 2.00, 9.60 Hz, 1H), 6.93-7.38 (m, 6H), 7.49 (dd, J = 2.80, 13.20 Hz, 1H), 7.84 (d, J = 9.60 Hz, 1H), 9.55 (s, 1H), 11.68 (s, 1H) |
| 268 | 4-OCHF2, 3-methyl-phenyl | 6-quinolin-2(1H)-one | 1.578 | 414.2 | 400 MHz, DMSO-d6: δ 2.21 (s, 3H), 5.23 (s, 2H), 6.25 (s, 1H), 6.51 (dd, J = 2.00, 9.60 Hz, 1H), 6.85-7.32 (m, 6H), 7.38 (s, 1H), 7.84 (d, J = 9.60 Hz, 1H), 9.20 (s, 1H), 11.68 (s, 1H) |
| 269 | 4-CF3, 3-Cl-phenyl | 6-quinolin-2(1H)-one | 1.817 | 436.0 | 400 MHz, DMSO-d6: δ 5.28 (s, 2H), 6.37 (s, 1H), 6.51 (dd, J = 2.00, 9.60 Hz, 1H), 7.27 (d, J = 1.60 Hz, 2H), 7.39 (s, 1H), 7.46 (dd, J = 2.00, 9.00 Hz, 1H), 7.76 (t, J = 2.40 Hz, 2H), 7.84 (d, J = 9.60 Hz, 1H), 9.96 (s, 1H), 11.69 (s, 1H) |
| 270 | 4-F, 3-methyl-phenyl | 6-quinolin-2(1H)-one | 1.504 | 366.2 | 400 MHz, DMSO-d6: δ 2.21 (d, J = 1.60 Hz, 3H), 5.23 (s, 2H), 6.23 (s, 1H), 6.51 (dd, J = 2.00, 9.40 Hz, 1H), 7.06 (t, J = 9.20 Hz, 1H), 7.22-7.30 (m, 4H), 7.38 (s, 1H), 7.84 (d, J = 9.60 Hz, 1H), 9.12 (s, 1H), 11.68 (s, 1H) |

| Ex | R1 | R2 | LCMS RT (min) | LCMS Ion [M + H]+ | 1H NMR |
|---|---|---|---|---|---|
| 271 | 4-methyl-3-fluorophenyl | 5-indazolyl | 2.042 | 339.1 | 400 MHz, DMSO-d6: δ 2.15 (d, J = 1.20 Hz, 3H), 5.22 (s, 2H), 6.26 (d, J = 11.60 Hz, 1H), 7.03-7.35 (m, 5H), 7.48 (d, J = 12.00 Hz, 1H), 7.97 (s, 1H), 9.31 (s, 1H), 12.96 (s, 1H) |
| 272 | 4-(difluoromethoxy)-3-methylphenyl | 5-indazolyl | 2.064 | 387.1 | 400 MHz, DMSO-d6: δ 2.21 (s, 3H), 5.22 (s, 2H), 6.24 (s, 1H), 6.78-7.35 (m, 6H), 7.48 (d, J = 11.60 Hz, 1H), 7.97 (s, 1H), 9.18 (s, 1H), 12.96 (s, 1H) |
| 273 | 4-ethylphenyl | 5-indazolyl | 2.125 | 335.2 | 400 MHz, DMSO-d6: δ 1.15 (t, J = 10.00 Hz, 3H), 2.54 (s, 2H), 5.21 (s, 2H), 6.22 (s, 1H), 7.07-7.13 (m, 3H), 7.30-7.35 (m, 3H), 7.48 (d, J = 12.00 Hz, 1H), 7.97 (s, 1H), 9.04 (s, 1H), 12.96 (s, 1H) |
| 274 | 4-(difluoromethoxy)-3-fluorophenyl | 5-indazolyl | 2.022 | 391.1 | 400 MHz, DMSO-d6: δ 5.24 (s, 2H), 6.29 (s, 1H), 6.86-7.35 (m, 5H), 7.46-7.51 (m, 2H), 7.97 (s, 1H), 9.53 (s, 1H), 12.96 (s, 1H) |
| 275 | 4-(difluoromethoxy)phenyl | 5-indazolyl | 1.93 | 373.1 | 400 MHz, DMSO-d6: δ 5.22 (s, 2H), 6.25 (s, 1H), 6.84-7.35 (m, 5H), 7.42-7.49 (m, 3H), 7.97 (s, 1H), 9.26 (s, 1H), 12.96 (s, 1H) |

Example 276

6-((5-(3,4-dichlorophenylamino)-4-methyl-4H-1,2,4-triazol-3-yl)methoxy)quinolin-2(1H)-one 1-(3,4-dichlorophenyl)-3-methylthiourea

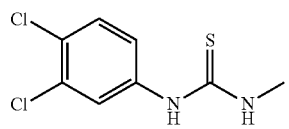

To a stirred solution of 1,2-dichloro-4-isothiocyanatobenzene (1 g, 4.9 mmol) in ethanol (30 mL) was added 8M methyl amine in ethanol (0.613 mL, 4.9 mmol) and the reaction was heated at 80° C. overnight. The solvent was removed under vacuum and the residue was washed with diethyl ether (10 mL) and dried to give crude 1-(3,4-dichlorophenyl)-3-methylthiourea as an off white solid (0.8 g, 69%). 1HNMR: 400 MHz, DMSO-d6: δ 2.93 (d, J=4.40 Hz, 3H), 7.37 (d, J=7.60 Hz, 1H), 7.55 (d, J=8.40 Hz, 1H), 7.86 (d, J=2.40 Hz, 1H), 7.92 (bs, 1H), 9.74 (bs, 1H).

(Z)-methyl N'-3,4-dichlorophenyl-N-methylcarbamimidothioate hydroiodide

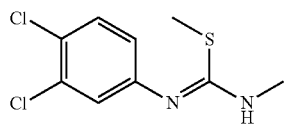

To a stirred solution of 1-(3,4-dichlorophenyl)-3-methylthiourea (0.33 g, 1.403 mmol) in acetone (10 mL), MeI (0.26 ml, 4.21 mmol) was added and the reaction was heated at 45° C. overnight. Completion of the reaction was monitored by LCMS. Solvent was removed under vacuum, and then water (10 mL) was added to the residue. The solid was filtered and dried to yield crude (Z)-methyl N'-3,4-dichlorophenyl-N-methylcarbamimidothioate hydroiodide as a yellow solid (0.32 g, 92%). 1HNMR: 400 MHz, DMSO-d6: δ 2.62 (d, J=10.00 Hz, 3H), 3.38 (s, 3H), 7.35 (d, J=7.60 Hz, 1H), 7.70 (s, 1H), 7.77 (d, J=8.80 Hz, 1H), 9.12 (bs, 1H).

6-((5-(3,4-dichlorophenylamino)-4-methyl-4H-1,2,4-triazol-3-yl)methoxy)quinolin-2(1H)-one

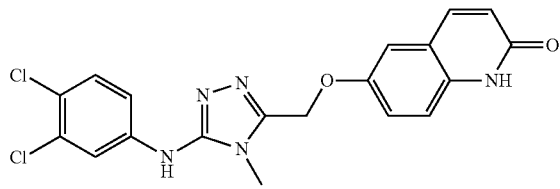 [SMILES: Cn1c(COc2ccc3[nH]c(=O)ccc3c2)nnc1Nc1ccc(Cl)c(Cl)c1]

To a stirred solution of 2-((2-oxo-1,2-dihydroquinolin-6-yl)oxy)acetohydrazide (0.15 g, 0.693 mmol) in DMSO (5 mL), (Z)-methyl N'-3,4-dichlorophenyl-N-methylcarbamimidothioate hydroiodide (0.15 g, 0.398 mmol) and TEA (0.2 ml, 1.608 mmol) were added and the reaction was heated at 115° C. in a seal tube for 72 h. Ice cold water was added to the reaction mixture and the precipitate was filtered and dried. The crude product was purified by preparative HPLC on a Sunfire C18 column (150×19, 5μ) using a 0-55% gradient of ACN in 0.05% TFA to give 6-((5-(3,4-dichlorophenylamino)-4-methyl-4H-1,2,4-triazol-3-yl)methoxy)quinolin-2(1H)-one as an off white solid (0.03 g, 11%). 1HNMR:400 MHz, DMSO-d6: δ 3.58 (s, 3H), 5.27 (s, 2H), 6.52 (d, J=9.60 Hz, 1H), 7.28 (d, J=2.00 Hz, 2H), 7.43 (s, 1H), 7.53 (d, J=2.00 Hz, 2H), 7.85 (d, J=9.60 Hz, 1H), 7.99-7.99 (m, 1H), 9.19 (s, 1H), 11.67 (s, 1H). LCMS: RT 1.732 min; LCMS (ES-API), m/z 402.0 (M+H).

Example 277

5-(2-(1H-indazol-5-yl)ethyl)-N-(4-(difluoromethoxy)phenyl)-4-methyl-4H-1,2,4-triazol-3-amine

5-bromo-1-(tetrahydro-2H-pyran-2-yl)-1H-indazole

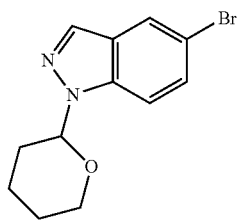 [SMILES: Brc1ccc2c(cnn2C2CCCCO2)c1]

To a solution of 5-bromo-1H-indazole (5 g, 25.38 mmol) in DCM (50 mL), 3,4-dihydro-2H-pyran (4.26 g, 50.76 mmol) and PTSA (2.41 g, 12.69 mmol) were added and the reaction was stirred at room temperature for 3 h. Solvent was removed under vacuum. The residue was dissolved in ethyl acetate (150 mL), washed with water (20 mL), brine (20 mL), and dried over sodium sulfate. The organic layer was concentrated under vacuum and the crude product was purified by flash chromatography using hexane/ethyl acetate to give 5-bromo-1-(tetrahydro-2H-pyran-2-yl)-1H-indazole as colorless liquid (6.95 g, 97%). 1HNMR: 400 MHz, DMSO-d6: δ 1.57-1.62 (m, 2H), 1.74-1.76 (m, 1H), 1.96-2.06 (m, 2H), 2.37-2.40 (m, 1H), 3.72-3.78 (m, 1H), 3.87-3.90 (m, 1H), 5.85-5.86 (m, 1H), 7.53-7.54 (m, 1H), 7.74 (d, J=9.20 Hz, 1H), 8.04 (d, J=1.60 Hz, 1H), 8.11 (s, 1H). LCMS: RT 2.033 min; LCMS (ES-API), m/z 283 (M+H).

(E)-ethyl 3-(1-(tetrahydro-2H-pyran-2-yl)-1H-indazol-5-yl)acrylate

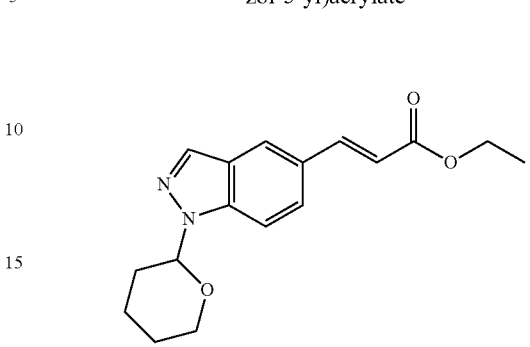

To a solution of 5-bromo-1-(tetrahydro-2H-pyran-2-yl)-1H-indazole (0.85 g, 3.02 mmol) in ACN (20 mL), ethyl acrylate (0.605 g, 6.05 mmol), tri-o-tolylphosphine (0.368 g, 1.209 mmol), and TEA (1.204 ml, 9.07 mmol) were added. The reaction mixture was purged with nitrogen and then $Pd_2(dba)_3$ CHCl3 adduct (0.313 g, 0.302 mmol) was added. The reaction was heated at 90° C. overnight. The solvent was removed under vacuum. The residue was dissolved in ethyl acetate (15 mL), washed with water (10 mL), brine (10 mL), and dried over sodium sulfate. The organic layer was concentrated under vacuum and the crude product was purified by flash chromatography on silica gel using hexane/ethyl acetate to give of (E)-ethyl 3-(1-(tetrahydro-2H-pyran-2-yl)-1H-indazol-5-yl)acrylate as a yellow liquid (0.78 g, 76%). 1HNMR: 400 MHz, DMSO-d6: δ 1.25-1.26 (m, 3H), 1.58-1.62 (m, 2H), 1.76-1.77 (m, 1H), 1.97-2.07 (m, 2H), 2.39-2.42 (m, 1H), 3.73-3.79 (m, 1H), 3.88-3.91 (m, 1H), 4.21 (q, J=7.20 Hz, 2H), 5.87-5.88 (m, 1H), 6.64 (d, J=15.60 Hz, 1H), 7.76-7.77 (m, 2H), 7.81-7.87 (m, 1H), 8.12 (s, 1H), 8.18 (s, 1H). LCMS: RT 1.01 min; LCMS (ES-API), m/z 217 (M-THP).

Ethyl 3-(1-(tetrahydro-2H-pyran-2-yl)-1H-indazol-5-yl)propanoate

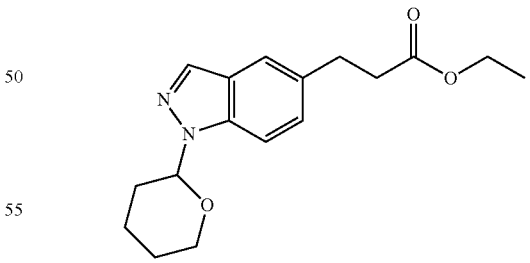

A stirred solution of (E)-ethyl 3-(1-(tetrahydro-2H-pyran-2-yl)-1H-indazol-5-yl)acrylate (0.78 g, 2.60 mmol) in MeOH (30 mL) and Pd/C (100 mg, 0.094 mmol) was stirred under hydrogen atmosphere overnight. The reaction mixture was filtered through celite, and the filtrate was concentrated and dried to give ethyl 3-(1-(tetrahydro-2H-pyran-2-yl)-1H-indazol-5-yl)propanoate (0.59 g, 75%), used without further purification. 1HNMR: 400 MHz, DMSO-d6: δ 1.13-1.15 (m, 3H), 1.56-1.57 (m, 2H), 1.58-1.59 (m, 1H), 1.93-2.05 (m, 2H), 2.39-2.50 (m, 1H), 2.63-2.69 (m, 2H), 2.94-2.96 (m, 2H), 3.58 (s, 1H), 3.71-3.76 (m, 1H), 3.86-3.89 (m, 1H), 4.04 (q, J=6.80 Hz, 2H), 5.79-5.80 (m, 1H), 7.29-7.31 (m, 1H), 7.57-7.62 (m, 2H), 8.18 (s, 1H). LCMS: RT 0.99 min; LCMS (ES-API), m/z 219 (M-THP).

3-(1-(tetrahydro-2H-pyran-2-yl)-1H-indazol-5-yl) propanehydrazide

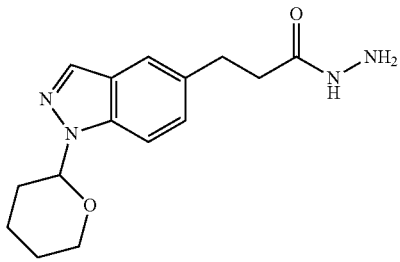 [SMILES: NNC(=O)CCc1ccc2c(cnn2C2CCCCO2)c1]

To a stirred solution of ethyl 3-(1-(tetrahydro-2H-pyran-2-yl)-1H-indazol-5-yl)propanoate (0.59 g, 1.951 mmol) in ethanol (5 mL) was added hydrazine hydrate (0.306 mL, 9.76 mmol) and the reaction was heated at 80° C. overnight. The solid which formed was filtered and dried to afford 3-(1-(tetrahydro-2H-pyran-2-yl)-1H-indazol-5-yl) propanehydrazide (0.56 g, 82%), used without further purification. 1HNMR: 400 MHz, DMSO-d6: δ 1.58-1.59 (m, 2H), 1.92-1.96 (m, 1H), 1.97-2021.00 (m, 1H), 2.34-2.42 (m, 3H), 2.90-2.92 (m, 2H), 3.72-3.76 (m, 1H), 3.86-3.89 (m, 1H), 4.14 (s, 4H), 5.79-5.79 (m, 1H), 7.25-7.26 (m, 1H), 7.54 (s, 1H), 7.62 (d, J=8.80 Hz, 1H), 8.01 (s, 1H), 8.94 (s, 2H). LCMS: RT 0.64 min; LCMS (ES-API), m/z 205 (M-THP).

1-(4-(difluoromethoxy)phenyl)-3-methylthiourea

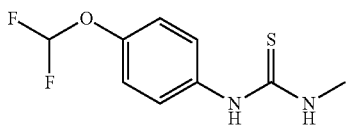

By a procedure analogous to the synthesis of 1-(3,4-dichlorophenyl)-3-methylthiourea in (Example 276), 1-(4-(difluoromethoxy)phenyl)-3-methylthiourea was synthesized as off white solid (1 g, 86%). 1HNMR: 400 MHz, DMSO-d6: δ 2.91 (d, J=4.40 Hz, 3H), 6.99-7.11 (m, 3H), 7.37-7.43 (m, 2H), 7.71 (bs, 1H), 9.56 (bs, 1H).

(Z)-methyl N'-4-(difluoromethoxy)phenyl-N-methyl-carbamimidothioate hydroiodide

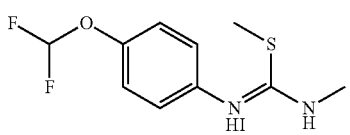

By a procedure analogous to the synthesis of (Z)-methyl N'-3,4-dichlorophenyl-N-methylcarbamimidothioate hydroiodide (Example 276), (Z)-methyl N'-4-(difluoromethoxy)phenyl-N-methylcarbamimidothioate hydroiodide was synthesized as a yellow solid (0.8 g, 59%). 1HNMR: 400 MHz, DMSO-d6: δ 7.14-7.51 (m, 1H), 7.32 (d, J=2.40 Hz, 2H), 7.43 (d, J=8.80 Hz, 2H).

N-(4-(difluoromethoxy)phenyl)-4-methyl-5-(2-(1-(tetrahydro-2H-pyran-2-yl)-1H-indazol-5-yl)ethyl)-4H-1,2,4-triazol-3-amine

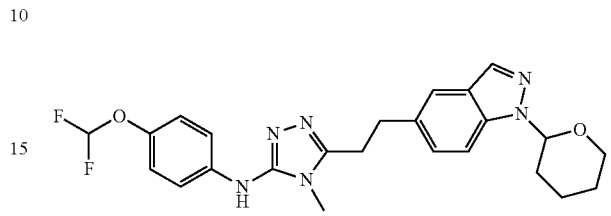

By a procedure analogous to the synthesis of 6-((5-(3,4-dichlorophenylamino)-4-methyl-4H-1,2,4-triazol-3-yl)methoxy)quinolin-2(1H)-one (Example 276), 5-(2-(1H-indazol-5-yl)ethyl)-N-(4-(difluoromethoxy)phenyl)-4-methyl-4H-1,2,4-triazol-3-amine (0.131 g, 16%) was synthesized as an off-white gum. LCMS: RT 1.858 min; LCMS (ES-API), m/z 469 (M+H).

5-(2-(1H-indazol-5-yl)ethyl)-N-(4-(difluoromethoxy)phenyl)-4-methyl-4H-1,2,4-triazol-3-amine

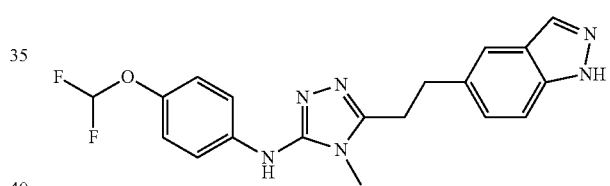

To a stirred solution of N-(4-(difluoromethoxy)phenyl)-4-methyl-5-(2-(1-(tetrahydro-2H-pyran-2-yl)-1H-indazol-5-yl)ethyl)-4H-1,2,4-triazol-3-amine (131 mg, 0.280 mmol) in DCM (2 mL), was added TFA (0.646 mL, 8.39 mmol) and the reaction was stirred at room temperature overnight. Solvents were concentrated and the crude product was purified by preparative HPLC on a Sunfire C18 column (150×19×5.0 m) using a gradient of ACN in 10 mM ammonium acetate (0-100%) to give 5-(2-(1H-indazol-5-yl)ethyl)-N-(4-(difluoromethoxy)phenyl)-4-methyl-4H-1,2,4-triazol-3-amine as off white solid (0.026 g, 23%). 1HNMR: 400 MHz, DMSO-d6: δ 2.96-2.98 (m, 2H), 3.08-3.10 (m, 2H), 3.34 (s, 3H), 7.07-7.09 (m, 3H), 7.27-7.28 (m, 1H), 7.47-7.49 (m, 3H), 7.63 (s, 1H), 8.00 (s, 1H), 8.57 (s, 1H), 12.98 (s, 1H). LCMS: RT 1.322 min; LCMS (ES-API), m/z 385 (M+H).

The following examples were synthesized by methods similar to those used for Examples 276 and 277.

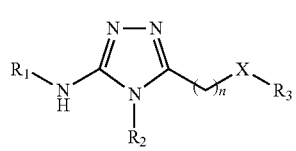

| Ex | R1 | R2 | R3 | n | X | LCMS RT (min) | LCMS Ion [M + H]+ | 1H NMR |
|---|---|---|---|---|---|---|---|---|
| 278 | 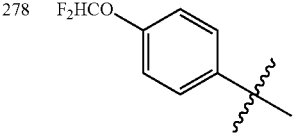 | Me | 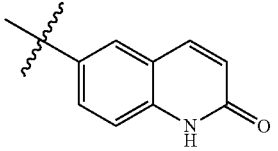 [SMILES: *c1ccc2[nH]c(=O)ccc2c1] | 1 | O | 1.318 | 414.0 | 400 MHz, DMSO-d6: δ 3.62 (s, 3H), 5.30 (s, 2H), 6.53 (d, J = 9.60 Hz, 1H), 7.15-7.17 (m, 2H), 7.27-7.29 (m, 2H), 7.33 (d, J = 8.80 Hz, 1H), 7.55-7.56 (m, 2H), 7.85 (d, J = 9.60 Hz, 1H), 9.31 (bs, 1H), 11.68 (bs, 1H) |
| 279 | 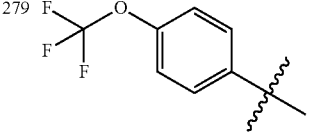 | Me | 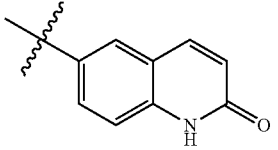 [SMILES: *c1ccc2[nH]c(=O)ccc2c1] | 1 | O | 1.544 | 432.0 | 400 MHz, CDCl3: δ 3.62 (s, 3H), 5.29 (s, 2H), 6.52 (d, J = 9.60 Hz, 1H), 7.29 (s, 2H), 7.33 (d, J = 8.80 Hz, 2H), 7.43 (s, 1H), 7.66 (dd, J = 2.00, 9.80 Hz, 2H), 7.85 (d, J = 9.60 Hz, 1H) |
| 280 | 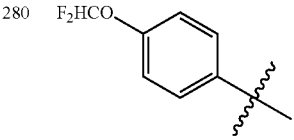 | Me | 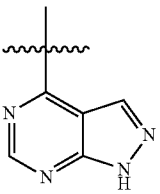 [SMILES: *c1ncnc2[nH]ncc12] | 2 | NH | 0.945 | 402 | 400 MHz, DMSO-d6: δ 3.01 (t, J = 7.20 Hz, 2H), 3.44 (s, 3H), 3.86 (d, J = 6.00 Hz, 2H), 6.90-7.27 (m, 1H), 7.09 (dd, J = 1.20, Hz, 2H), 7.53 (dd, J = 2.00, 7.00 Hz, 2H), 8.10 (s, 1H), 8.25 (s, 1H), 8.40 (s, 1H), 8.61 (s, 1H), 13.40 (s, 1H) |
| 281 | 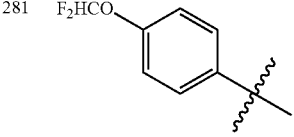 | Et | 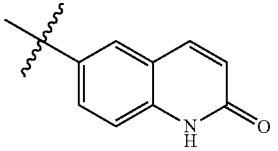 [SMILES: *c1ccc2[nH]c(=O)ccc2c1] | 1 | O | 1.395 | 428 | 400 MHz, DMSO-d6: δ 1.32 (t, J = 7.20 Hz, 3H), 4.08-4.12 (m, 2H), 5.28 (s, 2H), 6.52 (d, J = 9.60 Hz, 1H), 6.95-7.32 (m, 5H), 7.43 (s, 1H), 7.63 (dd, J = 3.20, 11.60 Hz, 2H), 7.85 (d, J = 9.60 Hz, 1H), 11.67 (s, 1H) |
| 282 | 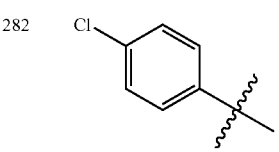 | H | 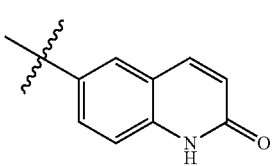 [SMILES: *c1ccc2[nH]c(=O)ccc2c1] | 1 | O | 1.66 | 368 | 400 MHz, DMSO-d6: δ 5.14 (s, 2H), 6.51 (d, J = 9.60 Hz, 1H), 7.25-7.28 (m, 4H), 7.37 (s, 1H), 7.53-7.57 (m, 2H), 7.83 (d, J = 9.60 Hz, 1H), 9.94 (s, 1H), 11.65 (s, 1H) |
| 283 | 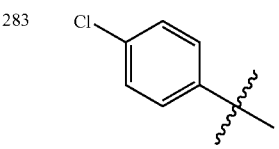 | H | 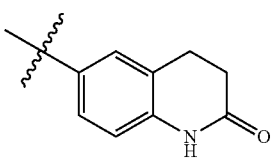 [SMILES: *c1ccc2c(c1)CCC(=O)N2] | 1 | O | 1.65 | 370 | 400 MHz, DMSO-d6: δ 2.41 (t, J = 7.20 Hz, 2H), 2.85 (t, J = 8.00 Hz, 2H), 5.05 (s, 2H), 6.79 (d, J = 8.40 Hz, 1H), 6.86 (dd, J = 2.80, 8.40 Hz, 1H), 6.94 (d, J = 2.80 Hz, 1H), 7.27 (d, J = 8.80 Hz, 2H), 7.56 (dd, J = 2.40, 7.00 Hz, 2H), 9.38 (s, 1H), 9.93 (s, 1H) |

Example 284

6-((5-(3,4-dichlorobenzyl)-4H-1,2,4-triazol-3-yl)methoxy)-3,4-dihydroquinolin-2(1H)-one

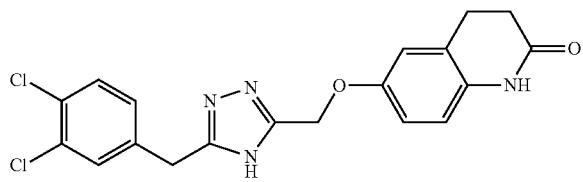 [SMILES: O=C1CCc2cc(OCc3nnc(Cc4ccc(Cl)c(Cl)c4)[nH]3)ccc2N1]

To the stirred solution of methyl 2-(3,4-dichlorophenyl)ethanimidothioate hydroiodide (0.184 g, 0.51 mmol) in dry DMSO (1 mL) were added 2-((2-oxo-1,2,3,4-tetrahydroquinolin-6-yl)oxy)acetohydrazide (0.120 g, 0.51 mmol) and TEA (0.103 g, 1.02 mmol) and heated at 115° C. in a seal tube overnight. Water was added to the reaction mixture. The solid precipate was filtered, dried and purified by preparative HPLC on a Kromasil C4 column (250×20 mm) using a gradient of ACN in 0.1% TFA (0-100%) to give 6-((5-(3,4-dichlorobenzyl)-4H-1,2,4-triazol-3-yl)methoxy)-3,4-dihydroquinolin-2(1H)-one as an off white solid (0.070 g; 34%). 1HNMR 400 MHz, DMSO-d6: δ 2.40 (t, J=7.20 Hz, 2H), 2.82 (t, J=8.00 Hz, 2H), 4.09 (s, 2H), 5.01 (s, 2H), 6.75-6.76 (m, 2H), 6.88 (s, 1H), 7.28 (d, J=8.40 Hz, 1H), 7.59 (d, J=8.00 Hz, 2H), 9.91 (s, 1H), 13.87 (bs, 1H). LCMS: RT 1.71 min; LCMS (ES-API), m/z 403.0.

Example 285

6-((5-(3,4-dichlorobenzyl)-4H-1,2,4-triazol-3-yl)methoxy)quinolin-2(1H)-one

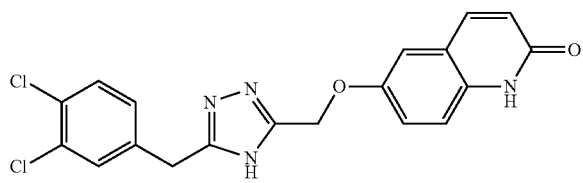 [SMILES: O=c1ccc2cc(OCc3nnc(Cc4ccc(Cl)c(Cl)c4)[nH]3)ccc2[nH]1]

6-((5-(3,4-dichlorobenzyl)-4H-1,2,4-triazol-3-yl)methoxy)quinolin-2(1H)-one was synthesized by a procedure analogous to the synthesis of Example 284. 1H NMR 400 MHz, DMSO-d6: δ 4.03 and 4.14 (two broad singlets, 2H), 5.05 and 5.20 (two broad singlets, 2H), 6.50 (d, J=9.60 Hz, H), 7.24-7.33 (m, 4H), 7.58 (s, 2H), 7.81 (d, J=9.60 Hz, 1H), 11.62 (s, 1H), 13.84 and 14.05 (two broad singlets, 1H). LCMS: RT 1.45 min; LCMS (ES-API), m/z 402.0 (M+H).

Example 286

6-((5-(4-chlorophenyl)-4H-1,2,4-triazol-3-yl)methoxy)-3,4-dihydroquinolin-2(1H)-one

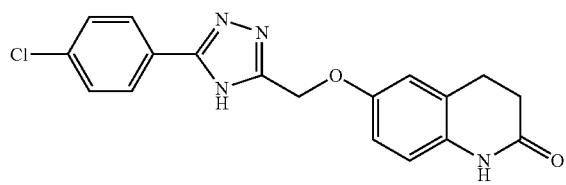 [SMILES: O=C1CCc2cc(OCc3nnc(-c4ccc(Cl)cc4)[nH]3)ccc2N1]

6-((5-(4-chlorophenyl)-4H-1,2,4-triazol-3-yl)methoxy)-3,4-dihydroquinolin-2(1H)-one was synthesized by a procedure analogous to the synthesis of Example 284. 1H NMR 400 MHz, DMSO-d6: δ 2.45 (t, J=8.00 Hz, 2H), 2.85 (t, J=7.20 Hz, 2H), 5.06 and 5.22 (two singlets, 2H), 6.78-6.94 (m, 3H), 7.53 (d, J=8.00 Hz, 1H), 7.63 (d, J=7.60 Hz, 1H), 8.02 (d, J=8.40 Hz, 2H), 9.93 (d, J=10.40 Hz, 1H), 14.34 and 14.54 (two singlets, 1H). LCMS: RT 1.72 min; LCMS (ES-API), m/z 355.0 (M+H).

Example 287

6-((3-(4-chlorobenzyl)-1,2,4-oxadiazol-5-yl)methoxy)-3,4-dihydroquinolin-2(1H)-one

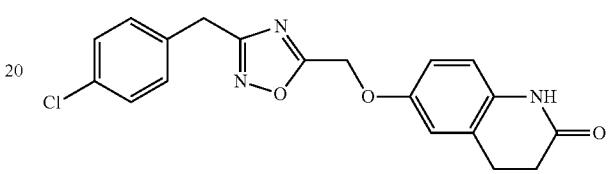

To a stirred solution of ethyl 2-((2-oxo-1,2,3,4-tetrahydroquinolin-6-yl)oxy)acetate (0.1 g, 0.4 mmol) in dry toluene (2 mL), 2-(4-chlorophenyl)-N'-hydroxyacetimidamide (0.073 g, 0.4 mmol) and potassium carbonate (0.1 g, 8 mmol) were added and heated to 110° C. in a microwave oven for 30 min. Solvent was removed under vacuum. Water (5 mL) was added to the residue, and the solid which formed was filtered, dried, and recrystallized using a mixture of ACN/Ethanol to afford 6-((3-(4-chlorobenzyl)-1,2,4-oxadiazol-5-yl)methoxy)-3,4-dihydroquinolin-2(1H)-one as an off-white solid (40 mg, 27%). 1H NMR: 400 MHZ, DMSO-d6: δ 2.40 (t, J=7.20 Hz, 2H), 2.82 (t, J=7.60 Hz, 2H), 4.14 (s, 2H), 5.39 (s, 2H), 6.78-6.83 (m, 2H), 6.89 (d, J=2.40 Hz, 1H), 7.33 (d, J=8.40 Hz, 2H), 7.40 (d, J=8.40 Hz, 2H), 9.95 (s, 1H). LCMS: RT 1.85 min. LCMS (ES-API), m/z 370.0 (M+H).

Example 288

6-(3-(5-(4-chlorophenyl)-1,2,4-oxadiazol-3-yl)propoxy)-3,4-dihydroquinolin-2(1H)-one N'-hydroxy-4-((2-oxo-1,2,3,4-tetrahydroquinolin-6-yl)oxy)butanimidamide

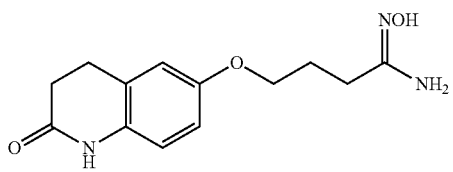

By a method analogous to the preparation of 2-(4-chlorophenyl)-N'-hydroxyacetimidamide, N'-hydroxy-4-((2-oxo-1,2,3,4-tetrahydroquinolin-6-yl)oxy)butanimidamide (0.18 g, 52%) was synthesized. ¹H NMR: 400 MHZ, DMSO-d6: δ 1.88-1.90 (m, 2H), 2.09-2.11 (m, 2H), 2.38-2.40 (m, 2H), 2.81-2.83 (m, 2H), 3.88-3.90 (m, 2H), 5.37 (s, 2H), 6.70-6.70 (m, 3H), 9.89 (s, 1H). LCMS: RT 0.86 min. LCMS (ES-API), m/z 265.0 (M+H).

(Z)—N'-((4-chlorobenzoyl)oxy)-4-(2-oxo-1,2,3,4-tetrahydroquinolin-6-yl)oxy)butanimidamide

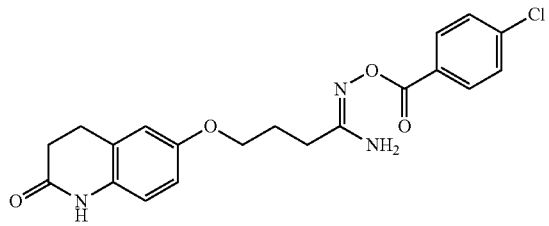 [SMILES: N/C(CCCOc1ccc2c(c1)CCC(=O)N2)=N\OC(=O)c1ccc(Cl)cc1]

To a stirred solution of N'-hydroxy-4-((2-oxo-1,2,3,4-tetrahydroquinolin-6-yl)oxy)butanimidamide (0.100 g, 0.37 mmol) in dry toluene (2 mL) at room temperature, p-chlorobenzoyl chloride (0.066 g, 0.37 mmol) and potassium carbonate (0.061 g) were added. The reaction mixture was heated to 110° C. overnight in a sealed tube. Solids were filtered, then water was added to the filtrate and stirred for few minutes. The solid precipitate which formed was filtered and dried to yield (Z)—N'-((4-chlorobenzoyl)oxy)-4-((2-oxo-1,2,3,4-tetrahydroquinolin-6-yl)oxy)butanimidamide (0.034 g; 22%). 1H NMR: 400 MHZ, DMSO-d6: δ 2.00 (t, J=6.80 Hz, 2H), 2.29 (t, J=7.60 Hz, 2H), 2.40 (t, J=7.20 Hz, 2H), 2.83 (t, J=7.60 Hz, 2H), 3.97 (t, J=6.40 Hz, 2H), 6.60 (s, 2H), 6.76 (s, 2H), 6.82 (s, 1H), 7.58 (d, J=8.40 Hz, 2H), 8.13 (d, J=8.40 Hz, 2H), 9.90 (s, 1H).

6-(3-(5-(4-chlorophenyl)-1,2,4-oxadiazol-3-yl)propoxy)-3,4-dihydroquinolin-2(1H)-one

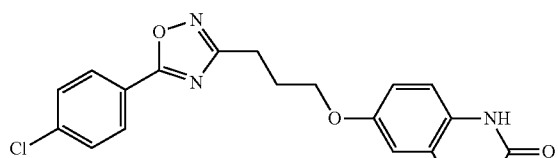

To a stirred solution of (Z)—N'-((4-chlorobenzoyl)oxy)-4-((2-oxo-1,2,3,4-tetrahydroquinolin-6-yl)oxy)butanimidamide (0.030 g, 0.074 mmol) in dry DMF/THF (4 mL, 1:1) at 0° C., TBAF (1 M in THF; 0.02 mL, 0.02 mmol) was added and allowed to stir at room temperature overnight. Solvent was removed under vacuum. Ice cold water (2 mL) was added to the residue. The solid which formed was filtered and dried to yield 6-(3-(5-(4-chlorophenyl)-1,2,4-oxadiazol-3-yl)propoxy)-3,4-dihydroquinolin-2(1H)-one (0.020 g, 71%) as an off-white solid. 1H NMR: 400 MHZ, DMSO-d6: δ 2.16 (t, J=6.80 Hz, 2H), 2.39 (t, J=7.20 Hz, 2H), 2.82 (t, J=8.00 Hz, 2H), 2.95 (t, J=7.60 Hz, 2H), 4.02 (t, J=6.00 Hz, 2H), 6.71- 6.78 (m, 3H), 7.72 (d, J=8.40 Hz, 2H), 8.11 (d, J=8.80 Hz, 2H), 9.89 (s, 1H). LCMS: RT 2.06 min. LCMS (ES-API), m/z 384.0 (M+H).

Example 289

6-((5-(3,4-dichlorobenzyl)-1,3,4-oxadiazol-2-yl)methoxy)quinolin-2(1H)-one

2-(3,4-dichlorophenyl)-N'-(2-((2-oxo-1,2-dihydroquinolin-6-yl)oxy)acetyl)acetohydrazide

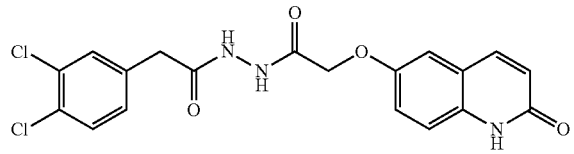 [SMILES: O=C(COc1ccc2[nH]c(=O)ccc2c1)NNC(=O)Cc1ccc(Cl)c(Cl)c1]

To a stirred solution of 2-(3,4-dichlorophenyl)acetic acid (0.440 g, 2.144 mmol) in DMF (15 mL), EDC (0.616 g, 3.22 mmol) and HOBT (0.328 g, 2.144 mmol) were added. The reaction mixture was stirred at room temperature for 10 min. To this suspension was added 2-((2-oxo-1,2-dihydroquinolin-6-yl)oxy)acetohydrazide (0.5 g, 2.144 mmol) and the reaction was stirred at room temperature overnight. The reaction mixture was concentrated and ice cold water was added and stirred for 10 min. The solid which separated was filtered, washed with water, and dried to afford crude 2-(3,4-dichlorophenyl)-N'-(2-((2-oxo-1,2-dihydroquinolin-6-yl)oxy)acetyl)acetohydrazide as a brown solid (0.7 g, 78%). LCMS: RT 1.581 min. LCMS (ES-API), m/z 420.0 (M+H).

6-((5-(3,4-dichlorobenzyl)-1,3,4-oxadiazol-2-yl)methoxy)quinolin-2(1H)-one

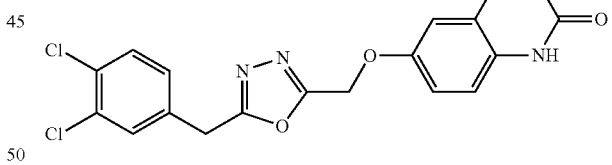

To a stirred solution of 2-(3,4-dichlorophenyl)-N'-(2-((2-oxo-1,2-dihydroquinolin-6-yl)oxy)acetyl)acetohydrazide (0.2 g, 0.476 mmol) and TEA (0.265 mL, 1.904 mmol) in DCM (8 mL) at 0° C., Ts-Cl (0.181 g, 0.952 mmol) was added. The resulting solution was stirred at room temperature overnight. The reaction mixture was concentrated and dissolved in ethyl acetate, then washed with 10% NaHCO3 solution and brine. The organic layer was dried over anhydrous sodium sulfate and concentrated to a yellow gum, which was further washed with diethyl ether and chloroform to afford a brown solid. The crude product was purified by preparative HPLC on a C18 reverse phase column (ACN-NH4OAc method) to afford 6-((5-(3,4-dichlorobenzyl)-1,3,4-oxadiazol-2-yl)methoxy)quinolin-2(1H)-one (0.015 g, 8%). 1H NMR: 400 MHZ, DMSO-d6: δ 4.38 (s, 2H), 5.40 (s, 2H), 6.51 (dd, J=2.00, 9.60 Hz, 1H), 7.25 (d, J=2.40 Hz, 2H), 7.34 (dd, J=2.00, 8.00 Hz, 2H), 7.62 (d, J=8.00 Hz, 1H), 7.65 (d, J=2.00 Hz, 1H), 7.81 (d, J=9.60 Hz, 1H), 11.68 (s, 1H). LCMS: RT 1.61 min. LCMS (ES-API), m/z 403.0 (M+H).

Example 290

6-((5-((3,4-dichlorophenyl)(hydroxy)methyl)-1,3,4-oxadiazol-2-yl)methoxy)-3,4-dihydroquinolin-2(1H)-one

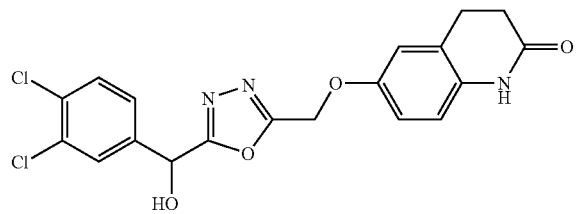 [SMILES: O=C1CCc2cc(OCc3nnc(C(O)c4ccc(Cl)c(Cl)c4)o3)ccc2N1]

A mixture of N-isocyaniminotriphenylphosphorane (0.204 g, 0.678 mmol), 3,4-dichlorobenzaldehyde (0.158 g, 2.712 mmol), and 2-((2-oxo-1,2,3,4-tetrahydroquinolin-6-yl)oxy)acetic acid (0.150 g, 0.678 mmol) in dichloromethane (5 mL) was stirred at room temperature overnight. Solvent was removed under vacuum. The crude product was recystallised in ACN/Ethanol to afford 6-((5-((3,4-dichlorophenyl)(hydroxy)methyl)-1,3,4-oxadiazol-2-yl)methoxy)-3,4-dihydroquinolin-2(1H)-one (40 mg, 14%) as an off white solid. 1H NMR: 400 MHZ, DMSO-d6: δ 2.40 (t, J=7.20 Hz, 2H), 2.82 (t, J=8.00 Hz, 2H), 5.32 (s, 2H), 6.11 (d, J=5.60 Hz, 1H), 6.77 (d, J=8.40 Hz, 1H), 6.82 (dd, J=2.40, 8.60 Hz, 1H), 6.88 (s, 1H), 7.00 (d, J=5.60 Hz, 1H), 7.45 (dd, J=1.60, 8.40 Hz, 1H), 7.67 (d, J=8.40 Hz, 1H), 7.72 (d, J=1.60 Hz, 1H), 9.95 (s, 1H). LCMS: RT 1.76 min. LCMS (ES-API), m/z 422.0 (M+H).

Example 291

6-(2-(5-(4-(trifluoromethyl)phenyl)-1,3,4-oxadiazol-2-ylamino)ethoxy)-3,4-dihydroquinolin-2(1H)-one 5-(4-(trifluoromethyl)phenyl)-1,3,4-oxadiazol-2-amine

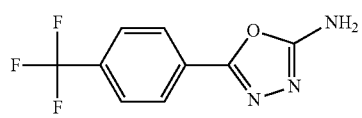 [SMILES: Nc1nnc(-c2ccc(C(F)(F)F)cc2)o1]

To a solution of 4-(trifluoromethyl)benzohydrazide (0.5 g, 2.449 mmol) in dioxane (10 mL) and water (2 mL) was added sodium bicarbonate (0.617 g, 7.35 mmol) and cyanic bromide (0.519 g, 4.90 mmol). The reaction was stirred at room temperature for 15 h. The reaction mixture was diluted with water (50 mL), extracted with EtOAc, dried over sodium sulfate, and evaporated to yield 5-(4-(trifluoromethyl)phenyl)-1,3,4-oxadiazol-2-amine (0.28, 50%). 1H NMR: 400 MHz, DMSO-d6: δ 7.43 (s, 2H), 7.91 (d, J=8.40 Hz, 2H), 8.00 (d, J=8.40 Hz, 2H). LCMS: RT 1.55 min. LCMS (ES-API), m/z 230.0 (M+H).

6-(2-hydroxyethoxy)-3,4-dihydroquinolin-2(1H)-one

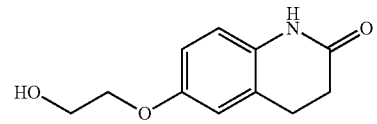 [SMILES: O=C1CCc2cc(OCCO)ccc2N1]

To a solution of ethyl 2-((2-oxo-1,2,3,4-tetrahydroquinolin-6-yl)oxy)acetate (1.5 g, 6.02 mmol) in ethanol (25 mL), was added calcium chloride (0.334 g, 3.01 mmol). The resulting mixture was cooled to −10° C. and NaBH4 (0.455 g, 12.04 mmol) was added, then stirred at 23° C. for 5 h. The reaction mixture was diluted with EtOAc (50 ml), extracted with sat NaHCO3 solution and brine, dried over anhydrous sodium sulfate, and concentrated to afford a white solid. The crude material was purified by silica gel flash chromatography (12 g, 40-100% ethyl acetate in hexanes) to afford 6-(2-hydroxyethoxy)-3,4-dihydroquinolin-2(1H)-one (0.9 g, 64%) as a white solid. LCMS: RT 0.90 min. LCMS (ES-API), m/z 208.0 (M+H).

2-(2-oxo-1,2,3,4-tetrahydroquinolin-6-yloxy)ethyl 4-methylbenzenesulfonate

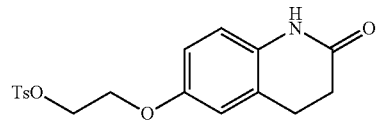 [SMILES: Cc1ccc(S(=O)(=O)OCCOc2ccc3c(c2)CCC(=O)N3)cc1]

To a solution of 6-(2-hydroxyethoxy)-3,4-dihydroquinolin-2(1H)-one (0.15 g, 0.724 mmol) in DCM (2 mL) was added pyridine (0.117 mL, 1.448 mmol) and 4-methylbenzene-1-sulfonyl chloride (0.152 g, 0.796 mmol) and the reaction was stirred for 4 h. The reaction was diluted with EtOAc (25 mL), washed with 0.1 N HCl (10 mL), brine (10 mL), and sat. NaHCO3 solution (10 mL). The organic layer was dried over sodium sulfate, evaporated to dryness, and purified by flash chromatography on silica gel (4 g, 50% EtOAC in hexanes) to yield 2-(2-oxo-1,2,3,4-tetrahydroquinolin-6-yloxy) ethyl 4-methylbenzenesulfonate (0.07 g, 27%).

6-(2-(5-(4-(trifluoromethyl)phenyl)-1,3,4-oxadiazol-2-ylamino)ethoxy)-3,4-dihydroquinolin-2(1H)-one

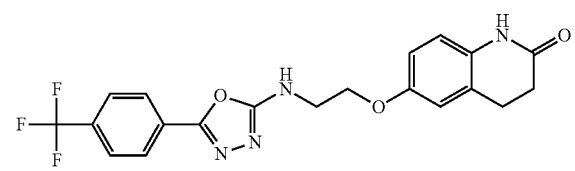 [SMILES: O=C1CCc2cc(OCCNc3nnc(-c4ccc(C(F)(F)F)cc4)o3)ccc2N1]

To a solution of 5-(4-(trifluoromethyl)phenyl)-1,3,4-oxadiazol-2-amine (0.047 g, 0.207 mmol) in DMF (2 mL) added potassium carbonate (0.052 g, 0.376 mmol) and 2-((2- oxo-1,2,3,4-tetrahydroquinolin-6-yl)oxy)ethyl 4-methylbenzenesulfonate (0.068 g, 0.188 mmol) and the reaction stirred at room temperature for 15 h. The temperature was then increased to 60° C. for 15 h. After cooling to room temperature, the mixture was diluted with water (5 mL), extracted with EtOAC (20 mL), dried over sodium sulfate, and evaporated. The residue was purified by preparative HPLC on a X—Terra column (10×150 mm, 5 μm) with 0-100% AcCN in 10 mM aq. NH₄OAc. Solvents were evaporated under vacuum to yield 6-(2-(5-(4-(trifluoromethyl)phenyl)-1,3,4-oxadiazol-2-ylamino)ethoxy)-3,4-dihydroquinolin-2(1H)-one (4.3 mg, 5.5%). 1H NMR: 400 MHz, DMSO-d6: δ 2.53 (dd, J=7.60, 8.40 Hz, 2H), 2.91 (t, J=8.00 Hz, 2H), 3.76 (t, J=5.20 Hz, 2H), 4.20 (t, J=5.20 Hz, 2H), 6.80-6.84 (m, 3H), 7.83 (d, J=8.40 Hz, 2H), 8.07 (d, J=8.00 Hz, 2H). LCMS: RT 1.79 min. LCMS (ES-API), m/z 419.0 (M+H).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

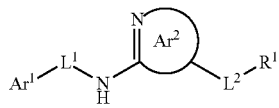

where:
R¹ is selected from the group consisting of

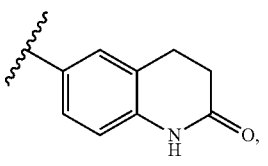

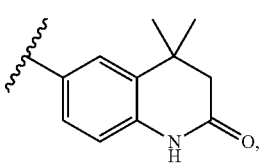

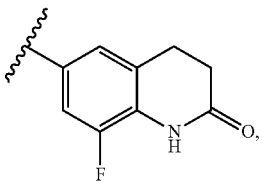

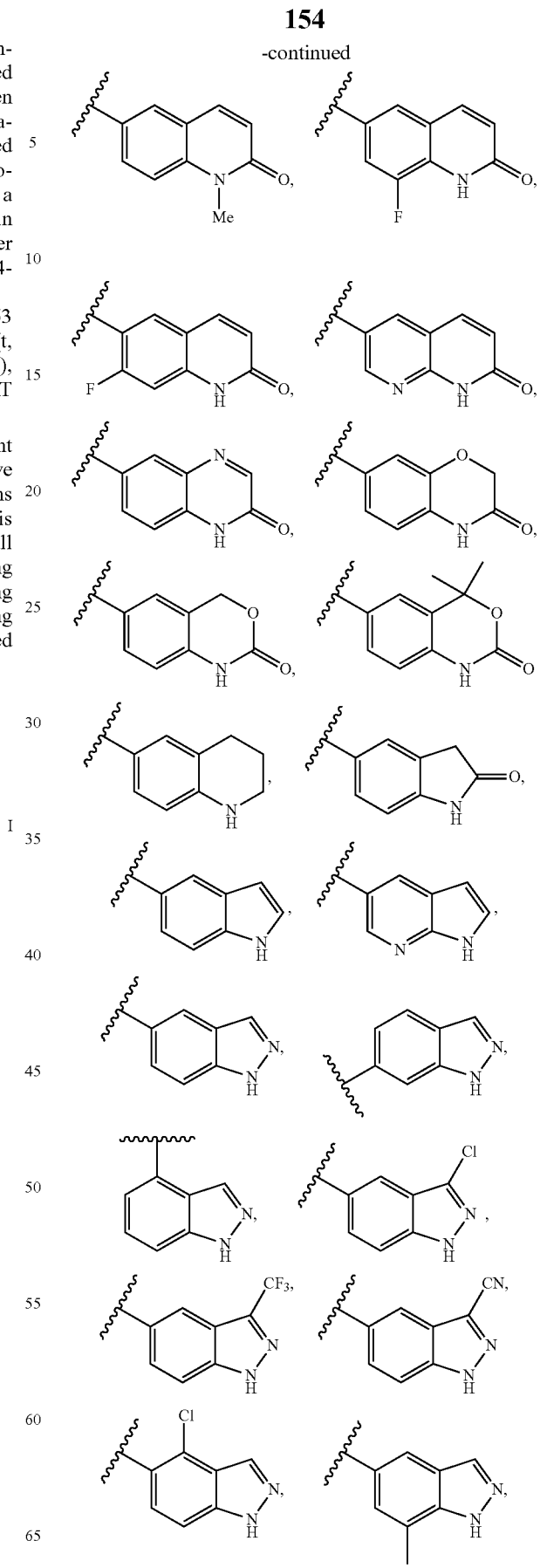

-continued

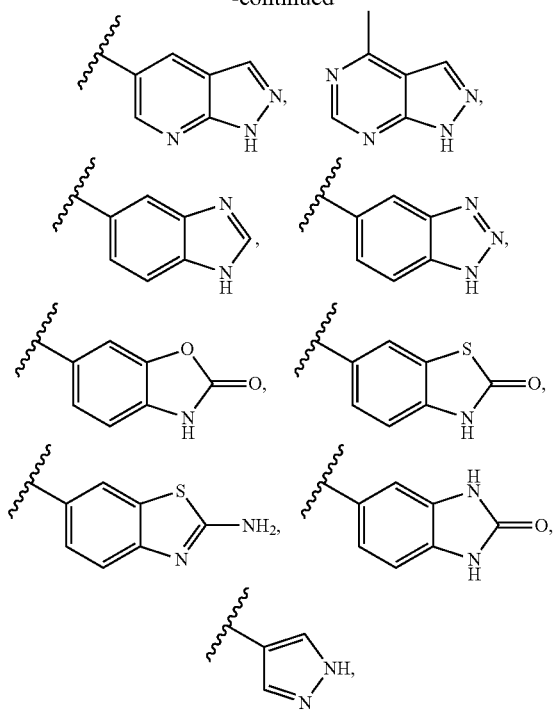

Ar³, ((thiazolyl)amino)phenyl, (pyrimidinyl)amino, and (pyrazolopyrimidinyl)amino;

R² is hydrogen, alkyl, haloalkyl, alkoxy, haloalkoxy, or alkylSO₂;

Ar¹ is phenyl or pyridinyl and is substituted with 0-3 substituents selected from cyano, halo, alkyl, haloalkyl, (alkoxycarbonyl)alkyl, alkoxy, haloalkoxy, dialkylamino, (alkoxycarbonyl)amino, alkylSO₂NH, alkylSO₂, and phenoxy, or Ar¹ is benzodioxolyl or dihydrobenzodioxinyl;

Ar² is

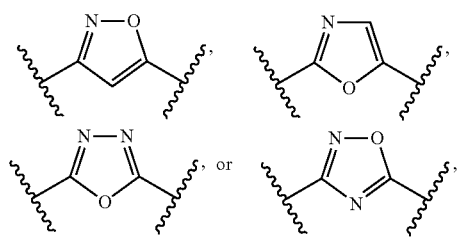

and Ar² is substituted with 0-1 substituents selected from the group consisting of hydroxy, cyano, halo, alkyl, alkoxy, and haloalkoxy;

Ar³ is phenyl, pyridinyl, pyrazinyl, pyrimidinyl, or pyridazinyl, and is substituted with 1 substituent selected from hydroxy, NH₂—, NHCO₂alkyl, and NHSO₂alkyl, and is also substituted with 0-3 substituents selected from halo, alkyl, and haloalkyl;

L¹ is a direct bond, —CH₂—, —C(OH)H—, or —CH₂CH₂—; and

L² is —O—, —CH₂O—, —OCH₂—, —CH₂NH—, —NHCH₂—, —CH₂—, —CH₂CH₂—, —CH(CH₃)CH₂—, —CH₂CH(CH₃)—, —CH₂CH(CH₃)O—, —CH₂CH₂CH₂—, or cyclopropdiyl;

or a pharmaceutically acceptable salt thereof.

2. A compound of claim 1 where:

R¹ is selected from the group consisting of

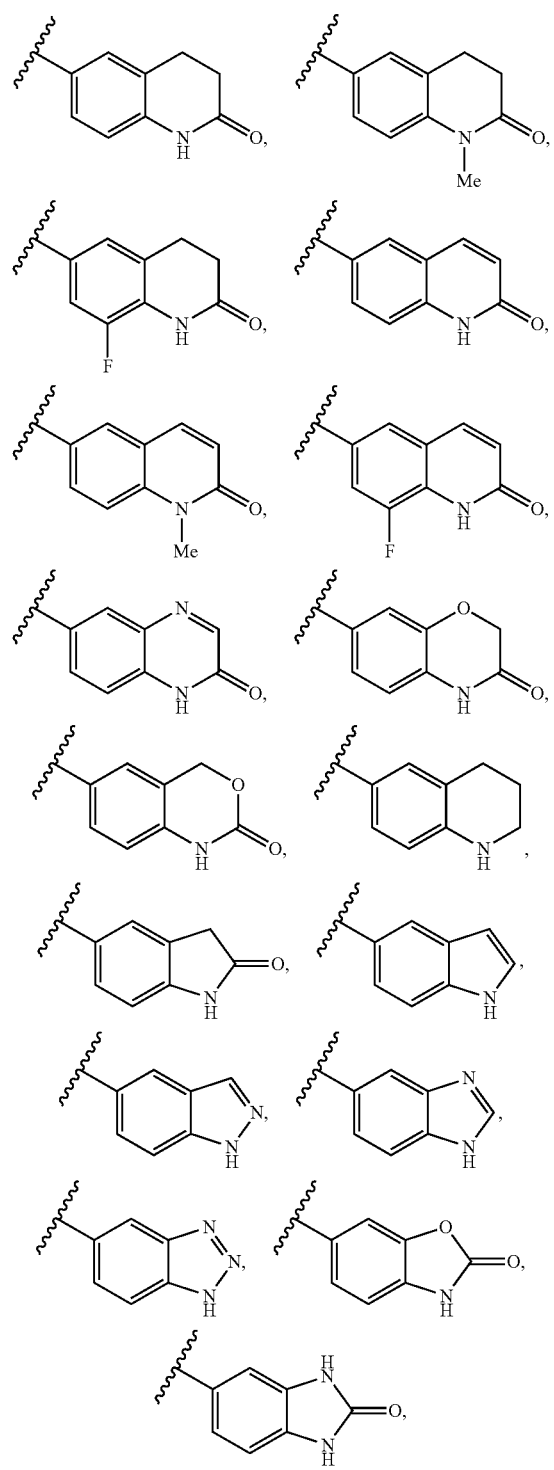

Ar³, and (pyrimidinyl)amino;

R² is hydrogen or alkyl;

Ar¹ is phenyl or pyridinyl and is substituted with 0-3 substituents selected from halo, alkyl, haloalkyl, alkoxy, and haloalkoxy;

Ar² is

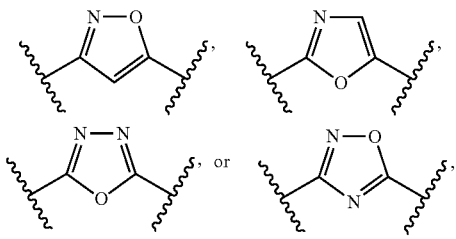

and Ar² is substituted with 0-1 substituents selected from the group consisting of hydroxy, cyano, halo, alkyl, alkoxy, and haloalkoxy;
Ar³ is phenyl, pyridinyl, or pyridazinyl, and is substituted with 1 substituent selected from hydroxy, NHCO₂alkyl, and NHSO₂alkyl, and is also substituted with 0-3 substituents selected from halo, alkyl, and haloalkyl;
L¹ is a direct bond, —CH₂—, or —CH₂CH₂—; and
L² is —CH₂O—, —OCH₂—, —CH₂NH—, —NHCH₂—, —CH₂—, or —CH₂CH₂—;
or a pharmaceutically acceptable salt thereof.

3. A compound of claim 1 where
R¹ is selected from the group consisting of

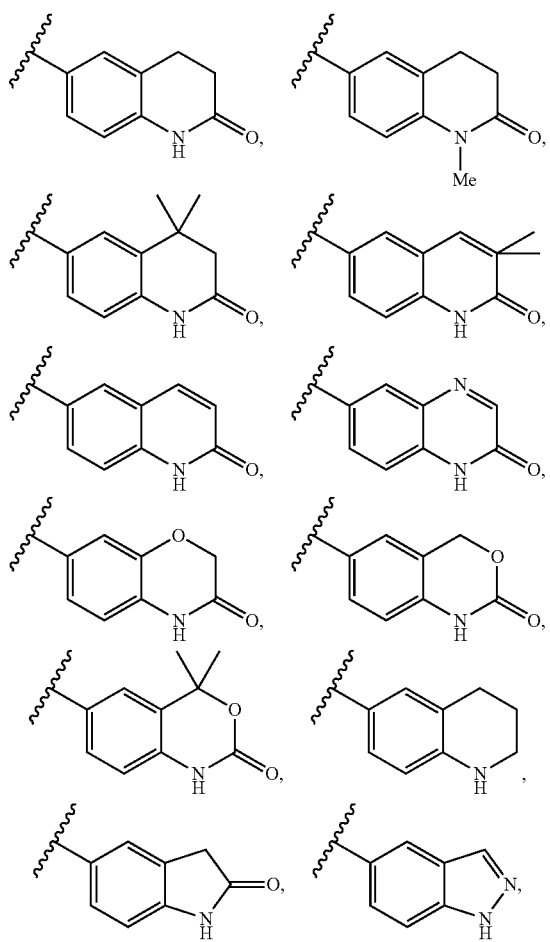

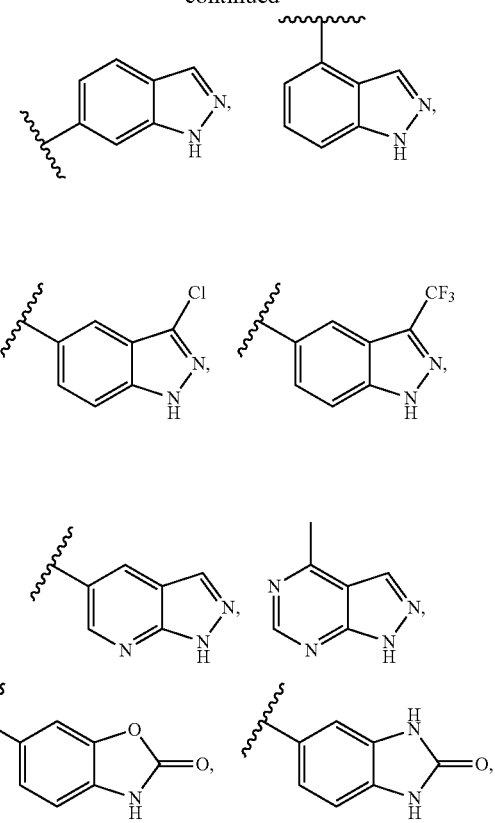

Ar³, (pyrimidinyl)amino, and (pyrazolopyrimidinyl)amino;
R² is hydrogen or alkyl;
Ar¹ is phenyl or pyridinyl and is substituted with 0-3 substituents selected from cyano, halo, alkyl, haloalkyl, (alkoxycarbonyl)alkyl, alkoxy, haloalkoxy, alkoxycarbonyl)amino, alkylSO₂NH, and phenoxy, or Ar¹ is benzodioxolyl or dihydrobenzodioxinyl;
Ar² is

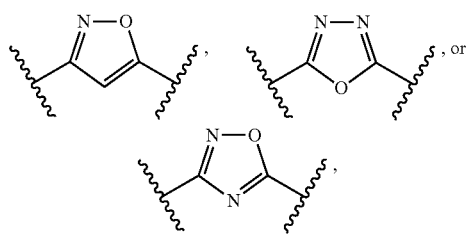

and Ar² is substituted with 0-1 substituents selected from the group consisting of hydroxy, cyano, halo, alkyl, alkoxy, and haloalkoxy;
Ar³ is phenyl, pyridinyl, or pyridazinyl, and is substituted with 1 substituent selected from hydroxyl and NH₂—, and is also substituted with 0-3 halo substituents;
L¹ is a direct bond, —CH₂—, or —C(OH)H—; and
L² is —CH₂O—, —CH₂CH₂—, —CH(CH₃)CH₂—, —CH₂CH(CH₃)O—, or cyclopropdiyl;
or a pharmaceutically acceptable salt thereof.

4. A compound of claim 1 where

R[1] is selected from the group consisting of

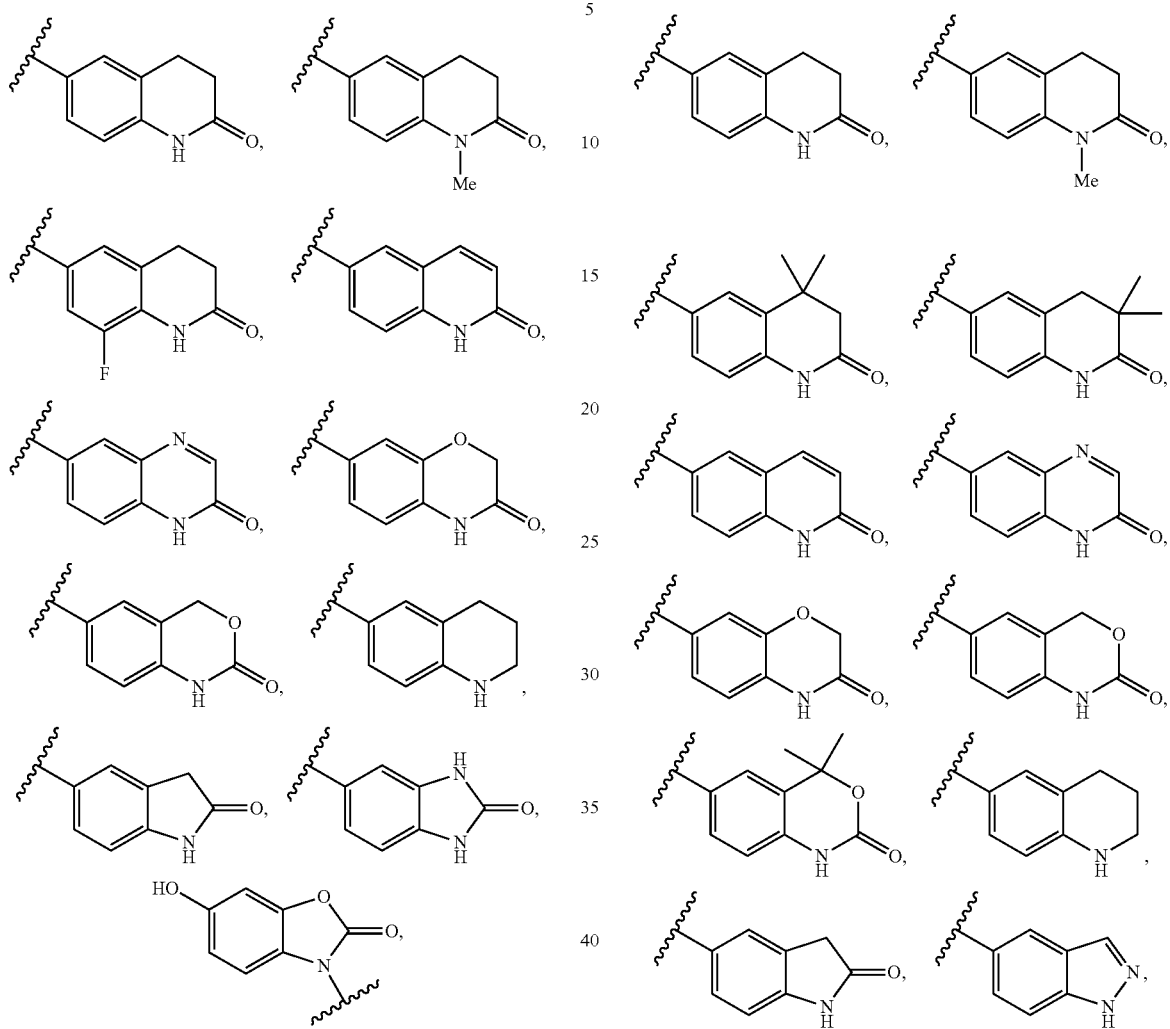

Ar[3], and (pyrimidinyl)amino;

Ar[1] phenyl or pyridinyl and is substituted with 0-3 substituents selected from halo, alkyl, haloalkyl, alkoxy, and haloalkoxy;

Ar[2] is

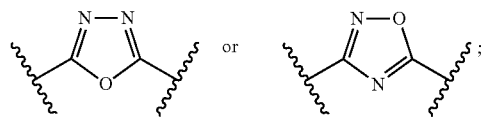 [SMILES: *c1nnc(*)o1 ; *c1noc(*)n1]

Ar[3] is phenyl or pyridazinyl, and is substituted with 1 substituent selected from hydroxy, NHCO$_2$alkyl, or NHSO$_2$alkyl, and is also substituted with 0-3 substituents selected from halo, alkyl, and haloalkyl;

L[1] is a direct bond, or —CH$_2$—; and

L[2] is —CH$_2$O—, —CH$_2$—, or —CH$_2$CH$_2$—;

or a pharmaceutically acceptable salt thereof.

5. A compound of claim 1 where

R[1] is selected from the group consisting of

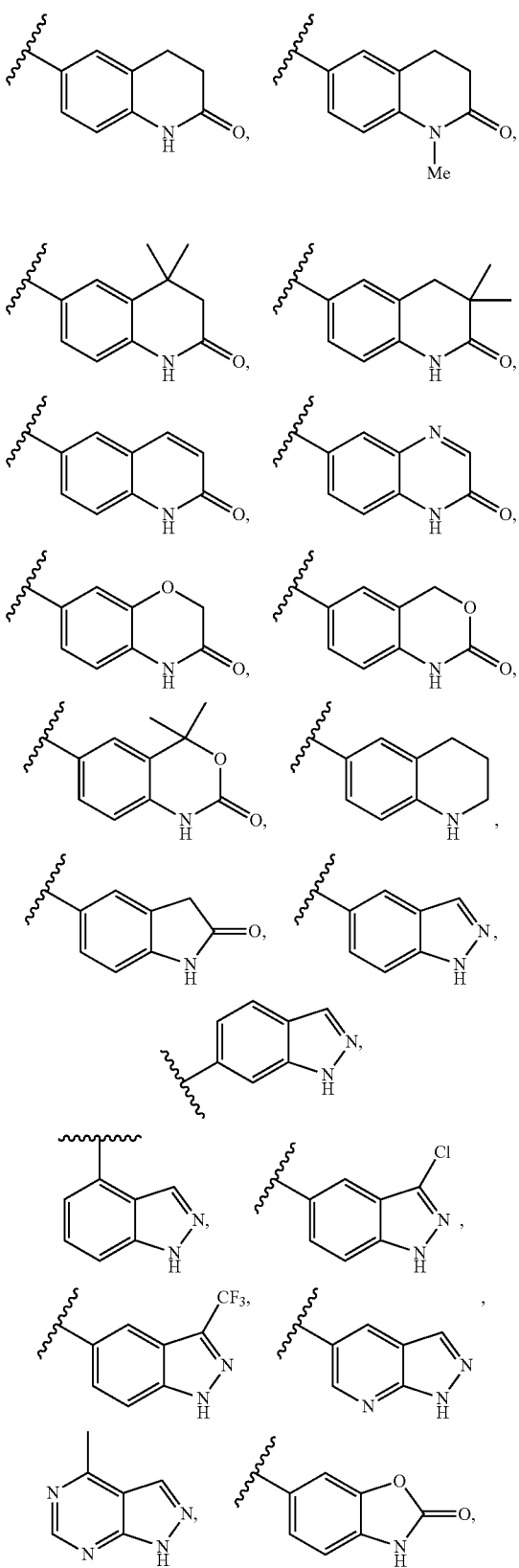

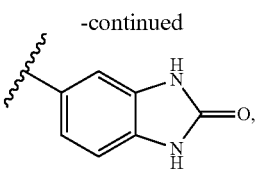

Ar³, (pyrimidinyl)amino, and (pyrazolopyrimidinyl)amino.

6. A compound of claim 1 where Ar¹ is phenyl or pyridinyl and is substituted with 0-3 substituents selected from cyano, halo, alkyl, haloalkyl, (alkoxycarbonyl)alkyl, alkoxy, haloalkoxy, alkoxycarbonyl)amino, alkylSO₂NH, and phenoxy, or Ar¹ is benzodioxolyl or dihydrobenzodioxinyl.

7. A compound of claim 1 where Ar³ is phenyl, pyridinyl, or pyridazinyl, and is substituted with 1 substituent selected from hydroxyl and NH₂—, and is also substituted with 0-3 halo substituents.

8. A compound of claim 1 where L¹ is a direct bond, —CH₂—, or —C(OH)H—.

9. A compound of claim 1 where L² is —CH₂O—, —CH₂CH₂—, —CH(CH₃)CH₂—, —CH₂CH(CH₃)O—, or cyclopropdiyl.

10. A pharmaceutical composition comprising a compound of claim 1 or a pharmaceutically acceptable salt thereof and a pharmaceutically acceptable carrier.

11. A method for the treatment of depression, neuropathic pain, or Parkinson's disease, which comprises administering to a patient a therapeutically affective amount of a compound of claim 1.

12. The method of claim 11 directed to the treatment of depression.

13. The method of claim 11 directed to the treatment of neuropathic pain.

* * * * *

UNITED STATES PATENT AND TRADEMARK OFFICE
CERTIFICATE OF CORRECTION

PATENT NO.         : 8,722,670 B2                                             Page 1 of 1
APPLICATION NO.    : 13/627130
DATED              : May 13, 2014
INVENTOR(S)        : Dalton King et al.

It is certified that error appears in the above-identified patent and that said Letters Patent is hereby corrected as shown below:

In the Claims:

Claim 1:

Column 154, line 28, after " 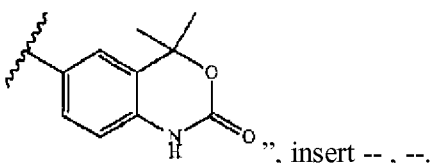 ", insert -- , --.

Claim 3:

Column 158, lines 40 and 41, change "alkoxycarbonyl)amino," to
-- (alkoxycarbonyl)amino, --.

Claim 6:

Column 161, line 13, change "alkoxycarbonyl)amino," to -- (alkoxycarbonyl)amino, --.

Signed and Sealed this
Thirty-first Day of March, 2015

Michelle K. Lee
*Director of the United States Patent and Trademark Office*